(12) United States Patent
Nicolaou et al.

(10) Patent No.: US 8,207,188 B2
(45) Date of Patent: Jun. 26, 2012

(54) TREATMENT OF DISEASES MODULATED BY A H4 RECEPTOR AGONIST

(76) Inventors: Michalis Nicolaou, San Diego, CA (US); Emile Loria, La Jolla, CA (US); Gaetan Terrasse, Saint-Valier (FR); Yves Trehin, Blesle (FR)

(*) Notice: Subject to any disclaimer, the term of this patent is extended or adjusted under 35 U.S.C. 154(b) by 385 days.

(21) Appl. No.: 12/486,725

(22) Filed: Jun. 17, 2009

(65) Prior Publication Data

US 2010/0144718 A1    Jun. 10, 2010

Related U.S. Application Data

(63) Continuation-in-part of application No. 11/784,992, filed on Apr. 9, 2007, now abandoned, and a continuation-in-part of application No. 12/069,775, filed on Feb. 12, 2008.

(60) Provisional application No. 61/073,288, filed on Jun. 17, 2008, provisional application No. 60/790,490, filed on Apr. 7, 2006, provisional application No. 60/816,754, filed on Jun. 26, 2006, provisional application No. 60/889,423, filed on Feb. 12, 2007, provisional application No. 60/892,325, filed on Mar. 1, 2007, provisional application No. 60/974,685, filed on Sep. 24, 2007.

(51) Int. Cl.
*A01N 43/42* (2006.01)
*A61K 31/44* (2006.01)
*C07D 491/00* (2006.01)
*C07D 498/00* (2006.01)
*C07D 515/00* (2006.01)

(52) U.S. Cl. .................................. 514/292; 546/90

(58) Field of Classification Search .................. 514/292; 546/90

See application file for complete search history.

(56) References Cited

U.S. PATENT DOCUMENTS

| 2002/0137764 A1* | 9/2002 | Drechsel et al. ............... 514/301 |
| 2004/0224876 A1 | 11/2004 | Jost-Price et al. |
| 2005/0042283 A1 | 2/2005 | Wang |
| 2005/0158303 A1 | 7/2005 | Liu et al. |
| 2009/0324699 A1* | 12/2009 | Preswetoff-Morath et al. ........................ 424/450 |

FOREIGN PATENT DOCUMENTS

WO    WO 03/000289    *    1/2003

OTHER PUBLICATIONS

Marton et al. (Monatshefte fur Chemie 124, 291-297, 1993).*
Igel et al. (Biorganic & Medicinal Chemistry Letters 20 2010,7191-99).*
Texas GERD Institute, Center for GERD Care—Acid reflux symptoms and Treatments accessed Jun. 20, 2011 at http://www.gerdcare.org/gerd-causes.htm.
Parmar et al., "Histidine Decarboxylase Inhibition: A Novel Approach Towards the Development of an Effective and Safe Gastric Anti-ulcer Drug," *Agents and Actions*, 1984, 15:495-9.

* cited by examiner

*Primary Examiner* — Sreeni Padmanabhan
*Assistant Examiner* — Uma Ramachandran
(74) *Attorney, Agent, or Firm* — Adriano & Associates

(57) ABSTRACT

The invention provides a method for the treatment of H4R modulated diseases and/or conditions comprising administering to the subject an effective amount of a H4R agonist. The invention also provides a method for treating COPD comprising administering to the subject an effective amount of a H4R agonist, a H1R antagonist and an anticholinergic drug. Further, the invention provides a pharmaceutical formulation comprising a H4R agonist, a second active agent and a pharmaceutically acceptable carrier.

2 Claims, 24 Drawing Sheets

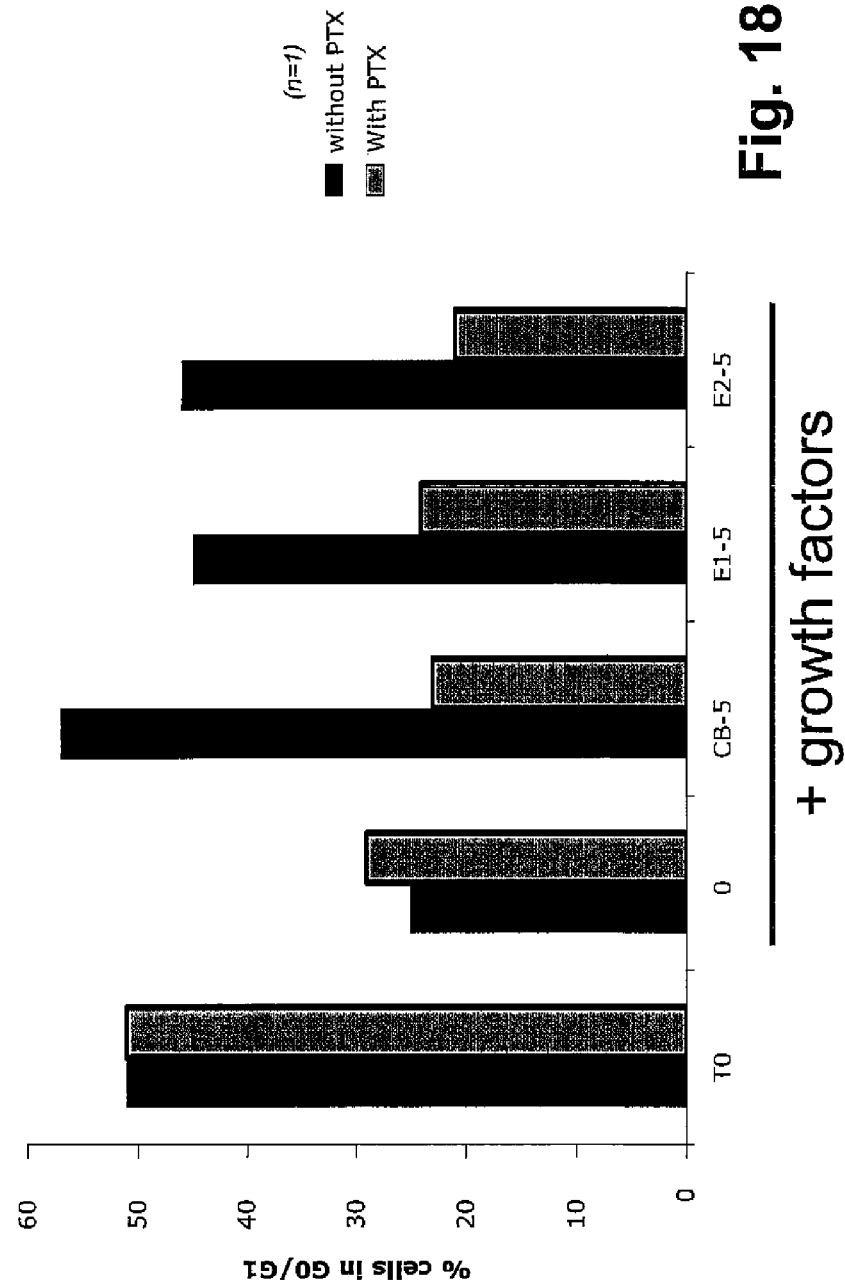

TRQ and hematopoietic progenitor sensitivity to antineoplasic chemotherapeutic agents

TRQ does not significantly alter biogenic monoamine uptake either by Organic Cation Transporter-3 (OCT-3) or by Serotonin Transporter (SERT)

TREATMENT OF DISEASES MODULATED BY A H4 RECEPTOR AGONIST

This application claims the priority of U.S. Ser. No. 61/073,288, filed Jun. 17, 2008 and is a continuation-in-part of U.S. Ser. No. 11/784,992, filed Apr. 9, 2007 now abandoned (which claims the priorities of U.S. Ser. No. 60/790,490, filed Apr. 7, 2006 and U.S. Ser. No. 60/816,754, filed Jun. 26, 2006); and U.S. Ser. No. 12/069,775, filed Feb. 12, 2008 (which claims the priorities of U.S. Ser. No. 60/889,423, filed Feb. 12, 2007, U.S. Ser. No. 60/892,325, filed Mar. 1, 2007 and U.S. Ser. No. 60/974,685, filed Sep. 24, 2007), the contents of all of which are hereby incorporated by reference, in their entirety, into this application, and from which priority is hereby claimed.

Throughout this application various publications are referenced. The disclosures of these publications in their entireties are hereby incorporated by reference into this application in order to more fully describe the state of the art to which this invention pertains.

BACKGROUND OF THE INVENTION

The H4R is the most recently identified and characterized histamine receptor (for reviews, see de Esch J. P., et al., Trends Pharmacol. Sci. 2005, 26(9), 462-469). The receptor is found in the bone marrow and spleen and is expressed on eosinophils, basophils, mast cells (Liu, C., et al., Mol. Pharmacol. 2001, 59(3), 420-426; dendritic cells, and human synovial cells from rheumatoid arthritis patients (Ikawa, Y., et al., Biol. Pham. Bull. 2005, 28(10), 2016-2018). More recently new variants of H4 receptors were described by Richard M. van Rijn, et al. (Biochem. J. (2008) Immediate Publication, doi:10.1042/BJ20071583).

In contrast to the other histamine receptors, H4R has a distinct expression profile on immune and other cells and modulates their function (immuno-modulatory role). Such cells include: mast cells, eosinophils, dendritic cells, T cells, monocytes and macrophages and antigen presenting cells in general. It is also present in endothelial and epithelial cells. The H4R appears to play a role in multiple functions of these cells, such as, activation, migration, differentiation, and cytokine and chemokine production. While the H4R has been identified and characterized, its functions and involvement in disease is still under study.

Currently, treatment of histamine related diseases generally focuses on the design of antagonists for H1R and H2R for the treatment of such diseases. For example, for allergies, antagonists of H1R such as loratadine, fexofenadine, diphenyl-hydramine, cetirizine, brompheniramine, cyproheptadine, dexchlorpheniramine, hydroxizine, ketotifen, mequitazine, oxotomide, mizolastine, ebastine, astemizole, carbinoxamide, alimemazine, buclizine, cyclizine hydrochloride, and doxylamine and others were developed. For stomach conditions exacerbated by gastric acid, antagonists of H2R such as cimetidine, ranitidine, famotidine, and nizatidine and others, were developed.

H4R antagonists have been proposed to have therapeutic potential in a number of inflammatory diseases including Inflammatory Bowel Disease (IBD), Systemic Lupus Erythematosus (SLE), atherosclerosis, allergy and asthma and others. (Zhang M, Thurmond R L, Dunford P J, The histamine H(4) receptor: a novel modulator of inflammatory and immune disorders. Pharmacol Ther. 2007 March; 113(3): 594-606).

There are very few examples of compounds, much less of marketed therapeutics, that have H1R, H2R or H3R agonist activity. An example of a compound that has some H1R agonist activity is betahistine, N-methyl-2-pyridin-2-ylethanamine(betahistine), a H3 antagonist low H1 agonist. Betahistine is not a full H1 agonist. It is a potent H3 antagonist with a low H1 agonist activity. Betahistine has a very strong affinity for histamine H3 receptors and a weak affinity for histamine H1 receptors. Betahistine seems to dilate the blood vessels within the middle ear which can relieve pressure from excess fluid and act on the smooth muscle. It is used for the treatment of Menière syndrome (Review Article. CNS Drugs 2001: 15(11) 855-870). Examples of H3 agonists include: immepip 4-(3H-imidazol-4-ylmethyl)piperidine, imetit S-[2-(4-imidazolyl)ethyl]isothiourea. Immepip and Immetit, although not marketed drugs, are H3 receptor agonists and are currently used in studies in animals with aim to elucidate the H3 receptor function and derive possible therapeutic utility for brain disorders. Examples of H2 agonists include: Betazole 2-(2H-Pyrazol-3-yl)ethanamine, impromidine, N-[3-(imidazol-4-yl)-propyl]-N'-{2-[(5-methylimidazol-4-yl)methylthio]ethyl}-guanidine. Betazole and impromidine are histamine H2 agonists, used clinically as diagnostic tools to test gastric secretory function.

All examples of therapeutic molecules presented above do not utilize the H-receptor agonist activity as the major therapeutic function. In the case of Betahistine, the main therapeutic activity may not be predominantly due to the H1 agonist activity, but due to the H3 antagonist activity. The remainder agonist cases have a diagnostic utility or basic research and investigative use.

There is currently no commercially available drug to treat H4R modulated diseases that is a H4R agonist. Thus, there is an unmet and unperceived need to develop H4R agonists to treat H4R modulated diseases.

Anticholinergics

Anticholinergics are used in the treatment of COPD because they widen the airways by relaxing smooth muscle. They do this by blocking acetylcholine receptors. Acetylcholine is a chemical produced by the brain that causes muscle contraction, which in turn constricts airways. Anticholinergics are considered first-line therapy for COPD.

Examples of anticholinergics include, but are not limited to: tiotropium bromide (Spiriva®) and ipratropium bromide (Atrovent®). Atrovent is the only inhaled anticholinergic agent available in the United States.

Combination Inhalers

Recently, a new product called Advair® was FDA approved for asthma but it may also be beneficial in the treatment of COPD. It combines two medications that have been on the market, salmeterol (a longer acting beta2-agonist) and fluticasone (a steroid). Many patients require both medications to help prevent asthma or COPD symptoms from worsening, but until now were only available as separate inhalers. Advair® cannot be used to quickly relieve asthma or COPD symptoms, it is to be taken on a scheduled basis without regard for the symptoms the patient is having at that particular moment.

Another combination inhaler is Combivent®. It contains two medications: albuterol and ipratropium. Albuterol is an inhaled beta-agonist that works in the lungs to open airways and allow for easier breathing. It does this by stimulating the beta-receptors, which are a certain type of receptor located in the lungs, which help regulate constriction and dilation of the airways. Ipratropium is an anticholinergic used in the treatment of COPD to widen the airways by relaxing and opening air passages to the lungs, making it easier to breathe.

Corticosteroids

Corticosteroids are used to treat many health conditions. This drug class is mainly used for treating asthma, but it has been used for treating COPD. Oral corticosteroids decrease inflammation in the lungs that is associated with COPD. They may take longer to work than inhaled corticosteroids, since they have to travel through the bloodstream before they get to the lungs to work. Corticosteroids are only used in COPD patients who do not respond well to other standard therapies.

Inhaled Beta-2 Agonists

Beta2-agonists work in a manner similar to adrenaline, opening airways and easing breathing. They work by binding with, and thus stimulating, "beta2-receptors" that line the cell walls of the lungs and the bronchioles. The effect of this stimulation is to relax smooth muscles and widen the airways. In COPD, beta2-agonists should be scheduled instead of taken on as needed basis. Possible side effects to the beta2-agonists include shakiness, rapid heartbeat, and upset stomach.

Until recently, all available beta2-agonists were ones that worked quickly but lasted for a relatively short time—about 4-6 hours. Longer-acting beta2-agonists have since been introduced. They cannot be used to quickly relieve symptoms, because there is a delay before they start working. Currently there are two on the market: salmeterol (Serevent®) and formoterol (Foradil®). Longer-acting beta2-agonists are prescribed as maintenance medications which are to be taken on a scheduled basis without regard for the symptoms the patient is having at that particular moment. A short-acting beta2-agonist is best to treat acute symptoms of shortness of breath.

Inhaled Corticosteroids

Corticosteroids suppress the body's production of substances that trigger inflammation and reduce the production of substances that maintain inflammation. This drug class is mainly used for treating asthma, but it has been used for treating COPD. Corticosteroids are only used in COPD patients who do not respond well to other standard therapies.

Mucolytics

This class of drugs is used to thin the mucus associated with cough caused by thick mucus. Mucolytics make it easier to clear the mucus, which can be irritating and cause a cough.

Oral Beta-2 Agonists

Oral beta2-agonists works in a similar fashion to inhaled beta2-agonists, but they may take longer to work than the inhaled formulation. Oral beta-agonists must be absorbed in the digestive tract and travel through the circulatory system before they begin working in the lungs, whereas the inhaled formulations go straight to the lungs.

Theophyllines

Theophyllines appear to widen airways by relaxing the smooth muscles surrounding the airways. Theophylline is also used as a long-acting bronchodilator to prevent COPD symptoms. Taken orally as tablets, capsules, or liquids, theophylline is available in immediate-release and controlled-release formulations as well as injection (aminophylline).

Tritoqualine

7-Amino-4,5,6-triethoxy-3-(5,6,7,8-tetrahydro-4-methoxy-6-methyl-1,3-dioxolo[4,5-g]isoquinolin-5-yl) phthalide or Tritoqualine (TRQ) is a drug, currently formulated in 100 mg tablets and sold in pharmacies in Europe for the treatment of allergy.

Tritoqualine is an inhibitor of the enzyme histidine decarboxylase (HDC), which catalyzes histidine decarboxylation in vivo to produce histamine, an endogenous biogenic amine, plus carbon dioxide. Inhibiting histamine production in the body is proposed to ameliorate symptoms of allergy.

Leukotriene Receptor Antagonists

Leukotriene Receptor Antagonists (LRAs), e.g., Montelukast® and Zafirlukast®) have been traditionally used for the treatment of asthma.

SUMMARY OF THE INVENTION

The invention disclosed herein relates to the surprising discovery that H4R agonists can be used for the treatment of H4R related diseases modulated by H4R. The invention relates generally to the treatment or amelioration of H4R modulated diseases with H4R agonists.

The invention further relates to methods of using H4R agonists, alone, or in combination with one or more other active agents to achieve desirable therapeutic effects for H4R modulated diseases. Agents that can be used in combination with H4R agonists are, for example, other H4R agonists, H1R antagonists (e.g. anti-H1 drug), H2R antagonists (e.g. anti-H2 drug), H3R antagonists (e.g. anti-H3 drug), LRA and NSAIDS.

The invention also relates to methods of providing a plasma concentration of H4R and/or the other compound(s) with a peak-to-trough ratio of less than 3.5, less than 3.0, less than 2.5 or less than 2.0, over a time period spanning from about 1 hour to about 6 hours after administration to a subject.

The invention further relates to pharmaceutical formulations comprising a H4R agonist, one or more of a H1R antagonist, H2R antagonist, H3R antagonist, LRA and NSAID, and a pharmaceutically acceptable carrier.

The invention further provides pharmaceutical formulations comprising therapeutically effective amounts of an H1R antagonist, H2R antagonist, H3R antagonist, LRA and NSAID, and a pharmaceutically acceptable carrier useful to treat a H4R modulated disease.

The active compounds (e.g., H4R agonist, H1R antagonist, H2R antagonist, H3R antagonist, LRA, NSAID) in the pharmaceutical formulation may be combined in a single dosage form or for unit-dose or multi-dose administration. Pharmaceutical carriers suitable for administration of the compounds include any such carriers known to those skilled in the art to be suitable for the particular route of administration and/or suitable for a desired release rate (e.g., immediate or controlled release) of the active compounds. The multiple active ingredients can be formulated into suitable pharmaceutical preparations such as solutions, suspensions, tablets, dispersible tablets, capsules, powders, sustained release, for oral administration or in sterile solutions or suspensions for parenteral administration, as well as transdermal patch preparation, nasal formulation and dry powder inhalers et al. The compositions are formulated into pharmaceutical compositions using techniques and procedures well known in the art.

The pharmaceutical formulations of the invention provide a plasma concentration of the active compounds with a peak-to-trough ratio of less than 3.5, less than 3.0, less than 2.5 or less than 2.0 over a time period spanning from about 1 hour to about 6 hours after administration to a subject.

The invention further relates to treatment or prevention of COPD using drug combinations comprising a H4R agonist, an anti-H1 drug and an anticholinergic drug. The drug combination can further comprise any one or more of existing COPD therapies including but not limited to combination inhaler, corticosteroids, inhaled beta-2 agonists, inhaled corticosteroids, mucolytics, oral beta-2 agonists and theophyllines.

BRIEF DESCRIPTION OF THE FIGURES

FIG. 18 is a bar graph that shows that pertussis toxin (PTX) reverses TRQ's effects by decreasing number of ckit positive bone marrow cells in the G0 and/or G1 phase of the cell cycle.

DETAILED DESCRIPTION OF THE INVENTION

Definitions

Figure 1:
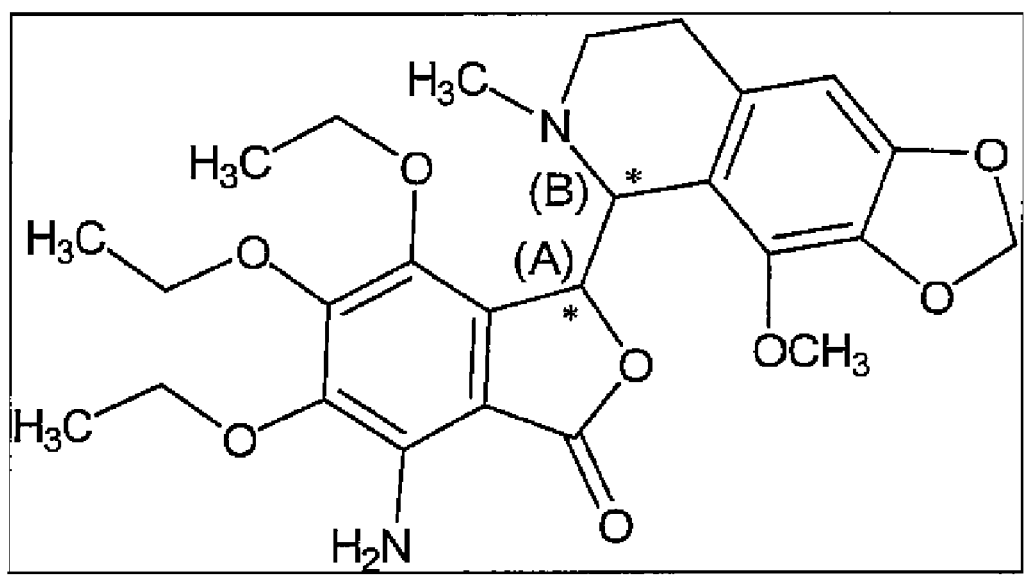
FIG. 1 illustrates the chemical formula of Tritoqualine (7-Amino-4,5,6-triethoxy-3-(5,6,7,8-tetrahydro-4-methoxy- 6-methyl-1,3-dioxolo[4,5-g]isoquinolin-5-yl) phthalide), as described in Example 3, below.

As used herein "allergy" is an abnormal or altered immunologic reaction induced by an allergen in a subject who suffers from hypersensitivity to that allergen including antibody-antigen reactions that include immediate type hypersensitivity reactions such that when IgE molecules are crosslinked with an allergen(s), mast cells and basophils release mediators such as histamines. Examples of allergy symptoms include sinusitis, rhinitis, hives, headaches, post-nasal drip, coughing, sneezing, respiratory difficulties, sore throats, allergic asthma, allergic conjunctivitis, allergic rhinitis, tightness in throat and chest, and loss of voice.

For purposes of the present invention the term "controlled release" refers to a pharmaceutical dosage form which releases one or more active pharmaceutical agents over a prolonged period of time, e.g. over a period of more than 1 hour. Controlled release (CR) components can also be referred to as sustained release (SR), prolonged release (PR), or extended release (ER). When used in association with the dissolution profiles discussed herein, the term "controlled release" refers to that portion of a dosage form made according to the present invention which delivers the compositions of the invention over a period of time e.g. greater than 1 hour. The term "modified release" and "controlled release" is used interchangeably herein.

The term "immediate release" refers to a dosage form which releases the compositions of the invention substantially immediately upon contact with gastric juices and will result in substantially complete dissolution within about 1 hour. Immediate release (IR) components can also be referred to as instant release. When used in association with the dissolution profiles discussed herein, the term "immediate release" refers to that portion of a dosage form made according to the present invention which delivers the compositions of the invention over a period of time less than 1 hour.

The term "derivative" means a chemically modified compound wherein the modification is considered routine by the ordinary skilled chemist, such as an ester or an amide of an acid, protecting groups, such as a benzyl group for an alcohol or thiol, and tert-butoxycarbonyl group for an amine.

The term "effective amount" means an amount of a compound or composition according to the present invention effective in producing the desired therapeutic effect.

The term "analog" means a compound which comprises a chemically modified form of a specific compound or class thereof, and which maintains the pharmaceutical and/or pharmacological activities characteristic of said compound.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The phrase "pharmaceutically acceptable" is employed herein to refer to those compounds, materials, compositions; and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "about" when used in connection with percentages means±1-5%.

The term "H4R agonists" means any molecule that is an agonist to the H4 receptor. Examples of H4 agonists include, but are not limited to, Tritoqualine (TRQ) or derivative thereof (e.g. racemic versions thereof), Tritoqualine isomers (e.g., E1 and E2 enantiomers), 4-methylhistmime (4MeHA) and clobenprobit (CB).

The term "anti-H1" refers to any drug that is an antagonist to the H1 receptor. Examples of H1R antagonists include, but are not limited to, brompheniramine, cetirizine, fexofenadine, cyproheptadine, dexchlorpheniramine, hydroxizine, ketotifen, loratadine, mequitazine, oxotomide, mizolastine, ebastine, astemizole, carbinoxamide, alimemazine, buclizine, cyclizine hydrochloride, doxylamine, mepyramine, antazoline, diphenhydramine, carbinoxamine, clemastine, dimenhydrinate, pheniramine, chlorphenamine, triprolidine, chlorcyclizine, hydroxyzine, meclizine, promethazine, and azatadine.

The term "anti-H2" refers to any drug that is an antagonist to the H2 receptor. Examples of H2R antagonists include, but are not limited to, ranitidine, cimetidine, famotidine, and nizatidine.

The term "anti-H3" refers to any drug that is an antagonist to the H3 receptor. Examples of H3R antagonists include, but are not limited to, betahistine (N-methyl-2-pyridin-2-ylethanamine), ABT-239 (4-(2-{2-[(2R)-2-Methylpyrrolidin-1-yl]ethyl}-benzofuran-5-yl)benzonitrile), Cipralisant(1R,2R)-4-(2-(5,5-dimethylhex-1-ynyl)cyclopropyl)imidazole, Ciproxifan cyclopropyl 4-(3-(1H-imidazol-4-yl)propyloxy) phenyl ketone, Clobenpropit N'-[(4-chlorophenyl)methyl]-1-[3-(3H-imidazol-4-yl)propylthio]formamidine, Thioperamide N-Cyclohexyl-4-(1H-imidazol-4-yl)-1-piperidinecarbothioamide.

The term "anti-H4" refers to any drug that is an antagonist to the H4 receptor. Examples of H4R antagonists include, but are not limited to, thioperamide, JNJ7777120 and JNJ10191584 (Zhang et al Pharmacology and therapeutics, 113 (2007) 594), N-Cyclohexyl-4-(1H-imidazol-4-yl)-1-piperidinecarbothioamide, R-α-methylhistamine. A number of other H4R antagonists are described in a review by Venable et al, (Anti Inflamm. Anti Allergy Agents Med. Chem., 2006, 5 307). None of the antagonists described in the literature are currently used as therapeutic agents.

The term H4R modulated disease includes, but is not limited to immune system diseases, and gastroinstestinal conditions ameliorated by proper histamine management. Examples include GERD; food allergies; Zollinger-Ellison Syndrome; peptic ulcer; dyspepsia; allergic eosinophilic gastroenteritis; mastocytosis with gastrointestinal symptoms; diseases provoked by CD4 Th2 lymphocytes (asthma, rhinitis conjunctivitis eczema, gastro-esophageal reflux disease and other gastric diseases exacerbated by gastric acid), CD4 Th1 lymphocytes (IBD, Crohn's disease, ulcerative colitis and celiac disease and autoimmune gastritis, chronic bronchitis etc.) and/or CD4 Th17 lymphocytes (Uveitis and inflammatory digestive diseases); Chronic Obstructive Pulmonary Disorder (COPD) and other pulmonary types of inflammation including asthma; disease conditions in cancer; and other diseases where histamine or the H4R is involved. H4R agonists may also be used in vaccines as adjuvant to improve immune responses to the inoculated antigens.

The gastrointestinal disease condition may be any of GERD, a food allergy, Zollinger-Ellison Syndrome, peptic ulcer, dyspepsia, allergic eosinophilic gastroenteritis, and mastocytosis with gastrointestinal symptoms.

The term "desirable therapeutic effect" means to treat a subject with the active agents of the invention in order to prevent or ameliorate a disease and/or disease condition.

The terms "therapeutic agent", "drug" and "active agent" are used interchangeably herein and refer to the compounds disclosed herein that affect a H4R modulated disease and/or disease condition. For example, active agents of the invention include, but are not limited to, H4R agonists, H1R antagonists, H2R antagonists, H3R antagonists, LRAs, steroids, NSAIDs.

The terms "pharmaceutical formulations", "pharmaceutical compositions" and "dosage forms" are used interchangeably herein and refer to a composition containing the active ingredient(s) of the invention in a form suitable for administration to a subject.

The term "anticholinergics" or "anticholinergic drugs" refer to compounds that block acetylcholine receptors. Acetylcholine is a chemical produced by the brain that causes muscle contraction, which in turn can constrict airways. Anticholinergics can be use for treatment of COPD.

The term "peak-to-trough ratio" refers to a comparison of the values for a peak (e.g., a high point) plasma level and a trough (e.g., a low point) plasma level of an active agent over a set amount of time. For example, a line graph with plasma levels of a drug with values ranging from 400 ng/ml (peak) to 200 ng/ml (trough) over a four hour period, gives a peak-totrough ratio of 2 for that time. More than one peak-to-trough ratio can be illustrated in a graph.

METHODS OF THE INVENTION

The invention relates to the use of a Tritoqualine (TRQ) (including derivatives or isomers thereof (e.g. Tritoqualine isomers (E1 and E2)) as histamine H4 receptor (H4R) agonists. The invention further relates to the use of H4R agonists to treat diseases and/or disease conditions modulated by H4R agonists.

The invention relates generally to the treatment or amelioration of H4R modulated diseases or conditions with one or more compositions of the invention (e.g., H4R agonists).

In one embodiment, the invention provides methods for the treatment or amelioration of H4R modulated diseases and/or conditions in a subject, comprising administering to the subject an effective amount of a H4R agonist. In a further embodiment, the H4R agonist may not inhibit (or at least not significantly inhibit) Organic Cation Transporter-3 (OCT-3) and/or Serotonin Transporter (SERT).

The invention further provides methods for the treatment or amelioration of H4R modulated diseases or conditions in a subject, comprising administering to the subject an effective amount of a H4R agonist, in combination with one or more other compounds to reach desirable therapeutic effects for H4R modulated diseases. Compounds that can be used in combination with H4R agonists are, for example, other H4R agonists, H1R antagonists (e.g. anti-H1 compounds or drugs), H2R antagonists (e.g. anti-H2 compounds or drugs), H3R antagonists (e.g. anti-H3 compounds or drugs), LRAs and NSAIDs. The method of the invention provides the administration of a single or a combination of H4R agonist drugs.

In one embodiment, the subject is given an effective amount of a H4R agonist(s) and an anti-H1 drug(s). In another embodiment, the subject is given an effective amount of a H4R agonist(s) and an anti-H2 drug(s). In another embodiment, the subject is given an effective amount of a H4R agonist(s) and an anti-H3 drug(s). In yet another embodiment, the subject is given an effective amount of a H4R agonist(s) and one or more of an anti-H1 drug, an anti-H2 drug and an anti-H3 drug. In a further embodiment, the subject may be given an effective amount of a combination of a H4R agonist(s), and any one or more of an anti-H1 drug, an anti-H2 drug and an anti-H3 drug, a LRA, a steroid and NSAID.

The H4R modulated disease and/or condition may be any of GERD, a food allergy, Zollinger-Ellison Syndrome, peptic ulcer, dyspepsia, allergic eosinophilic gastroenteritis, and mastocytosis with gastrointestinal symptoms, diseases provoked by CD4 Th2 lymphocytes (e.g., asthma, rhinitis conjunctivitis eczema, gastro-esophageal reflux disease and other gastric diseases exacerbated by gastric acid), diseases provoked CD4 Th1 lymphocytes (e.g., IBD, Crohn's disease, ulcerative colitis and celiac disease and autoimmune gastritis, chronic bronchitis etc.), diseases provoked CD4 Th17 lymphocytes (e.g., uveitis and inflammatory digestive diseases); Chronic Obstructive Pulmonary Disorder (COPD) and other pulmonary types of inflammation including asthma; disease conditions in cancer; and other diseases where histamine or the H4R is involved. H4R agonists may also be used in vaccines as adjuvant to improve immune responses to inoculated antigens. In a preferred embodiment, the H4R modulated disease or condition is COPD and/or asthma. To treat COPD, a preferred pharmaceutical composition comprises a tritoqualine and an anti-H4 drug such as loratadine. To treat GERD, a preferred pharmaceutical composition comprises a tritoqualine and an anti-H2 drug such as ranitidine. To treat food allergy, a preferred pharmaceutical composition comprises a tritoqualine and an antileukotriene such as Montelukast®. However other compositions of the invention may be used.

The invention also relates to methods of providing a plasma concentration of H4R agonist and/or the other active agent(s) with specific peak-to-trough ratios in a subject. In one embodiment, the peak-to-trough ratio is less than 3.5, over a time period spanning from about 1 hour to about 6, hours after administration to a subject. In another embodiment, the peak-to-trough ratio is less than 3.0, over a time period spanning from about 1 hour to about 6 hours, after administration to a subject. In yet another embodiment, the peak-to-trough ratio is less than 2.5, over a time period spanning from about 1 hour to about 6 hours, after administration to a subject. In a further embodiment, the peak-to-trough ratio is less than 2.0 over a time period spanning from about 1 hour to about 6 hours after administration to a subject.

A dose of a H4R agonist (e.g., Tritoqualine, or an isomer or derivative thereof) administered to a subject may be about 200 mg/day. In another embodiment, the dose of a H4R agonist administered to a subject may be about 1 g/day. In an additional embodiment, the dose of a H4R agonist administered to a subject may be about 2 g/day. In yet another embodiment, the dose of a H4R agonist administered to a subject may be about 3 g/day. In a further embodiment, the dose of a H4R agonist administered to a subject may be about 1-5 mg/day, about 5-10 mg/day, about 10-15 mg/day, about 15-20 mg/day, about 20-25 mg/day, about 25-30 mg/day, about 30-35 mg/day, about 35-40 mg/day, about 40-45 mg/day, about 45-50 mg/day, about 50-55 mg/day, about 55-60 mg/day, about 60-65 mg/day, about 65-70 mg/day, about 70-75 mg/day, about 75-80 mg/day, about 80-85 mg/day, about 85-90 mg/day, about 90-95 mg/day, about 95-100 mg day, about 100-105 mg/day, about 105-110 mg/day, about 110-115 mg/day, about 115-120 mg/day, about 120-125 mg/day, about 125-130 mg/day, about 130-135 mg/day, about 135-140 mg/day, about 140-145 mg/day, about 145-150 mg/day, about 150-155 mg/day, about 155-160 mg/day, about 160-165 mg/day, about 165-170 mg/day, about 170-175 mg/day, about 175-180 mg/day, about 180-185 mg/day, about 185-190 mg/day, about 190-195 mg/day, about 195-200 mg/day, about 200-205 mg/day, about 205-210 mg/day, about 210-215 mg/day, about 215-220 mg/day, about 220-225 mg/day, about 225-230 mg/day, about 230-235 mg/day, about 235-240 mg/day, about 240-245 mg/day, about 245-250 mg/day, about 250-255 mg/day, about 255-260 mg/day, about 260-265 mg/day, about 265-270 mg/day, about 270-275 mg/day, about 275-280 mg/day, about 280-285 mg/day, about 285-290 mg/day, about 290-295 mg/day, about 295-300 mg/day, about 300-305 mg/day, about 305-310 mg/day, about 310-315 mg/day, about 315-320 mg/day, about 320-325 mg/day, about 325-330 mg/day, about 330-335 mg/day, about 335-340 mg/day, about 340-345 mg/day, about 345-350 mg/day, about 350-355 mg/day, about 355-360 mg/day, about 360-365 mg/day, about 365-370 mg/day, about 370-375 mg/day, about 375-380 mg/day, about 380-385 mg/day, about 385-390 mg/day, about 390-395 mg/day, about 395-400 mg/day, about 400-405 mg/day, about 405-410 mg/day, about 410-415 mg/day, about 415-420 mg/day, about 420-425 mg/day, about 425-430 mg/day, about 430-435 mg/day, about 435-440 mg/day, about 440-445 mg/day, about 445-450 mg/day, about 1 mg/day-1 g/day, about 1 mg/day-2 g/day or about 1 mg/day-3 g/day.

Suitable examples of H4R agonists include, but are not limited to, any of Tritoqualine includes an isomer or derivative thereof, 4-methylhistmime (4MeHA) and clobenprobit (CB).

Tritoqualine maybe used successfully alone and in combinatorial therapy to treat allergy, GERD, food allergy, and COPD. The drug has two chiral centers and therefore, it exists in four isomeric forms. The commercial product includes a mixture of two isomers, one with the chiral centers at the SS configuration and the other one at the RR configuration. Examples of Tritoqualine isomers include, but are not limited to, E1 and E2 enantiomers.

Surprisingly, Tritoqualine and each of its isomers may have different activity as an H4R agonist i.e., various H4R agonists will have varying effects on H4R. Thus, binding of various H4R agonists to the H4R can provide varying therapeutic profiles (e.g., cytokine activation profiles) in a subject.

In accordance with the practice of the invention, suitable examples of Leukotriene Receptor Antagonists (LRA) include, but are not limited to, Montelukast® (Singulair®), Pranlukast® and Zafirlukas®. The method provides the administration of a single or a combination of LRA drugs.

The dose of LRAs (e.g. Montelukast® (Singulair®)) administered to a subject may be about 10.0 mg/day. In another embodiment, the dose of a LRA(s) (e.g. Montelukast®) administered to a subject may be about 0.1 to 1.0 mg/day, about 1.0 to 2.0 mg/day, about 2.0 to 3.0 mg/day, about 3.0 to 4.0 mg/day, about 4.0 to 5.0 mg/day, about 5.0 to 6.0 mg/day, about 6.0 to 7.0 mg/day, about 7.0 to 8.0 mg/day, about 8.0 to 9.0 mg/day, about 9.0 to 10.0 mg/day, about 10.0 to 11.0 mg/day, about 11.0 to 12.0 mg/day, about 12.0 to 13.0 mg/day, about 13.0 to 14.0 mg/day, about 14.0 to 15.0 mg/day, about 15.0 to 16.0 mg/day, about 16.0 to 17.0 mg/day, about 17.0 to 18.0 mg/day, about 18.0 to 19.0 mg/day, about 19.0 to 20.0 mg/day, about 20.0 to 21.0 mg/day, about 21.0 to 22.0 mg/day, about 22.0 to 23.0 mg/day, about 23.0 to 24.0 mg/day, about 24.0 to 25.0 mg/day, about 25.0 to 26.0 mg/day, about 26.0 to 27.0 mg/day, about 27.0 to 28.0 mg/day, about 28.0 to 29.0 mg/day, about 29.0 to 30.0 mg/day, about 30.0 to 31.0 mg/day, about 31.0 to 32.0 mg/day, about 32.0 to 33.0 mg/day, about 33.0 to 34.0 mg/day, about 34.0 to 35.0 mg/day or about 1 mg/day to 35 mg/day.

In accordance with the practice of the invention, suitable examples of anti-H1 drugs includes, but are limited to, any of brompheniramine, cetirizine, fexofenadine, cyproheptadine, dexchlorpheniramine, hydroxizine, ketotifen, loratadine, mequitazine, oxotomide, mizolastine, ebastine, astemizole, carbinoxamide, alimemazine, buclizine, cyclizine hydrochloride, doxylamine, mepyramine, antazoline, diphenhydramine, carbinoxamine, clemastine, dimenhydrinate, pheniramine, chlorphenamine, triprolidine, chlorcyclizine, hydroxyzine, meclizine, promethazine, and azatadine or analogs, equivalents, isomers, pharmaceutically acceptable salts, and solvate forms thereof. The method provides the administration of a single or a combination of anti-H1 drugs.

The dose of an anti-H1 drug (e.g., loratadine) administered to a subject may be about 10.0 mg/day. In another embodiment, the dose of the anti-H1 drug(s) (e.g. loratadine) administered to a subject may be about 0.1 to 1.0 mg/day, about 1.0 to 2.0 mg/day, about 2.0 to 3.0 mg/day, about 3.0 to 4.0 mg/day, about 4.0 to 5.0 mg/day, about 5.0 to 6.0 mg/day, about 6.0 to 7.0 mg/day, about 7.0 to 8.0 mg/day, about 8.0 to 9.0 mg/day, about 9.0 to 10.0 mg/day, about 10.0 to 11.0 mg/day, about 11.0 to 12.0 mg/day, about 12.0 to 13.0 mg/day, about 13.0 to 14.0 mg/day, about 14.0 to 15.0 mg/day, about 15.0 to 16.0 mg/day, about 16.0 to 17.0 mg/day, about 17.0 to 18.0 mg/day, about 18.0 to 19.0 mg/day, about 19.0 to 20.0 mg/day, about 20.0 to 21.0 mg/day, about 21.0 to 22.0 mg/day, about 22.0 to 23.0 mg/day, about 23.0 to 24.0 mg/day, about 24.0 to 25.0 mg/day, about 25.0 to 26.0 mg/day, about 26.0 to 27.0 mg/day, about 27.0 to 28.0 mg/day, about 28.0 to 29.0 mg/day, about 29.0 to 30.0 mg/day, about 30.0 to 31.0 mg/day, about 31.0 to 32.0 mg/day, about 32.0 to 33.0 mg/day, about 33.0 to 34.0 mg/day, about 34.0 to 35.0 mg/day or about 1 mg/day to about 35 mg/day.

Also, the dose of an anti-H1 drug (e.g., cetirizine) administered to a subject may be about 10 mg/day. In another embodiment, the dose of the anti-H1 drug(s) (e.g. cetirizine) administered to a subject may be about 0.1 to 0.5 mg/day, about 0.5 to 1.0 mg/day, about 1.0 to 1.5 mg/day, about 1.5 to 2.0 mg/day, about 2.0 to 2.5 mg/day, about 2.5 to 3.0 mg/day, about 3.0 to 3.5 mg/day, about 3.5 to 4.0 mg/day, about 4.0 to 4.5 mg/day, about 4.5 to 5.0 mg/day, about 5.0 to 5.5 mg/day, about 5.5 to 6.0 mg/day, about 6.0 to 6.5 mg/day, about 6.5 to 7.0 mg/day, about 7.0 to 7.5 mg/day, about 7.5 to 8.0 mg/day, about 8.5 to 9.0 mg/day, about 9.0 to 9.5 mg/day, about 9.5 to 10.0 mg/day, about 10.5 to 11.0 mg/day, about 11.0 to 11.5 mg/day, about 11.5 to 12.0 mg/day, about 12.0 to 12.5 mg/day, about 12.5 to 13.0 mg/day, about 13.0 to 13.5 mg/day, about 13.5 to 14.0 mg/day, about 14.0 to 14.5 mg/day, about 14.5 to 15.0 mg/day, about 15.0 to 15.5 mg/day, about 15.5 to 16.0 mg/day, about 16.0 to 16.5 mg/day, about 16.5 to 17.0 mg/day, about 17.0 to 17.5 mg/day, about 17.5 to 18.0 mg/day, about 18.5 to 19.0 mg/day, about 19.0 to 19.5 mg/day, about 19.5 to 20.0 mg/day, about 20.5 to 21.0 mg/day, about 21.0 to 21.5 mg/day, about 21.5 to 22.0 mg/day, about 22.0 to 22.5 mg/day, about 22.5 to 23.0 mg/day, about 23.0 to 23.5 mg/day, about 23.5 to 24.0 mg/day, about 24.0 to 24.5 mg/day, about 24.5 to 25.0 mg/day, about 25.0 to 25.5 mg/day, about 25.5 to 26.0 mg/day, about 26.0 to 26.5 mg/day, about 26.5 to 27.0 mg/day, about 27.0 to 27.5 mg/day, about 27.5 to 28.0 mg/day, about 28.5 to 29.0 mg/day, about 29.0 to 29.5 mg/day, about 29.5 to 30.0 mg/day or about 0.5 mg/day to 30.0 mg/day.

Further, the dose of an anti-H1 drug (e.g., fexofenadine) administered to a subject may be about 120.0 mg/day. In another embodiment, the dose of the anti-H1 drug(s) (e.g. fexofenadine) administered to a subject may be about 1.0 to 30.0 mg/day, about 30.0 to 50.0 mg/day, about 50.0 to about 70.0 mg/day, about 70.0 to 90.0 mg/day, about 90.0 to 110.0 mg/day, about 110.0 to 130.0 mg/day, about 130.0 to 150.0 mg/day, about 150.0 to 170.0 mg/day, about 170.0 to 190.0 mg/day, about 190.0 to 210.0 mg/day, about 210.0 to 230.0 mg/day, about 230.0 to 250.0 mg/day, about 250.0 to 270.0 mg/day, about 270.0 to 290.0 mg/day, about 290.0 to 310.0 mg/day, about 310.0 to 330.0 mg/day, about 330.0 to 350.0 mg/day, about 350.0 to 370.0 mg/day, about 370.0 to 390.0 mg/day, about 390.0 to 410.0 mg/day, about 410.0 to 430.0 mg/day, about 430.0 to 450.0 mg/day, about 450.0 to 470.0 mg/day, about 470.0 to 490.0 mg/day, about 490.0 to 510.0 mg/day or about 1 mg/day to 510 mg/day.

Suitable examples of anti-H2 drugs include, but are not limited to, any of ranitidine, cimetidine, famotidine, and nizatidine and/or analogs, equivalents, isomers, pharmaceutically acceptable salts, and solvate forms thereof. The method provides the administration of a single or combination of anti-H2 drugs.

The dose of an anti-H2 drug (e.g., ranitidine) administered to a subject may be about 150 mg/day. In another embodiment, the dose of the anti-H2 drug(s) (e.g. ranitidine) administered to a subject may be about 1.0 to 20.0 mg/ml, about 20.0 to 40.0 mg/ml, about 40.0 to 60.0 mg/ml, about 60.0 to 80.0 mg/ml, about 80.0 to 100.0 mg/ml, about 100.0 to 120.0 mg/ml, about 120.0 to 140.0 mg/ml, about 140.0 to 160.0 mg/ml, about 160.0 to 180.0 mg/ml, about 180.0 to 200.0 mg/ml, about 200.0 to 220.0 mg/ml, about 220.0 to 240.0 mg/ml, about 240.0 to 260.0 mg/ml, about 260.0 to 280.0 mg/ml, about 280.0 to 300.0 mg/ml, about 300.0 to 320.0 mg/ml, about 320.0 to 340.0 mg/ml, about 340.0 to 360.0 mg/ml, about 360.0 to 380.0 mg/ml, about 380.0 to 400.0 mg/ml, about 400.0 to 420.0 mg/ml, about 420.0 to 440.0 mg/ml, about 440.0 to 460.0 mg/ml, about 460.0 to 480.0 mg/ml, about 480.0 to 500.0 mg/ml, about 500.0 to 520.0 mg/ml, about 520.0 to 540.0 mg/ml, about 540.0 to 560.0 mg/ml, about 560.0 to 580.0 mg/ml, about 580.0 to 600.0 mg/ml, about 600.0 to 620.0 mg/ml, about 620.0 to 640.0 mg/ml, about 640.0 to 660.0 mg/ml, about 660.0 to 680.0 mg/ml, about 680.0 to 700.0 mg/ml, about 700.0 to 720.0 mg/ml, about 720.0 to 740.0 mg/ml, about 740.0 to 760.0 mg/ml, about 760.0 to 780.0 mg/ml, about 780.0 to 800.0 mg/ml, about 800.0 to 820.0 mg/ml, about 820.0 to 840.0 mg/ml, about 840.0 to 860.0 mg/ml, about 860.0 to 880.0 mg/ml, about 880.0 to 900.0 mg/ml or about 1 mg/ml to about 900 mg/ml.

Suitable examples of anti-H3 drugs include, but are not limited to, any of betahistine (N-methyl-2-pyridin-2-yletha-namine), ABT-239 (4-(2-{2-[(2R)-2-Methylpyrrolidin-1-yl]ethyl}-benzofuran-5-yl)benzonitrile), Cipralisant(1R,2R)-4-(2-(5,5-dimethylhex-1-ynyl)cyclopropyl)imidazole, Ciproxifan cyclopropyl 4-(3-(1H-imidazol-4-yl)propyloxy) phenyl ketone, Clobenpropit N'-[(4-chlorophenyl)methyl]-1-[3-(3H-imidazol-4-yl)propylthio]formamidine, Thioperamide N-Cyclohexyl-4-(1H-imidazol-4-yl)-1-piperidinecarbothioamide. The method provides the administration of a single or combination of anti-H3 drugs.

The dose of an anti-H3 drug administered to a subject may be about 0.1 to 1.0 mg/day, about 1.0 to 2.0 mg/day, about 2.0 to 3.0 mg/day, about 3.0 to 4.0 mg/day, about 4.0 to 5.0 mg/day, about 5.0 to 6.0 mg/day, about 6.0 to 7.0 mg/day, about 7.0 to 8.0 mg/day, about 8.0 to 9.0 mg/day, about 9.0 to 10.0 mg/day, about 10.0 to 15.0 mg/day, about 15.0 to 20.0 mg/day, about 20.0 to 25.0 mg/day, about 25.0 to 30.0 mg/day, about 30.0 to 35.0 mg/day, about 35.0 to 40.0 mg/day, about 45.0 to 50.0 mg/day, about 50.0 to 60.0 mg/day, about 60.0 to 70.0 mg/day, about 70.0 to 80.0 mg/day, about 80.0 to 90.0 mg/day, about 90.0 to 100.0 mg/day, about 100.0 to 150.0 mg/day, about 150.0 to 200.0 mg/day, about 200.0 to 250.0 mg/day, about 250.0 to 300.0 mg/day, about 300.0 to 350.0 mg/day, about 350.0 to 400.0 mg/day, about 400.0 to 450.0 mg/day, about 450.0 to 500.0 mg/day, about 500.0 to 550.0 mg/day, about 550.0 to 600.0 mg/day, about 600.0 to 650.0 mg/day, about 650.0 to 700.0 mg/day, about 700.0 to 750.0 mg/day, about 750.0 to 800.0 mg/day, about 800.0 to 850.0 mg/day, about 850.0 to 900.0 mg/day, about 900.0 to 950.0 mg/day, about 950.0 to 1000.0 mg/day, about 1000.0 to 1100.0 mg/day, about 1100.0 to 1200.0 mg/day, about 1200.0 to 1300.0 mg/day, about 1300.0 to 1400.0 mg/day, about 1400.0 to 1500.0 mg/day, about 1500.0 to 1600.0 mg/day, about 1600.0 to 1700.0 mg/day, about 1800.0 to 1900.0 mg/day or about 1900.0 to 2000.0 mg/day.

The invention further relates to the treatment or prevention of COPD using drug combinations comprising a H4R agonist, an anti-H1 drug and an anticholinergic drug.

In one embodiment of the invention, the invention provides methods for the treatment of COPD comprising administering to a subject an effective amount of a H4R agonist, an anti-H1 drug and an anticholinergic drug. Suitable H4R agonists and anti-H1 drugs are described above. Suitable examples of anticholinergics include, but are not limited to: tiotropium bromide (Spiriva®) and ipratropium bromide (Atrovent®).

The dose of an anticholinergic drug administered to a subject may be about 0.1 to 1.0 mg/day, about 1.0 to 2.0 mg/day, about 2.0 to 3.0 mg/day, about 3.0 to 4.0 mg/day, about 4.0 to 5.0 mg/day, about 5.0 to 6.0 mg/day, about 6.0 to 7.0 mg/day, about 7.0 to 8.0 mg/day, about 8.0 to 9.0 mg/day, about 9.0 to 10.0 mg/day, about 10.0 to 15.0 mg/day, about 15.0 to 20.0 mg/day, about 20.0 to 25.0 mg/day, about 25.0 to 30.0 mg/day, about 30.0 to 35.0 mg/day, about 35.0 to 40.0 mg/day, about 45.0 to 50.0 mg/day, about 50.0 to 60.0 mg/day, about 60.0 to 70.0 mg/day, about 70.0 to 80.0 mg/day, about 80.0 to 90.0 mg/day, about 90.0 to 100.0 mg/day, about 100.0 to 150.0 mg/day, about 150.0 to 200.0 mg/day, about 200.0 to 250.0 mg/day, about 250.0 to 300.0 mg/day, about 300.0 to 350.0 mg/day, about 350.0 to 400.0 mg/day, about 400.0 to 450.0 mg/day, about 450.0 to 500.0 mg/day, about 500.0 to 550.0 mg/day, about 550.0 to 600.0 mg/day, about 600.0 to 650.0 mg/day, about 650.0 to 700.0 mg/day, about 700.0 to 750.0 mg/day, about 750.0 to 800.0 mg/day, about 800.0 to 850.0 mg/day, about 850.0 to 900.0 mg/day, about 900.0 to 950.0 mg/day, about 950.0 to 1000.0 mg/day or about 1000.0. The dose of an anticholinergic drug dispensed by an inhaler to a subject may be about 0.1 mg per puff, about 0.5 mg per puff, about 1.0 mg per puff, about 2.5 mg per puff, about 5.0 mg per puff, about 10.0 mg per puff, about 15.0 mg per puff, about 18.0 mg per puff, about 20.0 mg per puff, about 25.0 mg per puff, about 30.0 mg per puff, about 35.0 mg per puff, about 40.0 mg per puff, about 45.0 mg per puff or about 50.0 mg per puff.

In a specific embodiment of the invention, the H4R agonist is tritoqualine, the anti-H1 drug is loratadine and the anticholinergic drug is Spiriva®.

In a further embodiment of the invention, the drug combination can further comprise any one or more of existing COPD therapies including but not limited to combination inhaler, steroids, inhaled beta-2 agonists, inhaled corticosteroids, mucolytics, oral beta-2 agonists and theophyllines.

According to the practice of the invention, suitable examples of steroids include, but are not limited to, corticosteroids, Cortisone, Hydrocortisone/cortisol, Desoxycortone, Alclometasone, Aldosterone, Amcinonide, Beclometasone, Betamethasone, Budesonide, Ciclesonide, Clobetasol, Clobetasone, Clocortolone, Cloprednol, Cortivazol, Deflazacort, Deoxycorticosterone, Desonide, Desoximetasone, Dexamethasone, Diflorasone, Diflucortolone, Difluprednate, Fluclorolone, Fludrocortisone, Fludroxycortide, Flumetasone, Flunisolide, Fluocinolone acetonide, Fluocinonide, Fluocortin, Fluocortolone, Fluorometholone, Fluperolone, Fluprednidene, Fluticasone, Formocortal, Halcinonide, Halometasone, Hydrocortisone aceponate, Hydrocortisone buteprate, Hydrocortisone butyrate, Loteprednol, Medrysone, Meprednisone, Methylprednisolone, Methylprednisolone aceponate, Mometasone furoate, Paramethasone, Prednicarbate, Prednisone, Prednisolone, Prednylidene, Rimexolone, Tixocortol, Triamcinolone and Ulobetasol. The method provides the administration of a single or combination of steroid drugs.

Suitable examples of NSAIDs include, but are not limited to, acetyl salicylic acid (Aspirin), Amoxiprin, Benorilate, choline magnesium salicylate, diflunisal, Faislamine, Methyl salicylate, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, meloxicam, tramadol, Aceclofenac, Acemetacin, Bromfenac, Etodolac, Indometacin, Nabumetone, Sulindac, Tolmetin, Ibuprofen, Carprofen, Fenbufen, Loxoprofen, Oxaprozin, Tiaprofenic acid, Suprofen, Mefenamic acid, Meclofenamicacid, Phenylbutazone, Azapropazone, Metamizole, Oxyphenbutazone, Sulfinpyrazone, Meloxicam, Piroxicam, Lornoxicam and Tenoxicam. In a preferred embodiment, NSAIDs include Aspirin, Meloxicam, Ibuprofen, Naproxen. The method provides the administration of a single or combination of NSAIDS.

In accordance with the practice of the invention, for each given daily dose of a drug, or combination of drugs, listed above, the given dose may be administered once a day or multiple times a day. For example, ½ of the given dose may be administered twice a day. In another embodiment of the invention, ⅓ of the given dose may be administered 3 times a day. In a further embodiment of the invention, ¼ of the given dose may be administered 4 times a day. In yet another embodiment of the invention, ⅕ of the given dose may be administered 5 times a day. In yet another embodiment of the invention, ⅙ of the given dose may be administered 6 times a day. In yet another embodiment of the invention, ⅐ of the given dose may be administered times a day. In yet another embodiment of the invention, ⅛ of the given dose may be is administered 8 times a day. In yet another embodiment of the invention, ⅑ of the given dose may be administered 9 times a day. In yet another embodiment of the invention, ¹⁄₁₀ of the given dose may be administered 10 times a day.

Additionally, for each given daily dose of a drug listed above, various fractions of the given dose may be administered to the subject at multiple times during the day, with the sum of the various fractions adding up to the given dose. For example, the amount of the fraction of the given dose administered to the subject at a given time may be any of ½ of the given dose, ⅓ of the given dose, ¼ of the given dose, ⅕ of the given dose, ⅙ of the given dose, ⅐ of the given dose, ⅛ of the given dose, ⅑ of the given dose, or ¹⁄₁₀ of the given dose. In another embodiment of the invention, the fraction of the given dose that is administered, and the total number of times the drug is administered can vary by day. In a further embodiment of the invention, the time of day the given dose or fraction of the given dose is administered can vary by day.

For example, a daily dose of a drug (e.g., H4R agonist) can total about 200 mg per day. The drug can be given once a day at a dose of about 200 mg, twice a day with each dose about 100 mg, three times a day with each dose about 66.6 mg or four times a day with each dose about 50 mg.

In accordance with the practice of the invention, the drug can be administered one or more times a day, daily, weekly, monthly or yearly.

Dosage of the therapeutic agent(s) of the invention is dependant upon many factors including, but not limited to, the type of tissue affected, the type of disease being treated, the severity of the disease, a subject's health and response to the treatment with the agents. Accordingly, dosages of the agents can vary depending on each subject and the mode of administration.

In accordance with the practice of the invention, the subject may be a mammal. In other embodiments of the invention, the subject may be any of human, monkey, ape, dog, cat, cow, horse, sheep, rabbit, mouse, or rat.

In accordance with the practice of the invention, the administration of a given drug may be effected locally or systemically. Additionally, the route of administration of a given drug may be any of topical, enteral or parenteral. In other embodiments of the invention, the route of administration of a given drug may be any of rectal, intercisternal, bucal, intramuscular, intrasternal, intracutaneous, intrasynovial, intravenous, intraperitoneal, intraocular, periostal, intra-articular injection, infusion, oral, inhalation, subcutaneous, implantable pump, continuous infusion, gene therapy, intranasal, intrathecal, intracerebroventricular, transdermal, or by spray, patch or injection.

In accord with the practice of the invention, the route of administration of a given drug can vary during a course of treatment, or during a given day. For example, if a given drug is administered in conjunction with one or more additional drugs, each additional drug may be administered by identical or different routes compared to the other drugs.

The combination of a H4R agonist alone, or in combination with one or more of an anti-H1 drug, anti-H2 drug, anti-H3 drug, a LRA drug, a steroid and a NSAID, can be prepared in a single or multiple dosage form for administration to a subject.

The administration of a given drug to a subject can be performed daily, weekly, monthly, every other month, quarterly, or any other schedule of administration as a single dose administration, in multiple doses, or in continuous dose form. Additionally, a given drug can be administered to a subject intermittently, or at a gradual, continuous, constant, immediate or controlled rate to a subject.

In accord with the practice of the invention, if other drugs are being administered in addition to the agents of the invention, the timing of administration of each drug may be identical to or different from the timing of the other drugs. The administration of the drugs of the invention can be concurrent or at different times.

The active agents of the invention may be administered alone or in combination with other therapeutic agents. Components of the combinations may be administered either concomitantly, (e.g., as an admixture), separately but simultaneously or concurrently or sequentially. This includes presentations in which the combined active agents are administered together as a therapeutic mixture, and also procedures in which the combined active agents are administered separately but simultaneously, e.g., as through separate intravenous lines into the same individual. Administration "in combination" further includes the separate administration of one of the active agents given first, followed by the one or more sequential active agent(s).

In accordance with the practice of the invention, the subject being administered an active agent may have any one or more of the following diseases and/or conditions: GERD; food allergies; Zollinger-Ellison Syndrome; peptic ulcer; dyspepsia; allergic eosinophilic gastroenteritis; mastocytosis with gastrointestinal symptoms; those provoked by CD4 Th2 lymphocytes (asthma, rhinitis conjunctivitis eczema, gastroesophageal reflux disease and other gastric diseases exacerbated by gastric acid), CD4 Th1 lymphocytes (IBD, Crohn's disease, ulcerative colitis and celiac disease and autoimmune gastritis, chronic bronchitis etc.), CD4 Th17 lymphocytes (Uveitis and inflammatory digestive diseases); COPD and other pulmonary types of inflammation including asthma; disease conditions in cancer; and other diseases where histamine or the H4R is involved. H4R agonists may also be used in vaccines as adjuvant to improve immune responses to the inoculated antigens.

The invention provides methods for the treatment or prevention of gastrointestinal disease conditions ameliorated by histamine management in a subject, comprising administering to the subject an effective amount of a histidine decarboxylase inhibitor. In one embodiment, the subject is given an effective amount of a histamine decarboxylase inhibitor and an anti-H1 drug. In another embodiment, the subject is given an effective amount of a histidine decarboxylase inhibitor and an anti-H2 drug. In yet another embodiment, the subject is given an effective amount of a histidine decarboxylase inhibitor, an anti-H1 drug and an anti-H2 drug. In a further embodiment, the subject may be given an effective amount of a combination of a histidine decarboxylase inhibitor, and any one or both an anti-H1 drug and an anti-H2 drug together with an NSAID.

An embodiment of the invention also provides methods for the treatment or prevention of gastrointestinal disease conditions ameliorated by histamine management in a subject comprising administering to the subject an effective amount of a HDC inhibitor in combination with an effective amount a LRA. In a further embodiment, the subject is given an effective amount of a HDC inhibitor in combination with an effective amount of a LRA and an effective amount of an anti-H1 drug. In another embodiment of the invention, the subject is given an effective amount of a HDC inhibitor in combination with an effective amount of a LRA and an effective amount of an anti-H2 drug. In a further embodiment of the invention, the subject is given an effective amount of a HDC inhibitor in combination with an effective amount of a LRA, an effective amount of an anti-H1 drug and an effective amount of an anti-H2 drug.

The invention further provides methods for treatment or prevention of COPD comprising administering to the subject an effective amount of HDC inhibitor. In one embodiment, the patient is administered an effective amount of a HDC inhibitor in combination with an effective amount of an anti-H1 drug. Histidine decarboxylase inhibitors in general, as well as histamine receptor antagonists e.g. Anti-H1 drugs have never been used for the treatment of COPD. Tritoqualine (an HDC inhibitor) and Loratadine (an anti-H1 drug) were traditionally used for the treatment of allergy and primarily allergic rhinitis. The combination of Tritoqualine and Loratadine showed statistically significant effectiveness in the management of COPD when compared with the standard treatment of beta agonists, bronchodilators, steroids and oxygen. The presumed action of combining Tritoqualine and an anti-H1 drug may be by increasing the TH1 cells thus balancing the equilibrium between TH1 and TH2 cells to the detriment of TH2 cells. As a result, secretion of inflammatory cytokines such as IL4, IL5, and IL10 is reduced causing less pulmonary inflammation.

In another embodiment of the invention the patient is given HDC inhibitor in combination with any one or more of COPD therapies including but not limited to Anticholinergics, Combination Inhaler, Corticosteroids, Inhaled Beta-2 Agonists, Inhaled Corticosteroids, Mucolytics, Oral Beta-2 Agonists, Bronchodilators and Theophyllines. In a further embodiment, the patient is given HDC inhibitor and anti-H1 drug in combination with any one or more of COPD therapies including but not limited to Anticholinergics, Combination Inhaler, Corticosteroids, Inhaled Beta-2 Agonists, Inhaled Corticosteroids, Mucolytics, Oral Beta-2 Agonists, Bronchodilators and Theophyllines. In yet another embodiment of the invention, the patient is administered an effective amount of a HDC inhibitor, an anti-H1 drug and a NSAID.

Suitable examples of histidine decarboxylase inhibitors include, but are not limited to, any of Tritoqualine or an isomer thereof, alpha-fluoromethylhistidine, 3-methoxy-5,7,3',4'-tetrahydroxyflavan, naringenin, (+)-cyanidanol-3, the dipeptide His-Phe, and 4-imidazolyl-3-amino-2-butanone, polyphenols such as catechins and related structures; these include, but are not limited to: (−)-epigallocatechin gallate, (−)-epicatechin gallate, (−)-epicatechin, (−)-epigallocatechin, and is composed of (−)-epicatechin, (−)-epigallocatechin; and other flavonoids such as O-methyl-3(+)catechin; or analogs, equivalents, isomers, pharmaceutically acceptable salts, and solvate forms of any of the above. The Tritoqualine isomer may be an SS isomer of Tritoqualine or an RR isomer of Tritoqualine. The method provides the administration of single or a combination of histidine decarboxylase inhibitors.

In accordance with the practice of the invention, the subject may have any one or more of the following: 1) a history of GERD; 2) a history of allergies (for example food allergies); 3) a history of COPD; 4) previous unsatisfactory treatment with an anti-H1 and/or anti-H2 drug; 5) previously unsatisfactory treatment with existing COPD therapies; 6) previous unsatisfactory treatment with proton pump inhibitors (PPI); 7) previous diagnosis of GERD and concurrent symptoms of allergy; and/or 8) previous unsatisfactory treatment with cromoglycate.

In one embodiment, the subject may suffer from COPD or GERD (or any of the gastrointestinal disorders or diseases disclosed herein) but does not exhibit allergy symptoms which include any one or more of allergic asthma, allergic conjunctivitis, and allergic rhinitis.

For example, the allergy may be confirmed with two positive prick tests for the same allergen or set of allergens. The allergens may be any of Dermatophagoid Ptermonysisnus, Demathophagoid Farinae, cat dander, dog dander, food allergens, fungal proteins, and pollen proteins. Additionally, the food allergen may be any of wheat, egg, soy, potato, peanut, and/or tomato proteins. The fungal protein may be any of a protein from a species in the *alternaria* genus, a protein from a species in the *mucor* genus, and a protein from a species in the *aspergillus* genus. The pollen protein may be any of pollen of birch tree, pollen of cypress tree, pollen of Quercus tree, pollen of lolium perenne, and pollen of ray grass.

COMPOSITIONS OF THE INVENTION

The present invention provides pharmaceutical formulations (also known as pharmaceutical compositions or dosage forms) comprising a first active agent (e.g., a H4R agonist), one or more additional active agent (e.g., a H1R antagonist, a H2R antagonist, a H3R antagonist, a LRA, a steroid, a NSAID or other active agent), and a pharmaceutically acceptable carrier or vehicle.

The present invention also provides pharmaceutical formulations for the treatment of COPD comprising a first active agent (e.g., a H4R agonist), a second active agent (e.g., a H1R antagonist), a third active agent (e.g., an anticholinergic drug) and a pharmaceutically acceptable carrier or vehicle.

Pharmaceutically acceptable carrier or vehicle refers to a non-toxic solid, semisolid (also referred to herein as softgel) or liquid filler, diluent, encapsulating material or formulation auxiliary of any type. The invention also provides methods for treating or ameliorating H4R modulated diseases using said pharmaceutical formulations.

H4R agonists include, but are not limited to, Tritoqualine or an isomer thereof, 4-methylhistmime (4MeHA) and clobenprobit (CB). The pharmaceutical formulation of the invention provides one or more H4R agonist drugs. Examples of Tritoqualine isomers include, but are not limited to, the E1 and E2 enantiomer.

H1 antagonists (anti-H1 drugs) include, but are not limited to, brompheniramine, cetirizine, levocetirizine, fexofenadine, cyproheptadine, dexchlorpheniramine, hydroxizine, ketotifen, loratadine, mequitazine, oxotomide, mizolastine, ebastine, astemizole, carbinoxamide, alimemazine, buclizine, cyclizine hydrochloride, doxylamine, mepyramine, antazoline, diphenhydramine, carbinoxamine, clemastine, dimenhydrinate, pheniramine, chlorphenamine, triprolidine, chlorcyclizine, hydroxyzine, meclizine, promethazine and azatadine and/or analogs, equivalents, isomers, salts, and solvate forms thereof. The pharmaceutical formulation of the invention provides one or more anti-H1 drugs.

H2 antagonists (anti-H2 drugs) include, but are not limited to, ranitidine, cimetidine, famotidine, and nizatidine and/or analogs, equivalents, isomers, salts, and solvate forms thereof. The pharmaceutical formulation of the invention provides one or more anti-H2 drugs.

H3 antagonists (anti-H3 drugs) include, but are not limited to, betahistine (N-methyl-2-pyridin-2-ylethanamine), ABT-239 (4-(2-{2-[(2R)-2-Methylpyrrolidin-1-yl]ethyl}-benzofuran-5-yl)benzonitrile), Cipralisant(1R,2R)-4-(2-(5,5-dimethylhex-1-ynyl)cyclopropyl)imidazole, Ciproxifan cyclopropyl 4-(3-(1H-imidazol-4-yl)propyloxy)phenyl ketone, Clobenpropit N-[(4-chlorophenyl)methyl]-1-[3-(3H-imidazol-4-yl)propylthio]formamidine, Thioperamide N-Cyclohexyl-4-(1H-imidazol-4-yl)-1-piperidinecarbothioamide. The pharmaceutical formulation of the invention provides one or more anti-H3 drugs.

Anticholinergic drugs include, but are not limited to: tiotropium bromide (Spiriva®) and ipratropium bromide (Atrovent®).

LRAs include, but are not limited to, Montelukast® (Singulair®), Pranlukast® and Zafirlukast®. The method provides the administration of a single or a combination of LRAs.

Steroids include, but are not limited to, corticosteroids, Aldosterone, Cortisone, Hydrocortisone/cortisol, Desoxycortone, Alclometasone, Amcinonide, Beclometasone, Betamethasone, Budesonide, Ciclesonide, Clobetasol, Clobetasone, Clocortolone, Cloprednol, Cortivazol, Deflazacort, Deoxycorticosterone, Desonide, Desoximetasone, Dexamethasone, Diflorasone, Diflucortolone, Difluprednate, Fluclorolone, Fludrocortisone, Fludroxycortide, Flumetasone, Flunisolide, Fluocinolone acetonide, Fluocinonide, Fluocortin, Fluocortolone, Fluorometholone, Fluperolone, Fluprednidene, Fluticasone, Formocortal, Halcinonide, Halometasone, Hydrocortisone aceponate, Hydrocortisone buteprate, Hydrocortisone butyrate, Loteprednol, Medrysone, Meprednisone, Methylprednisolone, Methylprednisolone aceponate, Mometasone furoate, Paramethasone, Prednicarbate, Prednisone, Prednisolone, Prednylidene, Rimexolone, Tixocortol, Triamcinolone and Ulobetasol. The method provides the administration of a single or combination of steroid drugs.

NSAIDs include, but are not limited to, acetyl salicylic acid (Aspirin), Amoxiprin, Benorilate, choline magnesium salicylate, diflunisal, Faislamine, Methyl salicylate, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, meloxicam, tramadol, Aceclofenac, Acemetacin, Bromfenac, Etodolac, Indometacin, Nabumetone, Sulindac, Tolmetin, Ibuprofen, Carprofen, Fenbufen, Loxoprofen, Oxaprozin, Tiaprofenic acid, Suprofen, Mefenamic acid, Meclofenamicacid, Phenylbutazone, Azapropazone, Metamizole, Oxyphenbutazone, Sulfinpyrazone, Meloxicam, Piroxicam, Lornoxicam and Tenoxicam. In a preferred embodiment, NSAIDs include Aspirin, Meloxicam, Ibuprofen, Naproxen, Phosphodiesterase (PDE4) inhibitors Prostaglandin E4. The method provides the administration of a single or combination of NSAIDS.

In one embodiment of the invention, the pharmaceutical formulation comprises the H4R agonist and a pharmaceutically acceptable vehicle. In a particular embodiment, the H4R agonist is Tritoqualine or an isomer thereof.

In another embodiment of the invention, the pharmaceutical formulation comprises the H4R agonist, one or more other active agent and a pharmaceutically acceptable vehicle. In a particular embodiment, the H4R agonist is Tritoqualine or an isomer thereof. The active agent can include, but is not limited to, H1R antagonists, H2R antagonists, H3R antagonists, H4R agonist, LRAs, steroids and NSAIDs.

In yet another embodiment, the pharmaceutical composition comprises a tritoqualine and an anti-H2 drug.

The present invention also provides pharmaceutical formulations comprising a solid or liquid dosage form of a H4R agonist (e.g., Tritoqualine, E1 or E2) and a plurality of particles which permit the formulation of solid or liquid dosage form of the H4R agonist. The particles comprise, but are not limited to, excipients disclosed herein below, e.g., typical excipients for softgels.

In one embodiment, the solid or liquid dosage form of the H4R agonist formulation further comprises an H1R antagonist. In another embodiment, the solid or liquid dosage form of the H4R agonist formulation further comprises an H2R antagonist. In another embodiment, the solid or liquid dosage form of the H4R agonist formulation further comprises an H3 antagonist. In yet another embodiment, the solid or liquid dosage form of the H4R agonist formulation further comprises one or more of an H1R, an H2R antagonist, an H3 antagonist, a LRA drug and an NSAID.

In one aspect, the present invention provides a pharmaceutical composition for the treatment of H4R modulated diseases or conditions comprising a solid or liquid dosage form of the H4R agonist (e.g., Tritoqualine, E1 or E2), wherein the composition is an administrable formulation that allows resorption of the H4R agonist into a subject. In one embodiment, the administrable formulation can be, e.g., an inhalant or a topically administrable formulation such as an ointment or cream.

Anti-H1, anti-H2 and anti-H3 drugs are present in the various compositions of the invention in a proportion of the order of 0.1 to 2000 mg.

In the case of a pharmaceutical composition according to the invention containing an antihistamine compound (for example, anti-H1, anti-H2 or anti-H3) and a H4R agonist, these compounds are present in a proportion of the order of:
  0.1 to 2000 mg of anti H2 compound (when used),
  0.1 to 2000 mg of anti-H1 compound (when used),
  0.1 to 2000 mg of anti-H3 compound (when used), and
  0.10 to 3000 mg of a H4R agonist such as Tritoqualine or its isomers.

In the case of a composition according to the invention containing H4R agonist and one or more of an antihistamine compound (for example, anti-H1, anti-H2 or anti-H3), an LRA drug, a steroid drug and a NSAID, these compounds are present in a proportion of the order of:
  0.1 to 2000 mg of anti H2 compound (when used),
  0.1 to 2000 mg of anti-H1 compound (when used)
  0.1 to 2000 mg of anti-H3 compound (when used),
  0.1 to 2000 mg of a LRA drug (when used)
  0.01 to 2000 mg of steroid compound (when used),
  0.1 to 5000 mg of NSAID compound (when used), and
  0.10 to 3000 mg of a H4R agonist such as Tritoqualine or its isomers.

Further, the active agents of the invention can be pegylated, phosphorylated, esterified, derivatized with amino acids and/or peptides, to improve solubility for both formulation and bioavailability. Additionally, lipid derivatization and other lipophile derivatization can be used to improve mucosal permeability, absorption and formulation of the active agents of the invention in oily vehicles.

Dosage Forms

Dosage forms can be made according to well known methods in the art. Some preferred methods are described below.

The pharmaceutical compositions of the invention may be formulated as solid dosage forms, such as capsules, pills, softgels, tablets, caplets, troches, wafer, sprinkle, chewing gum or the like, for oral administration. The pharmaceutical compositions of the invention may also be formulated as liquid dosage forms such as elixir, suspension or syrup.

The pharmaceutical compositions of the invention may also be presented in a dosage form for transdermal application, for example an ointment for children, a form for oral administration, for example a slow release product, or in gastro-resistant tablet form or gum form. They may also be in spray, bronchial form or eye lotion form, or other galenic forms with programmed mucosal and secondarily per os disintegration.

Therefore the different pharmaceutical compositions of the invention can be administered by several routes chosen in accordance with the patient's pathological profile and age. For children, the patch form, syrup form or tablets to be dissolved in the mouth. The other forms, eye lotion or injection may also be used. In adults all galenic forms (also known as dosage forms) can be contemplated.

The advantage of a coupled or combined galenic form also provides simplicity of treatment, patient compliance with the simplified treatment and therefore a more successful outcome.

The pharmaceutical compositions of the present invention may be mixed with pharmaceutically acceptable carriers, binders, diluents, adjuvants, excipients, or vehicles, such as preserving agents, fillers, polymers, disintegrating agents, glidants, wetting agents, emulsifying agents, suspending agents, sweetening agents, flavoring agents, perfuming agents, lubricating agents, acidifying agents, coloring agent, dyes, preservatives and dispensing agents, or compounds of a similar nature depending on the nature of the mode of administration and dosage forms. Such ingredients, including pharmaceutically acceptable carriers and excipients that may be used to formulate oral dosage forms, are described in the Handbook of Pharmaceutical Excipients, American Pharmaceutical Association (1986), incorporated herein by reference in its entirety.

Pharmaceutically acceptable carriers are generally non-toxic to recipients at the dosages and concentrations employed and are compatible with other ingredients of the formulation. Examples of pharmaceutically acceptable carriers include water, saline, Ringer's solution, dextrose solution, ethanol, polyols, vegetable oils, fats, ethyl oleate, liposomes, waxes polymers, including gel forming and non-gel forming polymers, and suitable mixtures thereof. The carrier may contain minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulin; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG. Preferably the carrier is a parenteral carrier, more preferably a solution that is isotonic with the blood of the recipient.

Examples of binders include, but are not limited to, microcrystalline cellulose and cellulose derivatives, gum tragacanth, glucose solution, acacia mucilage, gelatin solution, molasses, polyinylpyrrolidine, povidone, crospovidones, sucrose and starch paste.

Examples of diluents include, but are not limited to, lactose, sucrose, starch, kaolin, salt, mannitol and dicalcium phosphate.

Examples of excipients include, but are not limited to, starch, surfactants, lipophilic vehicles, hydrophobic vehicles, pregelatinized starch, Avicel, lactose, milk sugar, sodium citrate, calcium carbonate, dicalcium phosphate, and lake blend purple. Typical excipients for dosage forms such as a softgel include gelatin for the capsule and oils such as soy oil, rice bran oil, canola oil, olive oil, corn oil, and other similar oils; glycerol, polyethylene glycol liquids, vitamin E TPGS as a surfactant and absorption enhancer (Softgels: Manufacturing Considerations; Wilkinson P, Foo Sog Horn, Special Drug Delivery Systems; Drugs and the Pharmaceutical Sciences Vol 41 Praveen Tyle Editor, Marcel Dekker 1990, 409-449; Pharmaceutical Dosage Forms and Drug Delivery by Ansel, Popovich and Allen 1995, Williams and Wilkins, Chapter 5 pp 155-225). Tritoqualine and anti H1 may form either a solution in a selected oil vehicle or a suspension of fine particles (comprising any of the excipients disclosed herein, e.g., typical excipients for softgels).

Examples of disintegrating agents include, but are not limited to, complex silicates, croscarmellose sodium, sodium starch glycolate, alginic acid, corn starch, potato starch, bentonite, methylcellulose, agar and carboxymethylcellulose.

Examples of glidants include, but are not limited to, colloidal silicon dioxide, talc, corn starch.

Examples of wetting agents include, but are not limited to, propylene glycol monostearate, sorbitan monooleate, diethylene glycol monolaurate and polyoxyethylene laural ether.

Examples of sweetening agents include, but are not limited to, sucrose, lactose, mannitol and artificial sweetening agents such as saccharin, and any number of spray dried flavors.

Examples of flavoring agents include, but are not limited to, natural flavors extracted from plants such as fruits and synthetic blends of compounds which produce a pleasant sensation, such as, but not limited to peppermint and methyl salicylate.

Examples of lubricants include magnesium or calcium stearate, sodium lauryl sulphate, talc, starch, lycopodium and stearic acid as well as high molecular weight polyethylene glycols.

Examples of coloring agents include, but are not limited to, any of the approved certified water soluble FD and C dyes, mixtures thereof; and water insoluble FD and C dyes suspended on alumina hydrate.

The artisan of ordinary skill in the art will recognize that many different ingredients can be used in formulations according to the present invention, in addition to the active agents, while maintaining effectiveness of the formulations in treating the H4R modulated diseases. The list provided herein is not exhaustive.

Matrix Based Dosage Forms

Dosage forms according to one embodiment of the present invention may be in the form of coated or uncoated matrices. The term matrix, as used herein, is given its well known meaning in the pharmaceutical arts as a solid material having an active agent (e.g., the components of the compositions of the invention) of the invention incorporated therein. Upon exposure to a dissolution media, channels are formed in the solid material so that the active agent can escape.

The skilled artisan will appreciate that the matrix material can be chosen from a wide variety of materials which can provide the desired dissolution profiles. Materials can include, for example, one or more gel forming polymers such as polyvinyl alcohol, cellulose ethers including, for example, hydroxypropylalkyl celluloses such as hydroxypropyl cellulose, hypromellose, prop-2-enoic acid, hydroxypropyl methyl cellulose, hydroxyalkyl celluloses such as hydroxypropyl cellulose, natural or synthetic gums such as guar gum, xanthum gum, and alginates, as well as ethyl cellulose, polyvinyl pyrrolidone, fats, waxes, polycarboxylic acids or esters such as the Carbopol R series of polymers, methacrylic acid copolymers, and methacrylate polymers.

In addition to the above-mentioned ingredients, a controlled release matrix may also contain suitable quantities of other materials, for example, diluents, lubricants, binders, granulating aids, colorants, flavorants, and glidants that are conventional in the pharmaceutical arts. The quantities of these additional materials should be sufficient to provide the desired effect to the desired formulation. A controlled release matrix incorporating particles may also contain suitable quantities of these other materials such as diluents, lubricants, binders, granulating aids, colorants, flavorants, and glidants that are conventional in the pharmaceutical arts in amounts up to about 75% by weight of the particulate, if desired.

Methods of making matrix dosages are well known in the art and any known method of making such dosages which yields the desired immediate release and controlled release dissolution profiles can be used. One such method involves the mixture of the compositions of the invention with a solid polymeric material and one or more pharmaceutically acceptable excipients which can then be blended and compressed in controlled release tablet cores. Such tablet cores can be used for further processing as bi-layer or multilayer tablets, press coated tablets, or film coated tablets.

In addition, the formulation of respective release components can occur by appropriate granulation methods as is well known in the art. In wet granulation, solutions of the binding agent can be added with stirring to the mixed powders. The powder mass can be wetted with the binding solution until the mass has the consistency of damp snow or brown sugar. The wet granulated material can be forced through a sieving device. Moist material from the milling step can be dried by placing it in a temperature controlled container. After drying, the granulated material can be reduced in particle size by passing it through a sieving device. Lubricant can be added, and the final blend can then be compressed into a matrix dosage form such as a matrix tablet.

In fluid-bed granulation, particles of inert material and/or active agent (e.g., the components of the compositions of the invention) can be suspended in a vertical column with a rising air stream. While the particles are suspended, a common granulating material in solution can be sprayed into the column. There will be a gradual particle buildup under a controlled set of conditions resulting in tablet granulation. Following drying and the addition of lubricant, the granulated material will be ready for compression.

In dry-granulation, the active agent (e.g., the components of the compositions of the invention), binder, diluent, and lubricant can be blended and compressed into tablets. The compressed large tablets can be comminuted through the desirable mesh screen by sieving equipment. Additional lubricant can be added to the granulated material and blended gently. The material can then be compressed into tablets.

Particle Based Dosage Forms
Immediate Release and Controlled Release Particles

Dosage forms according to another embodiment of the present invention may be in the form of coated or uncoated immediate release/controlled release dosage forms. The immediate release/controlled release dosage forms of the present invention can take the form of pharmaceutical particles. The dosage forms can include immediate release particles in combination with controlled release particles in a ratio sufficient to deliver the desired dosages of active agents (e.g., the components of the compositions of the invention). The controlled release particles can be produced by coating the immediate release particles with an enteric coat.

The particles can be produced according to any of a number of well known methods for making particles. The immediate release particles can comprise the active agent combination (the compositions of the invention) and a disintegrant. Suitable disintegrants can include, for example, starch, low-substitution hydroxypropyl cellulose, croscarmellose sodium, calcium carboxymethyl cellulose, hydroxypropyl starch, and microcrystalline cellulose.

In addition to the above-mentioned ingredients, a controlled release matrix may also contain suitable quantities of other materials, for example, diluents, lubricants, binders, granulating aids, colorants, flavorants, and glidants that are conventional in the pharmaceutical arts. The quantities of these additional materials should be sufficient to provide the desired effect to the desired formulation. A controlled release matrix incorporating particles may also contain suitable quantities of these other materials such as diluents, lubricants, binders, granulating aids, colorants, flavorants, and glidants that are conventional in the pharmaceutical arts in amounts up to about 75% by weight of the particulate, if desired.

Particles can assume any standard structure known in the pharmaceutical arts. Such structures can include, for example, matrix particles, non-pareil cores having a drug layer and active or inactive cores having multiple layers thereon. A controlled release coating can be added to any of these structures to create a controlled release particle.

The term particle as used herein means a granule having a diameter of between about 0.01 mm and about 5.0 mm, preferably between about 0.1 mm and about 2.5 mm, and more preferably between about 0.5 mm and about 2 mm. The skilled artisan will appreciate that particles according to the present invention can be any geometrical shape within this size range and so long as the mean for a statistical distribution of particles falls within the particle sizes enumerated above, they will be considered to fall within the contemplated scope of the present invention.

The release of the therapeutically active agent (e.g., the components of the compositions of the invention) from the controlled release formulation of the present invention can be further influenced, i.e., adjusted to a desired rate, by the addition of one or more release-modifying agents. The release-modifying agent may be organic or inorganic and include materials that can be dissolved, extracted, or leached from the coating in the environment of use. The pore-formers may comprise one or more hydrophilic materials such as hydroxypropyl methylcellulose. The release-modifying agent may also comprise a semi-permeable polymer. In certain preferred embodiments, the release-modifying agent is selected from hydroxypropyl methylcellulose, lactose, metal stearates, and mixtures thereof.

The controlled release particles of the present invention can slowly release the compositions of the invention when ingested. The controlled release profile of the formulations of the present invention can be altered, for example, by increasing or decreasing the thickness of a retardant coating, i.e., by varying the amount of overcoating. The resultant solid controlled release particles may thereafter be placed in a gelatin capsule in an amount sufficient to provide an effective controlled release dose when ingested and contacted by an environmental fluid, e.g., gastric fluid, intestinal fluid or dissolution media.

The dosage forms of the invention may be coated (e.g., film coated or enterically coated) as known by those of skill in the art. For example, the composition can be formulated in an enteric coating that maintains its integrity in the stomach and releases the active compound in the intestine.

Examples of enteric-coatings include, but are not limited to, phenylsalicylate, fatty acids, fats, waxes, shellac, ammoniated shellac and cellulose acetate phthalates. Film coatings include, but are not limited to, hydroxyethylcellulose, sodium carboxymethylcellulose, polyethylene glycol 4000 and cellulose acetate phthalate.

In one example, the dosage forms e.g., particles of the invention as described above, may be overcoated with an aqueous dispersion of a hydrophobic or hydrophilic material to modify the release profile. The aqueous dispersion of hydrophobic material preferably further includes an effective amount of plasticizer, e.g. triethyl citrate. Preformulated aqueous dispersions of ethylcellulose, such as AQUACOAT™ or SURELEASE™ products, may be used. If a SURELEASE™ product is used, it is not necessary to separately add a plasticizer.

The hydrophobic material may be selected from the group consisting of alkylcellulose, acrylic and methacrylic acid polymers and copolymers, shellac, zein, fatty oils, hydrogenated castor oil, hydrogenated vegetable oil, or mixtures thereof. In certain preferred embodiments, the hydrophobic material can be a pharmaceutically acceptable acrylic polymer including, but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid anhydride), polymethacrylate, polyacrylamide, poly (methacrylic acid anhydride), and glycidyl methacrylate copolymers. In alternate embodiments, the hydrophobic material can be selected from materials such as one or more hydroxyalkyl celluloses such as hydroxypropyl methylcellulose. The hydroxyalkyl cellulose can preferably be a hydroxy ($C_1$ to $C_6$) alkyl cellulose, such as hydroxypropylcellulose, hydroxypropylmethylcellulose, or preferably hydroxyethylcellulose. The amount of the hydroxyalkyl cellulose in the present oral dosage form can be determined, in part, by the precise rate of active agents (e.g., the components of the compositions of the invention) desired and may vary from about 1% to about 80%.

In embodiments of the present invention where the coating comprises an aqueous dispersion of a hydrophobic polymer, the inclusion of an effective amount of a plasticizer in the aqueous dispersion of hydrophobic polymer can further improve the physical properties of the film. For example, because ethylcellulose has a relatively high glass transition temperature and does not form flexible films under normal coating conditions, it may be necessary to plasticize the ethylcellulose before using it as a coating material. Generally, the amount of plasticizer included in a coating solution can be based on the concentration of the film-former, e.g., most often from about 1 percent to about 50 percent by weight of the film-former. Concentration of the plasticizer, however, can be preferably determined after careful experimentation with the particular coating solution and method of application.

Examples of suitable plasticizers for ethylcellulose include water-insoluble plasticizers such as dibutyl sebacate, diethyl phthalate, triethyl citrate, tributyl citrate, and triacetin, although other water-insoluble plasticizers (such as acetylated monoglycerides, phthalate esters, castor oil, etc.) may be used. Triethyl citrate may be an especially preferred plasticizer for the aqueous dispersions of ethyl cellulose of the present invention.

Examples of suitable plasticizers for the acrylic polymers of the present invention include, but are not limited to, citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as EUDRAGIT™ RL/RS lacquer solutions include polyethylene glycols, propylene glycol, diethyl phthalate, castor oil, and triacetin. Triethyl citrate may be an especially preferred plasticizer for aqueous dispersions of ethyl cellulose. It has further been found that addition of a small amount of talc may reduce the tendency of the aqueous dispersion to stick during processing and acts a polishing agent.

One commercially available aqueous dispersion of ethylcellulose is the AQUACOAT™ product which is prepared by dissolving the ethylcellulose in a water-immiscible organic solvent and then emulsifying the ethylcellulose in water in the presence of a surfactant and a stabilizer. After homogenization to generate submicron droplets, the organic solvent can be evaporated under vacuum to form a pseudolatex. The plasticizer will not be incorporated into the pseudolatex during the manufacturing phase. Thus, prior to using the pseudolatex as a coating, the AQUACOAT™ product can be mixed with a suitable plasticizer.

Another aqueous dispersion of ethylcellulose is commercially available as SURELEASE™ product (Colorcon, Inc., West Point, Pa., U.S.A.). This product can be prepared by incorporating plasticizer into the dispersion during the manufacturing process. A hot melt of a polymer, plasticizer (dibutyl sebacate), and stabilizer (oleic acid) can be prepared as a homogeneous mixture which can then be diluted with an alkaline solution to obtain an aqueous dispersion which can be applied directly onto substrates.

In one embodiment, the acrylic coating can be an acrylic resin lacquer used in the form of an aqueous dispersion, such as that which is commercially available from Rohm Pharma under the trade name EUDRAGIT™. In additional embodiments, the acrylic coating can comprise a mixture of two acrylic resin lacquers commercially available from Rohm Pharma under the trade names EUDRAGIT™ RL 30 D and EUDRAGIT™ RS 30 D. EUDRAGIT™ RL 30 D and EUDRAGIT™ RS 30 are copolymers of acrylic and methacrylic esters with a low content of quaternary ammonium groups, the molar ratio of ammonium groups to the remaining neutral (meth)acrylic esters being 1:20 in EUDRAGIT™ RL 30 and 1:40 in EUDRAGIT™ RS 30 D. The mean molecular weight is about 150,000 Daltons. The code designations RL (high permeability) and RS (low permeability) refer to the permeability properties of these agents. EUDRAGIT™ RL/RS mixtures are insoluble in water and in digestive fluids; however, coatings formed from them are swellable and permeable in aqueous solutions and digestive fluids.

The EUDRAGIT™ RL/RS dispersions may be mixed together in any desired ratio in order to ultimately obtain a controlled-release formulation having a desirable dissolution profile. Desirable controlled-release formulations may be obtained, for instance, from a retardant coating derived from one of a variety of coating combinations, such as 100% EUDRAGIT™ RL; 50% EUDRAGIT™ RL and 50% EUDRAGIT™ RS; or 10% EUDRAGIT™ RL and EUDRAGIT™ 90% RS. Of course, one skilled in the art will recognize that other acrylic polymers may also be used, for example, others under the EUDRAGIT™ brand. In addition to modifying the dissolution profile by altering the relative amounts of different acrylic resin lacquers, the dissolution profile of the ultimate product may also be modified, for example, by increasing or decreasing the thickness of the retardant coating.

The stabilized product may be obtained by subjecting the coated substrate to oven curing at a temperature above the Tg (glass transition temperature) of the plasticized acrylic polymer for the required time period, the optimum values for temperature and time for the particular formulation being determined experimentally. In certain embodiments of the present invention, the stabilized product is obtained via an oven curing conducted at a temperature of about 45° C. for a time period from about 1 to about 48 hours. It is also contemplated that certain products coated with the controlled-release coating of the present invention may require a curing time longer than 24 to 48 hours, e.g., from about 48 to about 60 hours or more.

The coating solutions preferably contain, in addition to the film-former, plasticizer, and solvent system (i.e., water), a colorant to provide elegance and product distinction. Color may be added to the solution of the compositions of the invention instead of, or in addition to the aqueous dispersion of hydrophobic material. For example, color may be added to an AQUACOAT™ product via the use of alcohol or propylene glycol based color dispersions, milled aluminum lakes and opacifiers such as titanium dioxide by adding color with shear to the water soluble polymer solution and then using low shear to the plasticized AQUACOAT™ product.

Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retardant effect of the coating.

Spheroids or beads coated with the compositions of the invention can be prepared, for example, by dissolving the compositions of the invention in water and then spraying the solution onto a substrate, for example, non pareil 18/20 beads, using a Wuster insert. Optionally, additional ingredients can also be added prior to coating the beads in order to assist the binding of the compositions of the invention to the beads, and/or to color the solution, etc. For example, a product which includes hydroxypropyl methylcellulose with or without colorant (e.g., OPADRY™ product, commercially available from Coloron, Inc.) may be added to the solution and the solution mixed (e.g., for about 1 hour) prior to application onto the beads. The resultant coated substrate, beads in this example, may then be optionally overcoated with a barrier agent to separate the compositions of the invention from the hydrophobic controlled release coating. An example of a suitable barrier agent is one which comprises hydroxypropyl cellulose. However, any film-former known in the art may be used. It is preferred that the barrier agent does not affect the dissolution rate of the final product.

Immediate release particles according to the present invention may be coated with a controlled release coating in order to change the release rate to obtain the dissolution rates according to the present invention.

Press Coated, Pulsatile Dosage Form

In another embodiment of the present invention, the compositions of the invention can be administered via a press coated pulsatile drug delivery system suitable for oral administration with a controlled release component, which contains a compressed blend of an active agent (e.g., the components of the compositions of the invention) and one or more polymers, substantially enveloped by an immediate release component, which contains a compressed blend of the active agent and hydrophilic and hydrophobic polymers. The immediate-release component preferably comprises a compressed blend of active agent and one or more polymers with disintegration characteristics such that the polymers disintegrate rapidly upon exposure to the aqueous medium.

The controlled-release component preferably can comprise a combination of hydrophilic and hydrophobic polymers. In this embodiment, once administered, the hydrophilic polymer will dissolve away to weaken the structure of the controlled-release component, and the hydrophobic polymer will retard the water penetration and help to maintain the shape of the drug delivery system.

In accordance with the present invention, the term "polymer" includes single or multiple polymeric substances, which can swell, gel, degrade or erode on contact with an aqueous environment (e.g., water). Examples include alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polacrilin potassium, powdered cellulose, pregelatinized starch, sodium alginate, sodium starch glycolate, starch, ethylcellulose, gelatin, hydroxyethyl cellulose, hydroxypropyl cellulose, hydroxypropyl methylcellulose, polymethacrylates, povidone, pregelatinized starch, shellac, and zein, and combinations thereof.

The term "hydrophilic polymers" as used herein includes one or more of carboxymethylcellulose, natural gums such as guar gum or gum acacia, gum tragacanth, or gum xanthan, hydroxyethyl cellulose, hydroxypropyl cellulose, hydroxypropyl methylcellulose, methylcellulose, and povidone, of which hydroxypropyl methylcellulose is further preferred. The term "hydrophilic polymers" can also include sodium carboxymethylcellulose, hydroxymethyl cellulose, polyethelene oxide, hydroxyethyl methyl cellulose, carboxypolymethylene, polyethelene glycol, alginic acid, gelatin, polyvinyl alcohol, polyvinylpyrrolidones, polyacrylamides, polymethacrylamides, polyphosphazines, polyoxazolidines, poly(hydroxyalkylcarboxylic acids), an alkali metal or alkaline earth metal, carageenate alginates, ammonium alginate, sodium alganate, or mixtures thereof.

The hydrophobic polymer of the drug delivery system can be any hydrophobic polymer which will achieve the goals of the present invention including, but not limited to, one or more polymers selected from carbomer, carnauba wax, ethylcellulose, glyceryl palmitostearate, hydrogenated castor oil, hydrogenated vegetable oil type 1, microcrystalline wax, polacrilin potassium, polymethacrylates, or stearic acid, of which hydrogenated vegetable oil type 1 is preferred. Hydrophobic polymers can include, for example, a pharmaceutically acceptable acrylic polymer, including, but not limited to, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methyl methacrylate) copolymer, polyacrylamide, aminoalkyl methacrylate copolymer, poly(methacrylic acid anhydride), and glycidyl methacrylate copolymers. Additionally, the acrylic polymers may be cationic, anionic, or non-ionic polymers and may be acrylates, methacrylates, formed of methacrylic acid or methacrylic acid esters. The polymers may also be pH dependent.

The present invention also provides a method for preparing a press coated, pulsatile drug delivery system comprising the compositions of the invention suitable for oral administration. This method can include the steps of combining an effective amount of the components of the compositions of the invention, or a pharmaceutically acceptable salt thereof, and a polymer to form an immediate-release component; combining an effective amount of an active agent (e.g., the components of the compositions of the invention), or a pharmaceutically acceptable salt thereof, and a combination of hydrophilic and hydrophobic polymers to form a controlled release component; and press coating the controlled-release component to substantially envelop the immediate release component.

A preferred embodiment further can include the steps of combining an effective amount of an active agent (e.g., the components of the compositions of the invention), or a pharmaceutically acceptable salt thereof, and a polymer to form an immediate release component, and press coating the immediate release component to substantially envelop the controlled release component. In another preferred embodiment, the combining steps can be done by blending, wet granulation, fluid-bed granulation, or dry granulation according to methods recognized in the art.

The active agents of the invention can also be mixed with other active materials which do not impair the desired action, or with materials that supplement the desired action, such as antacids, H2 blockers and anti-inflammatory agents. Higher concentrations, up to about 98% by weight of the components of the compositions of the invention may be included.

The dosage form of the invention may be administered to mammalian subjects, including: humans, monkeys, apes, dogs, cats, cows, horses, rabbits, pigs, mice and rats.

The dosage form of the invention may be administered orally (e.g., in liquid form within a solvent such as an aqueous or non-aqueous liquid, or within a solid carrier), rectally, parenterally, intracisternally, intravaginally, intraperitoneally, topically (as by powders, ointments, lotion, gels, drops, transdermal patch or transcutaneous patch), bucally, in bronchial form or as an oral or nasal spray. The term "parenteral" as used herein refers to modes of administration which include intravenous (e.g., within a dextrose or saline solution), intramuscular, intrasternal, subcutaneous, intracutaneous, intrasynovial, intrathecal, periostal, intracerebroventricularly, intra-articular injection and/or infusion. Alternative methods include administration by pump or continuous infusion, injection (e.g., as a suspension or as an emulsion in a pharmaceutically acceptable liquid or mixture of liquids), or liposomes. Administration can be performed daily, weekly, monthly, every other month, quarterly or any other schedule of administration as a single dose injection or infusion, multiple doses, or in continuous dose form. The administration of the pharmaceutical compositions of the present invention can be intermittent or at a gradual, continuous, constant or controlled rate to a subject. In addition, the time of day and the number of times per day that dosage form(s) is administered can vary.

For parenteral administration, in one embodiment, the agents of the invention can be formulated generally by mixing it at the desired degree of purity, in a unit dosage injectable form (solution, suspension, or emulsion), with a pharmaceutically acceptable carrier(s) described above.

Any dosage form used for therapeutic administration should be sterile. Sterility can readily be accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

The appropriate dose of the compound will be that amount effective to prevent occurrence of the symptoms of the food allergy, COPD or GERD and/or other gastrointestinal conditions ameliorated by proper histamine management or to treat some symptoms of the food allergy, COPD or GERD and/or other gastrointestinal conditions ameliorated by proper histamine management from which the patient suffers. By "effective amount", "therapeutic amount" or "effective dose" is meant that amount sufficient to elicit the desired pharmacological or therapeutic effects, thus resulting in effective prevention or treatment of the disorder or condition. Prevention of the food allergy, COPD, GERD and/or other gastrointestinal conditions ameliorated by proper histamine management can be manifested by delaying the onset of the symptoms of food allergy, COPD or GERD (e.g., acid reflux, heartburn, a burning sensation in the chest, occasionally a bitter taste in the mouth, cough, back pain) and/or other gastrointestinal conditions ameliorated by proper histamine management. Treatment of the disorder can be manifested by a decrease in the symptoms associated with food allergies, COPD, GERD and/or other gastrointestinal conditions ameliorated by proper histamine management or an amelioration of the recurrence of the symptoms of the food allergies, COPD, GERD and/or other gastrointestinal conditions ameliorated by proper histamine management.

Kits of the Invention

In a further embodiment, the present invention provides kits (i.e., a packaged combination of reagents with instructions) containing the active agents of the invention useful for treating H4R modulated diseases and/or conditions.

The kit can contain a pharmaceutical composition that includes one or more agents of the invention effective for treating H4R modulated diseases and an acceptable carrier or adjuvant, e.g., pharmaceutically acceptable buffer, such as phosphate-buffered saline, Ringer's solution or dextrose solution. It may further include other materials desirable from a commercial and user standpoint, including other buffers, diluents, filters, needles, syringes, and package inserts with instructions for use.

The agents may be provided as dry powders, usually lyophilized, including excipients that upon dissolving will provide a reagent solution having the appropriate concentration.

The kit comprises one or more containers with a label and/or instructions. The label can provide directions for carrying out the preparation of the agents for example, dissolving of the dry powders, and/or treatment for H4R modulated diseases and/or conditions.

The label and/or the instructions can indicate directions for in vivo use of the pharmaceutical composition. The label and/or the instructions can indicate that the pharmaceutical composition is used alone, or in combination with another agent to treat H4R modulated diseases or conditions.

The label can indicate appropriate dosages for the agents of the invention as described supra.

Suitable containers include, for example, bottles, vials, and test tubes. The containers can be formed from a variety of materials such as glass or plastic. The container can have a sterile access port (for example the container can be an intravenous solution bag or a vial having a stopper pierceable by a needle such as a hypodermic injection needle).

Advantages of the Invention

The invention disclosed herein relates to the surprising discovery that H4R agonists can be used for the treatment of H4R modulated diseases.

As discussed supra, current treatment of histamine related diseases generally focuses on the use of antagonists for H1R and H2R for the treatment of such diseases. Based on the current state in the art of the therapeutic utility of histamine receptors, those skilled in the art have proposed using H4R antagonists as the main therapeutic approach to exploit the H4R functions.

There is currently no commercially available drug to treat H4R modulated diseases that is a H4R agonist. Thus, there is an unmet and unperceived need to develop H4R agonists to treat H4R modulated diseases.

EXAMPLES

Example 1

TRQ+Anti-H1 or TRQ+Anti-H1+Anti-H2 Treatment of GERD Patients

The effectiveness of the combination of Tritoqualine with an anti-H1 and combination of Tritoqualine with an anti-H1 drug and an anti-H2 drug was demonstrated in human studies.
Patient Cohort Patients at baseline had at least a one year history of GERD for whom treatment with proton pump inhibitors (PPI) did not satisfactorily manage GERD symptoms. Baseline patients were diagnosed with GERD and Respiratory symptoms of allergy such as Allergic Rhinitis and Asthma.

Two groups of patients were treated in this study. The first group (Group A) was treated with an H4R agonist, Tritoqualine at 200 mg daily and an anti-H1 drug, Loratadine at 10 mg daily. The second group (Group B) was treated with a combination of a H4R agonist, Tritoqualine at 200 mg daily; an anti-H1 drug, Loratadine at 10 mg daily, and an anti-H2 drug, Ranitidine at 150 mg daily. The demographic characteristics of the patients are shown on Table 1.

Patients were recruited based upon the aforementioned criteria, and were examined by a physician at the initial visit (To) and following visit (T1) set after 6-8 weeks of treatment with the relevant drug combination.
Results Each patient was scored in both the initial visit (T0) and the visit 6-8 weeks later (T1) by the physician. Scoring of the symptoms is shown in Table 2. Both groups showed improvement using either combination of two drugs (Group A: H4R agonist and anti-H1 drug) or three drugs (Group B: H4R agonist and anti-H1 drug and anti-H2 drug). Overall, Group B showed superior score compared to Group A.

Based on the data presented above, patients diagnosed with GERD were inadequately treated with PPI and AntiH1 drug alone prior to the treatments described in this invention (patients were taking AntiH1 to control allergic symptoms and not to control GERD). The average score of 6.4 which represents GERD symptoms such as heartburn, regurgitation, and cough was indicative of the discomfort and inadequate treatment.

Removal of the PPI and introduction of the H4R agonist such as Tritoqualine with anti-H1 drugs in one group and Tritoqualine plus anti-H2 drug such as Ranitidine on the other group clearly improved the symptoms of GERD, by 82.9% (100*(6.4−3.5)/3.5) and 209.5% (100*(6.5−2.1)/2.1), respectively.

TABLE 1

Summary of the population demographics

|  | Age | Average Age | Interval | Female | Male |
|---|---|---|---|---|---|
| Group A | 20-60 | 44 | 15 | 31 | 14 |
| Group B | 20-60 | 46 | 13 | 13 | 10 |
| Total # of patients |  |  |  | 44 | 24 |

TABLE 2

Scoring guide for the magnitude of symptoms for GERD patients

| | Scores | | | |
|---|---|---|---|---|
| Symptoms | No symptoms | Moderate Symptoms | Symptoms occurring each day | Symptoms occurring each day and night |
| Heartburn | 0 | 1 | 2 | 3 |
| Regurgitation | 0 | 1 | 2 | 3 |
| Cough | 0 | 1 | 2 | 3 |
| Global Score | 0 | 3 | 6 | 9 |

TABLE 3

Results of the study

|  | Global Score To (initial visit) | Global Score T1 (visit after 6-8 weeks) | p-value |
|---|---|---|---|
| Group A | 6.4 | 3.5 | 0.005 |
| Group B | 6.5 | 2.1 | 0.002 |
| p-value | NS | 0.01 |  |

NS = Not significant

Example 2

TRQ+Anti-H1, TRQ+Anti-H2 or TRQ+Anti-H1+Anti-H2 Treatment of GERD Patients

The effectiveness of the combination of Tritoqualine with an anti-H1, combination of Tritoqualine with an anti-H2 and combination of Tritoqualine with both anti-H1 and anti-H2 was demonstrated in human studies.
Patient Cohort Patients at baseline had at least one year history of GERD, for whom treatment with proton-pump inhibitors, anti-H1, anti-H2 and combination of anti-H1 and anti-H2 yielded unsatisfactory management of GERD symptoms. Baseline patients had received anti-H2 in the dosages range of 400-800 mg of Ranitidine per day, anti-H1 in the dosage range of about 10 mg Loratadine per day, and proton pump inhibitors (PPI) in the dosage range of about 40-60 mg of Omeprazole or Esomeprazole per day. The baseline patients were diagnosed with GERD and respiratory symptoms of allergy such as allergic rhinitis and asthma.

The one year history of allergies was confirmed with two positive prick tests. The list of prick tested allergens included *Dermatophagoid Pteronysinus, Dermatophagoid Farinae*, and cat and dog dander; food allergen such as wheat egg, soy, potato, peanut and tomato proteins; fungal proteins such as *alternaria, mucor,* and *apergillus*; pollen proteins such as birch tree, cypress tree, Quercus tree, lolium perenne and ray grass pollen.

Three groups of patients were treated in this study. The first group, Group A, was treated with an H4R agonist, Tritoqualine, 200 mg daily and an Anti-H1 drug, Loratadine, 10 mg daily. The second group, Group B, was treated with a combination of a H4R agonist Tritoqualine, 200 mg daily; an Anti-H1 drug, loratadine 10 mg daily, and an Anti-H2 drug, Ranitidine, 150 mg daily. The third group, Group C, was treated with an H4R agonist, Tritoqualine, 200 mg daily, and an Anti-H2 drug, Ranitidine, 150 mg daily.

The study population characteristics of the patients are shown on Table 4.

Patients were recruited based upon the aforementioned criteria, and were examined by an allergist physician at the initial visit (To) and another doctor visitation (T1) set 6-8 weeks after treatment using the relevant drug combination (three drug combinations used described above).

Each patient was examined by the allergist both by a physical exam and answering a standard questionnaire. The questionnaire included questions such as whether the patient took proton-pump inhibitors and whether and the frequency at which the patient experienced heartburn, regurgitation and cough. Each patient was then assigned a score by the allergist for each of the GERD symptoms pursued in this study. Scores were assigned both during the initial visit (To) and the visit (T1) (scheduled within 6-8 weeks from T(o)). The severity of the following symptoms was assessed: heartburn, regurgitation, and cough. If the patient presented no symptoms of any of the specific attribute (heartburn, regurgitation, and cough) was assigned a 0 score for that attribute. Moderate symptoms (when the symptom occurs in the frequency of less than once per day) were given the score of 1. Symptoms occurring each day were given a score of 2 and symptoms occurring each day and night the score of 3. The scores of each symptom were added together to result in the global GERD score for each patient. Global scores were then compared from visits T (o) and T(1). Significant reduction in global scores indicated that the therapy improved the global GERD condition for each patient. A summary of the scoring system is shown on Table 5. The average T(o) and T1 scores for all male and female patients was calculated (need standard deviation) and reported in Table 6. Conducting a t-test, the p-value for each group was calculated. P-Values<0.05 would indicate that symptoms at visit T(o) and T(1) are significantly different from each other. If the total score at visit T(1) is significantly lower than at visit T(o) it will be concluded that the effect of the drug combination was positive and therefore the treatment of the relevant combination of drugs, efficacious.

Results and Discussion

All groups, A, B and C, showed an improvement using all three combinations of drugs (Group A: H4R agonist and AntiH1 drug); (Group B: H4R agonist and AntiH1 drug and Anti H2 drug) and (Group C: H4R agonist and AntiH2 drug). Overall, groups B and C showed superior score compared to group A. It is therefore concluded that combinations of and H4R agonist such as Tritoqualine plus AntiH2 drugs such as Ranitidine at low dosages is an effective way to control the symptoms of GERD of allergic patients that are not responding to proton pump inhibitors or Anti H2 drugs alone. The treatment in group A is also effective in treating GERD. The results however of groups B and C are superior to group A.

TABLE 4

Summary of the patient details in the study

| | Age | Average Age | Interval | Female | Male |
|---|---|---|---|---|---|
| Group A | 20-60 | 44 | 15 | 31 | 14 |
| Group B | 20-60 | 46 | 13 | 13 | 10 |
| Group C | 20-60 | 48 | 12 | 1 | 2 |
| Total | | | | 45 | 26 |
| Percentage | | | | 63 | 37 |

TABLE 5

| Scoring | Symptoms | | | |
|---|---|---|---|---|
| | No symptoms | Moderate Symptoms | Symptoms occurring each day | Symptoms occurring each day and night |
| Heartburn | 0 | 1 | 2 | 3 |
| Regurgitation | 0 | 1 | 2 | 3 |
| Cough | 0 | 1 | 2 | 3 |
| Global Score | 0 | 3 | 6 | 9 |

TABLE 6

| | Global Score GERD T(o) (initial visit) | Global Score GERD T1 (visit after 6-8 weeks) | P value |
|---|---|---|---|
| Group A | 6.4 | 3.5 | 0.005 |
| Group B | 6.5 | 2.1 | 0.002 |
| Group C | 6.5 | 2.0 | 0.01 |
| P value | NS | 0.01 | |

Example 3

Characterization of TRQ, E1 and E2

Figure 2:
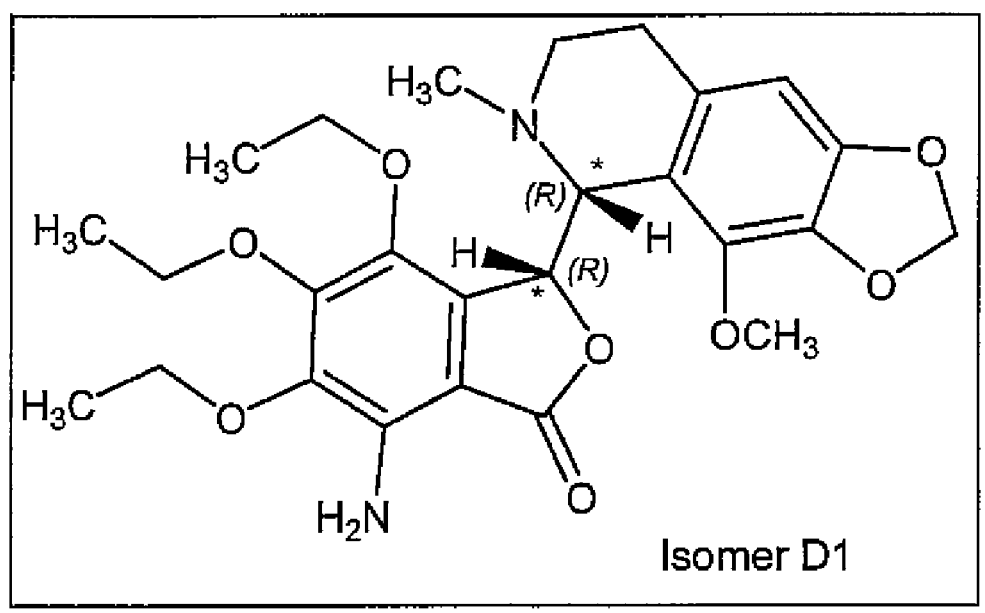
FIG. 2 illustrates the sterical structure of the Tritoqualine diastereomer D1, as described in Example 3, below.
Figure 3:
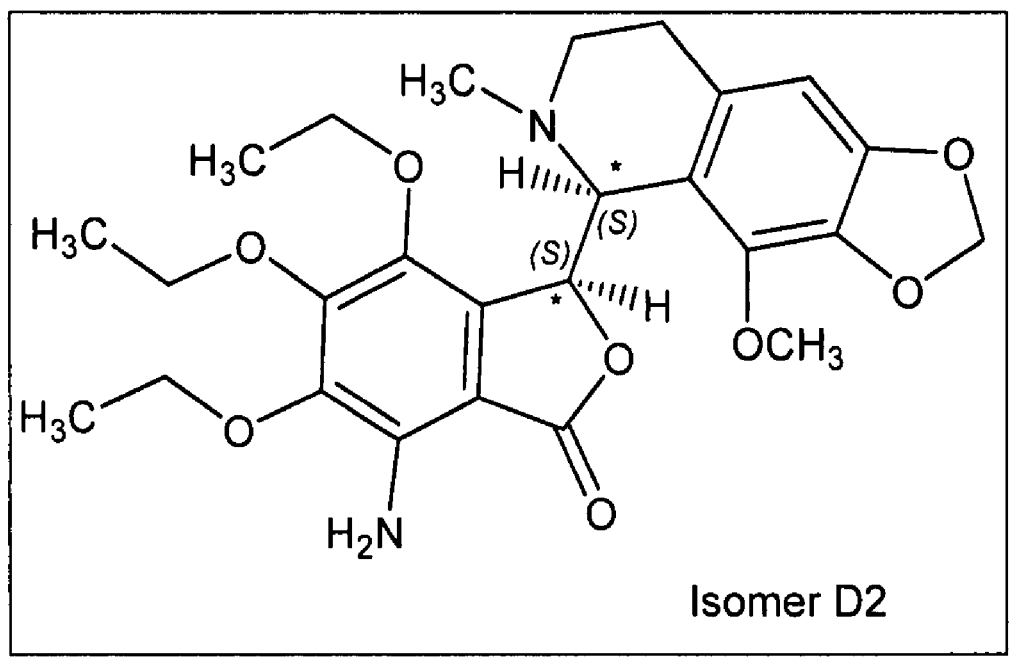
FIG. 3 illustrates the sterical structure of the Tritoqualine diastereomer D2, as described in Example 3, below.

The known chemical structure of Tritoqualine, illustrated in FIG. 1, is characterized by, amongst other structural features, the presence of two asymmetric carbons, A and B (marked with asterisk). Thus, depending on the method of synthesis, Tritoqualine active pharmaceutical ingredient can be produced as either one or two diastereomeric structures each one comprising of its corresponding two mirror images, enantiomers. Thus, Tritoqualine can exist as either two or four possible isomeric structures. Using the convention of R and S designation in each asymmetric carbon, one of the two possible diastereomeric structures will be comprised of the RR and SS enantiomers, and the other of RS and SR enantiomers. Embodiments of the two enantiomers include an isolated stereoisomer of Tritoqualine having the structure D1 of FIG. 2 and an isolated stereoisomer of Tritoqualine having the structure D2 of FIG. 3 and pharmaceutical compositions thereof.

Materials and Methods

Extraction of Tritoqualine from tablets: Forty 100 mg Tritoqualine tablets were crushed using mortar and pestle and the white powder was transferred to an Erlenmeyer flask. Addition of 400 mL ethyl acetate resulted in the formation of a fine white suspension. The suspension was allowed to stir for 1 hour under ambient conditions. Filtration of all insoluble matter, removal of solvent by rotary evaporation afforded a white crystalline solid. This solid was then dissolved in approximately 100 mL of dichloromethane. Hexane was added to the above solution until it became cloudy. After overnight storage at room temperature, Tritoqualine crystalline material formed at the bottom of the glass affording 3.5 g of pure Tritoqualine.

Analytical Separation and Isolation of Tritoqualine Stereoisomers:

Thin layer chromatography: various proportions of ethyl acetate/hexane, dichloromethane/hexane, and ethyl acetate dichloromethane were used in conjunction with silica-based thin layer chromatography to identify the number of compounds available in the mixture. In all cases of mobile phase mixtures, there was only one single spot observed (seen under UV light) indicating the presence of only one diastereomer. The two enantiomers comprising the diastereomer could not be resolved using silica-based thin layer chromatography.

HPLC separation of Tritoqualine enantiomers: HPLC separation was conducted using an Agilent 1100 HPLC system equipped with a quaternary pump, injector, diode array detector and a Jasco OR-990 polarimetric detector. The successful chromatographic separation utilized the chiral HPLC column CHIRALPAK®IA (250 mm, 4.6 mm, 5 μm) with the following conditions: mobile phase: n-heptane/dichloromethane 60:40; flow rate 1 ml/min; temp 25° C.; Tritoqualine concentration injected was 8 g/l in mobile phase; injection volume 1 μl; UV detection: 290 nm. UV spectra for each enantiomer were obtained using the diode array detector and absorption of polarized light using a polarimetric detector.

HPLC purification of Tritoqualine enantiomers: Purification of each Tritoqualine enantiomer was conducted using a similar Agilent HPLC with a preparatory chiral column CHIRALPAK®IA (250 mm, 4.6 mm, 5 μm). Mobile phase: n-heptane dichloromethane 60:40; flow rate 20 mL/min; temp 25° C., UV detection 250 nm. Each enantiomer was collected as was eluted from the column. To ensure purity of each enantiomer HPLC analysis using the analytical column CHIRALPAK®IA (250 mm, 4.6 mm, 5 μm), mobile phase: n-heptane/dichloromethane 60:40; flow rate 1 ml/min; temp 25° C.; UV detection: 250 nm. Enantiomer A eluted at retention time of −5.95 min and enantiomer B at retention time of 7.19 mins. Chemical purities for each isolated compound exceeded the 99.5%. Enantiomeric excess for enantiomer A was 99.5% and enantiomer B was 99.0%. Solvent removal afforded each isolated isomer as an amorphous white powder.

Characterization of the Commercial Mixture of Tritoqualine and of Each Isolated Enantiomer by NMR.

$^1$H NMR spectra were recorded on a Brucker AMX 500 (500 MHz). Chemical shifts are expressed in parts per million (δ) relative to residual solvents as internal standards.

$^1$H NMR characterization of the commercial Tritoqualine product isolated from tablets: $^1$H NMR (CDCl$_3$) δ 6.36 (1H, s), 5.88 (2H, m), 5.59 (1H, d, J=1.71 Hz), 5.03 (2H, s), 4.54 (1H, s), 4.08 (9H, m), [3.08 (1H, m), 2.76 (1H, m), 2.56 (1H, m), 2.43 (1H, m)], 2.14 (3H, s), 1.39-1.45 (9H, m).

$^1$H NMR characterization of isolated enantiomer A: $^1$H NMR (CDCl$_3$) δ Ar 6.35 (1H, s), O—, 5.87 (2H, m), 5.58 (1H, s), 5.02 (2H, s), 4.54 (1H, s), 4.08 (9H, m), [3.04 (1H, m), 2.79 (1H, m), 2.55 (1H, m), 2.41 (1H, m)], 2.13 (3H, s), 1.37-1.45 (9H, m).

$^1$H NMR characterization of isolated enantiomer B: $^1$H NMR (CDCl$_3$) δ 6.36 (1H, s), 5.88 (2H, m), 5.58 (1H, d, J=1.71 Hz), 5.02 (2H, s), 4.54 (1H, s), OCH$_3$ 4.07 (9H, m), 3.04 (1H, m), 2.77 (1H, m), 2.55 (1H, m), 2.41 (1H, m), 2.13 (3H, s), 1.37-1.45 (9H, m).

Crystallography

Figure 6:
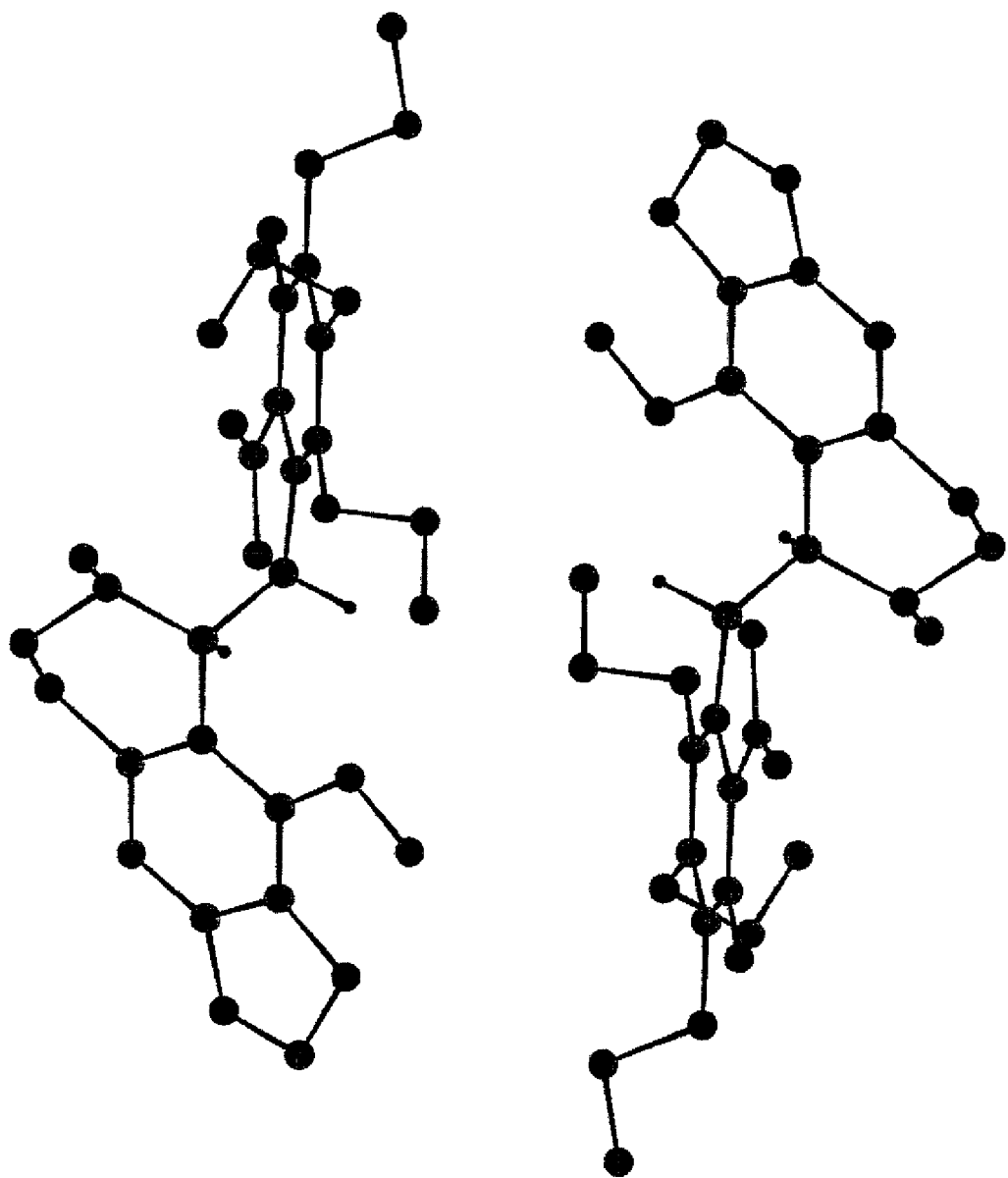
FIG. 6 illustrates the 3D-structures of the two stereoisomers (enantiomers) of FIGS. 4 and 5 as determined by X-Ray crystallography, as described in Example 3, below.

A crystal of Tritoqualine, afforded by the recrystallization procedure described above, was chosen for X-Ray crystallography. The crystal structure of commercial Tritoqualine was determined by an expert crystallographer. The data is reported in Tables S1-S5 and a picture of the existing structures is illustrated in FIG. 6 below.

Crystal Structure Determination C$_{26}$H$_{32}$N$_2$O$_8$

The Brucker X8-APEX X-ray diffraction instrument with Mo-radiation was used for data collection. All data frames were collected at low temperatures (T=90 K), using an ω, φ-scan mode (0.3° ω-scan width, hemisphere of reflections), and integrated using a Brucker SAINTPLUS software package. The intensity data were corrected for Lorentzian polarization. Absorption corrections were performed using the SADABS program. The SIR97 was used for direct methods of phase determination, and Brucker SHELXTL software for structure refinement and difference Fourier maps. Atomic coordinates, isotropic and anisotropic displacement parameters, of all the non-hydrogen atoms were refined, by means of a full matrix least-squares procedure on F$^2$. All H-atoms were included in the refinement, in calculated positions riding on the C atoms, with U[iso] fixed at 20% higher, than isotropic parameters of carbons atoms which they were attached. Drawing of molecule was performed using Ortep 3.

Crystal and structure parameters: size 0.38×0.20×0.10 mm$^3$, monoclinic, space group P2(1)/n, a=16.7348(6) Å, b=7.8819(3) Å, c=18.5117(6) Å, α=90.0° β=985090(10)° γ=90.0°, V=2414.85(15) Å$^3$, ρ$_{calcd}$=1.377 g/cm$^3$, 2θ$_{max}$=65.26°, Mo-radiation λ=0.71073 Å), low temperature=90(2) K, reflections collected=33322, independent reflections=8434 (R$_{int}$=0.0372, R$_{sig}$=0.0382), 6524 (77.4%) reflections were greater than 2σ(I), index ranges 25<=h<=24, −11<=k<=10, −27<=l<=25, absorption coefficient μ=0.102 mm$^{-1}$, max/min transmission=0.9898 and 0.9621, 399 parameters were refined and converged at R1=0.0493, wR2=0.1210, with intensity I>2σ(I), the final difference map was 0.431 and −0.272 e·Å$^{-3}$.

Mass Spectrometry

Mass spectrometry results showed molecular ion peaks for each enantiomer to be 500. The mass spectrometry data was recorded on Applied Biosystems PI 100 electrospray mass spectrometer. The samples were run in positive mode and (M$^+$+1) values are reported 501.6 for enantiomer A and 501.5 for enantiomer B.

Results and Discussion

Separation, Characterization and Isolation of Tritoqualine Enantiomers:

Silica-based thin layer chromatography was not able to separate and resolve any Tritoqualine diastereomers. In general, diastereomeric compounds can be separated in silica-based thin layer chromatography. Enantiomers, on the other hand cannot be separated by silica-based chromatography. A chiral solid phase is necessary to separate and resolve enantiomers. Therefore, it was postulated that the commercial Tritoqualine material was a mixture of enantiomers.

Figure 4:
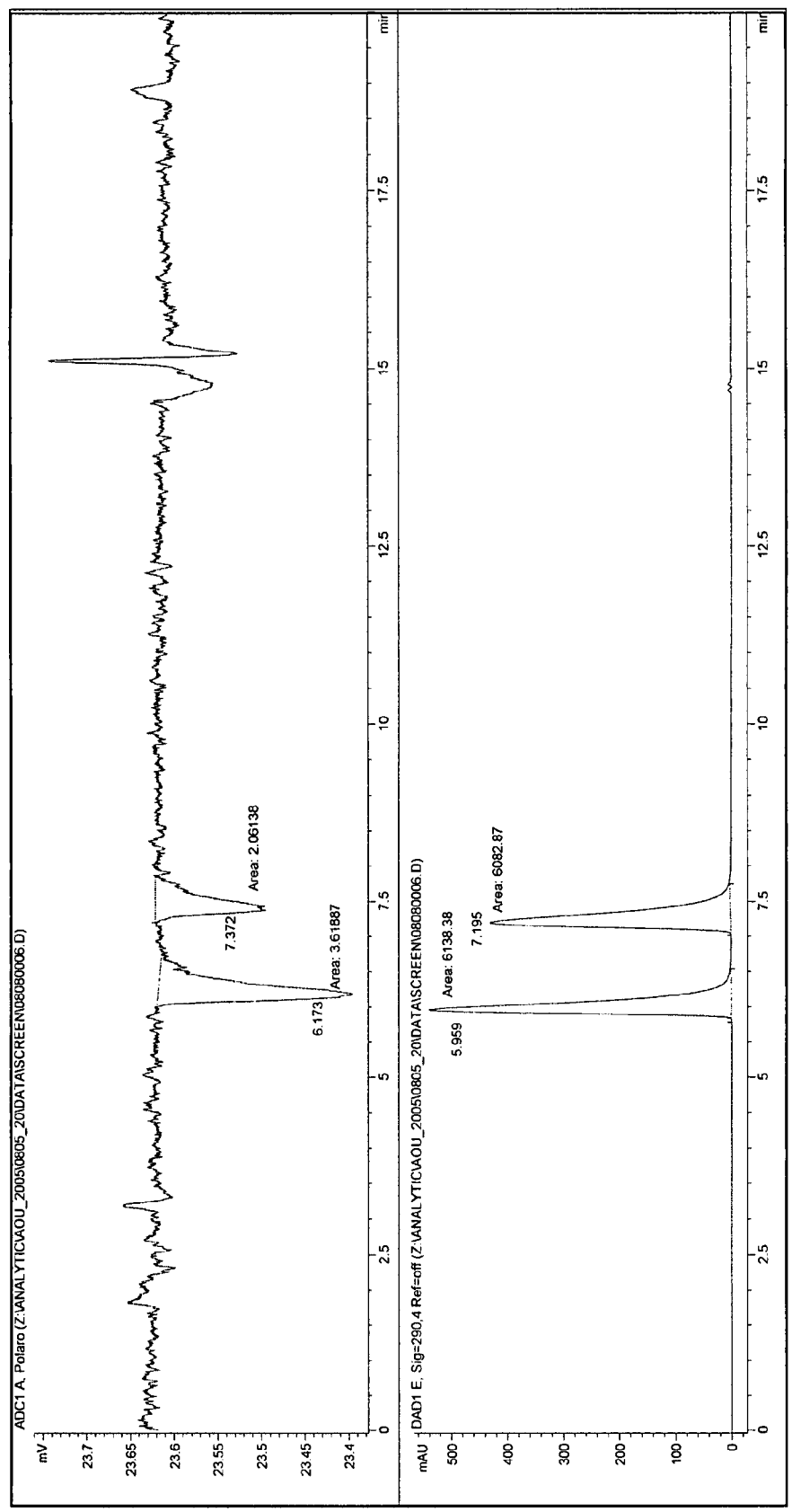
FIG. 4 shows a chromatogram of the separation of Tritoqualine stereoisomers via a chiral column. In the bottom part, the UV absorbance at 190 nm has been detected, while the top part depicts polarimetric detection at an averaged absorption in the range of 200-800 nm, as described in Example 3, below.
Figure 5:
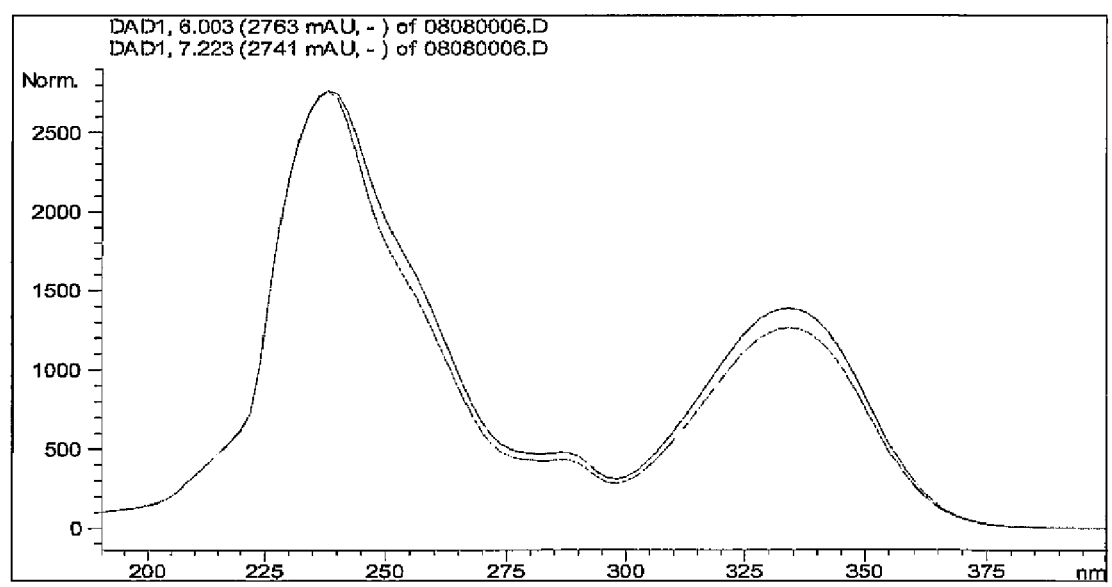
FIG. 5 shows a UV spectrum of each of the peaks of FIG. 4, as described in Example 3, below.

Chiral chromatography was employed in order to test commercial Tritoqualine (two chiral centers) for the presence of enantiomers. FIG. 4 (bottom part) illustrates a representative chromatogram of Tritoqualine chromatographed on a chiral column. Clearly, two distinct and well resolved peaks of approximately the same area could be identified, at 5.95 and 7.19 minutes respectively. Polarimetric detection (FIG. 4, top part) indicates that each peak on the chromatogram absorbs polarized light suggesting that each molecule eluting from the chiral column is an optically active compound. However, the polarimetric detector, in contrast to the standard polarimeters, does not measure the sign of the rotatory power at a given wavelength, but only gives an average response over a range of wavelengths (200-800 nm). As the sign of the rotatory power may change depending on the wavelength for the same isomer (for certain compounds), especially for compounds having UV absorption at high wavelengths (>300 nm) which is the case of Tritoqualine (FIG. 5), it was not possible to draw conclusions by this technique beyond the notion that each peak represents an optical isomer. From the diode array detector available on the HPLC setup the UV spectrum of each peak was obtained as shown on FIG. 5. Both compounds show almost identical UV spectra, which is the case of enantiomers. To further confirm the presence of enantiomers, $^1$HNMR spectra of the mixture and of the individual components are identical. If two optically active diastereomers were present in the mixture, then two sets of peaks for each diastereomer would have been expected.

Diastereomer Identification in Commercial Tritoqualine:

The Tritoqualine structure contains two chiral centers (FIG. 1). Thus, there could only be two possible diastereomeric structures. One comprised of the enantiomers RR and SS and a second comprised of the enantiomers RS and SR.

Based on the data generated above, the only reasonable conclusion was that commercial Tritoqualine is a single diastereomeric structure. The challenge to find whether commercial Tritoqualine is the RR/SS or the RS/SR remains.

To solve this issue, a single crystal from the recrystallized Tritoqualine was identified and the crystal structure was determined by an expert crystallographer. The crystallography data indicates that on the single Tritoqualine crystal there are two molecules present that are enantiomers of a single diastereomer. The two enantiomers bear the RR and the SS configuration.

All relevant information is shown on Tables 8-12 and the molecular structures of the two enantiomers are illustrated on FIG. 6.

Isolation of Tritoqualine Enantiomers for the Purposes of Biological Activity Determination:

Using the preparatory chiral column CHIRALPAK®IA (250 mm, 4.6 mm, 5 μm) and the HPLC system described above, the two enantiomers, enantiomer A and B have been successfully isolated as amorphous white powders.

Purification of Human Histidine Decarboxylase

The DNA encoding for residues 1-512 of human HDC was subcloned in the pGEX-6P-1 vector (GE-Healthcare). The recombinant plasmid transformed into the *Escherichia coli* BL21(DE3)pLysS strain. Transformed cultures were induced to express the HDC 1/512, which was purified by affinity chromatography using Glutathione sepharose (GE-Healthcare). 1/512 HDC was released from the fusion protein bound to the affinity chromatography support by digestion with the Pre-Scission™ protease (GE-Healthcare). The final preparations were dissolved in 50 mM potassium phosphate, 0.1 mM PLP, pH 7.0. Purity of the HDC 1/512 construct was checked by Coomassie blue staining and Western blotting, and was higher than 95% in the final preparations.

Human-HDC Activity Determination

HDC activity was assayed, as described in Engel at al. (1996) Biochem J. 320: 365-368, by measuring the production of $^{14}CO_2$ from L-[U-$^{14}$C]histidine (GE-Healthcare) in a mixture containing 0.2 mM dithiothreitol, 10 μM PLP, 10 mg/ml poly(ethylene glycol)-300, 100 mM potassium phosphate, pH 6.8, and purified protein in a total volume of 100 μL. When recombinant HDC was used, the concentration of L[U-$^{14}$C]histidine was 13.3 μM (with ⅓ isotopic dilution). The released $^{14}CO2$ was measured as previously described for HDC activity determinations (Urdiales et al. (1992) FEBS Lett. 305, 260-264).

Assessment of Inhibitory Activity of Each Isomeric Component, Versus the Mixture:

10 μM concentration of each isomer, A and B (A corresponds to the isolated pure isomer eluting at 5.9 minutes, B corresponds to the isolated pure isomer eluting at 7.1 minutes of the chromatogram shown in FIG. 4 (bottom)) and their corresponding racemic mixture (starting material prior to separating the individual isomers, indicated as A+B) along with 4 μg of recombinant human HDC were used to asses the inhibitory effect of each isomer and the mixture on the enzymatic conversion of histidine to histamine. Table 7 summarizes results obtained. Results are presented as means of duplicates samples. As shown in Table 7, the pure isomers (isomer A and isomer B) have more activity compared to the racemic mix (A+B).

TABLE 7

Effect of compound A, B and A + B on activity of recombinant HDC at micromolar concentration.

| Sample | DPM | Activity (μmole/h) | Specific activity (μmole/ h · mg prot) | % of control | % of inhibition |
|---|---|---|---|---|---|
| Control | 12340 | 0.35 | 87.00 | 100.00 | |
| Isomer A (10 μM final) | 8895 | 0.25 | 62.71 | 72.08 | 27.92 |
| Isomer B (10 μM final) | 7831 | 0.22 | 55.21 | 63.46 | 36.54 |
| Racemic mix A + B (10 μM final) | 10176 | 0.29 | 71.74 | 82.46 | 17.54 |

TABLE 8

Crystal data and structure refinement.

| | |
|---|---|
| Empirical formula | $C_{26}H_{32}N_2O_8$ |
| Formula weight | 500.54 |
| Temperature | 90(2) K |
| Wavelength | 0.71073 Å |
| Crystal system | Monoclinic |
| Space group | P2(1)/n |
| Unit cell dimensions | a = 16.7348(6) Å  α = 90° |
| | b = 7.8819(3) Å  β = 98.5090(10)° |
| | c = 18.5117(6) Å  γ = 90° |
| Volume | 2414.85(15) Å$^3$ |
| Z | 4 |
| Density (calculated) | 1.377 Mg/m$^3$ |
| Absorption coefficient | 0.102 mm$^{-1}$ |
| F(000) | 1064 |
| Crystal size | 0.38 × 0.20 × 0.10 mm$^3$ |
| Theta range for data collection | 2.22 to 32.63° |
| Index ranges | −25 <= h <= 24, −11 <= k <= 10, −27 <= l <= 25 |
| Reflections collected | 33322 |
| Independent reflections | 8434 [R(int) = 0.0372] |
| Completeness to theta = 32.63° | 95.7% |
| Absorption correction | Sadabs |
| Max. and min. transmission | 0.9898 and 0.9621 |
| Refinement method | Full-matrix least-squares on F$^2$ |
| Data/restraints/parameters | 8434/0/399 |
| Goodness-of-fit on F$^2$ | 1.021 |
| Final R indices [I > 2sigma(I)] | R1 = 0.0493, wR2 = 0.1210 |
| R indices (all data) | R1 = 0.0677, wR2 = 0.1309 |
| Largest diff. peak and hole | 0.431 and −0.272 e · Å$^{-3}$ |

TABLE 9

Atomic coordinates (×10$^4$) and equivalent isotropic displacement parameters (Å$^2$ × 10$^3$) U(eq) is defined as one third of the trace of the orthogonalized U$^{ij}$ tensor.

| | x | y | z | U(eq) |
|---|---|---|---|---|
| N(1) | 4187(1) | 505(1) | 7064(1) | 15(1) |
| N(2) | 2469(1) | 6526(1) | 7408(1) | 22(1) |
| O(1) | 4787(1) | 3926(1) | 7526(1) | 17(1) |
| O(2) | 8074(1) | 270(1) | 7914(1) | 30(1) |

TABLE 9-continued

Atomic coordinates (×10⁴) and equivalent isotropic displacement parameters ($Å^2 × 10^3$) U(eq) is defined as one third of the trace of the orthogonalized $U^{ij}$ tensor.

|       | x        | y        | z        | U(eq)  |
|-------|----------|----------|----------|--------|
| O(3)  | 7817(1)  | 1237(1)  | 6723(1)  | 25(1)  |
| O(4)  | 4067(1)  | 5361(1)  | 8264(1)  | 22(1)  |
| O(5)  | 6084(1)  | 1991(1)  | 5982(1)  | 19(1)  |
| O(6)  | 3737(1)  | 2797(1)  | 5250(1)  | 20(1)  |
| C(1)  | 4114(1)  | 4785(1)  | 7666(1)  | 16(1)  |
| C(2)  | 3536(1)  | 4844(1)  | 6994(1)  | 16(1)  |
| C(3)  | 2767(1)  | 5590(1)  | 6881(1)  | 17(1)  |
| C(4)  | 2330(1)  | 5387(2)  | 6178(1)  | 20(1)  |
| C(5)  | 2649(1)  | 4475(2)  | 5638(1)  | 20(1)  |
| C(6)  | 3433(1)  | 3771(2)  | 5762(1)  | 18(1)  |
| C(7)  | 3863(1)  | 3974(1)  | 6453(1)  | 15(1)  |
| C(8)  | 4689(1)  | 3349(1)  | 6771(1)  | 15(1)  |
| C(9)  | 4825(1)  | 1417(1)  | 6743(1)  | 14(1)  |
| C(10) | 5687(1)  | 1028(1)  | 7087(1)  | 15(1)  |
| C(11) | 6312(1)  | 1350(1)  | 6668(1)  | 16(1)  |
| C(12) | 7096(1)  | 1016(2)  | 6998(1)  | 19(1)  |
| C(13A)| 8410(5)  | 438(8)   | 7244(5)  | 32(1)  |
| C(13B)| 8434(13) | 880(20)  | 7355(13) | 43(4)  |
| C(14) | 7249(1)  | 432(2)   | 7708(1)  | 22(1)  |
| C(15) | 6658(1)  | 112(2)   | 8126(1)  | 23(1)  |
| C(16) | 5857(1)  | 420(2)   | 7800(1)  | 18(1)  |
| C(17) | 5150(1)  | 4(2)     | 8183(1)  | 22(1)  |
| C(18) | 4479(1)  | −737(2)  | 7633(1)  | 20(1)  |
| C(19) | 6648(1)  | 1882(2)  | 5474(1)  | 24(1)  |
| C(20A)| 3999(3)  | 3784(5)  | 4676(2)  | 27(1)  |
| C(20B)| 3831(7)  | 3420(13) | 4531(6)  | 34(2)  |
| C(21) | 4431(1)  | 2557(2)  | 4224(1)  | 28(1)  |
| O(7A) | 2204(2)  | 4414(3)  | 4960(2)  | 18(1)  |
| C(22A)| 1509(1)  | 3252(2)  | 4911(1)  | 18(1)  |
| C(23A)| 1771(2)  | 1542(3)  | 4685(2)  | 44(1)  |
| O(7B) | 2188(7)  | 3888(8)  | 4956(7)  | 28(2)  |
| C(22B)| 1726(6)  | 2260(20) | 5010(5)  | 93(5)  |
| C(23B)| 1508(4)  | 1574(8)  | 4304(4)  | 36(1)  |
| O(8A) | 1549(3)  | 6094(11) | 6050(4)  | 20(1)  |
| C(24A)| 1469(6)  | 7557(10) | 5574(5)  | 22(1)  |
| O(8B) | 1575(10) | 5820(30) | 6002(10) | 28(4)  |
| C(24B)| 1476(16) | 7230(30) | 5472(14) | 28(3)  |
| C(25) | 578(1)   | 7703(2)  | 5283(1)  | 29(1)  |
| C(26) | 3628(1)  | −354(2)  | 6496(1)  | 20(1)  |

TABLE 10

Bond lengths [Å] and angles [°].

| | | | |
|---|---|---|---|
| N(1)—C(26) | 1.4661(14) | N(1)—C(18) | 1.4673(15) |
| N(1)—C(9) | 1.4828(14) | N(2)—C(3) | 1.3728(16) |
| N(2)—HN1 | 0.885(18) | N(2)—HN2 | 0.96(2) |
| O(1)—C(1) | 1.3714(13) | O(1)—C(8) | 1.4559(14) |
| O(2)—C(13B) | 1.36(2) | O(2)—C(14) | 1.3841(13) |
| O(2)—C(13A) | 1.442(10) | O(3)—C(12) | 1.3866(14) |
| O(3)—C(13A) | 1.424(9) | O(3)—C(13B) | 1.47(2) |
| O(4)—C(1) | 1.2090(15) | O(5)—C(11) | 1.3678(14) |
| O(5)—C(19) | 1.4294(14) | O(6)—C(6) | 1.3759(14) |
| O(6)—C(20A) | 1.436(5) | O(6)—C(20B) | 1.448(12) |
| C(1)—C(2) | 1.4590(15) | C(2)—C(7) | 1.3898(16) |
| C(2)—C(3) | 1.4035(14) | C(3)—C(4) | 1.4036(17) |
| C(4)—O(8B) | 1.305(17) | C(4)—C(5) | 1.4000(18) |
| C(4)—O(8A) | 1.409(6) | C(5)—O(7A) | 1.361(4) |
| C(5)—C(6) | 1.4115(15) | C(5)—O(7B) | 1.454(11) |
| C(6)—C(7) | 1.3801(16) | C(7)—C(8) | 1.5043(14) |
| C(8)—C(9) | 1.5419(15) | C(9)—C(10) | 1.5197(14) |
| C(10)—C(16) | 1.3930(16) | C(10)—C(11) | 1.4144(15) |
| C(11)—C(12) | 1.3880(14) | C(12)—C(14) | 1.3810(18) |
| C(14)—C(15) | 1.3662(19) | C(15)—C(16) | 1.4065(15) |
| C(15)—H(15) | 0.9500 | C(16)—C(17) | 1.5032(17) |
| C(17)—C(18) | 1.5168(17) | C(20A)—C(21) | 1.529(5) |
| C(20B)—C(21) | 1.402(13) | O(7A)—C(22A) | 1.473(4) |
| C(22A)—C(23A) | 1.496(3) | O(7B)—C(22B) | 1.509(17) |
| C(22B)—C(23B) | 1.412(10) | O(8A)—C(24A) | 1.445(12) |
| C(24A)—C(25) | 1.512(10) | O(8B)—C(24B) | 1.47(3) |
| C(24B)—C(25) | 1.54(3) | | |
| C(26)—N(1)—C(18) | 108.46(9) | C(26)—N(1)—C(9) | 110.92(9) |
| C(18)—N(1)—C(9) | 115.39(8) | C(3)—N(2)—HN1 | 115.2(12) |
| C(3)—N(2)—HN2 | 114.0(11) | HN1-N(2)—HN2 | 116.8(16) |
| C(1)—O(1)—C(8) | 110.92(8) | C(13B)—O(2)—C(14) | 107.1(9) |
| C(14)—O(2)—C(13A) | 104.7(3) | C(12)—O(3)—C(13A) | 104.7(4) |
| C(12)—O(3)—C(13B) | 103.4(9) | C(11)—O(5)—C(19) | 117.87(9) |
| C(6)—O(6)—C(20A) | 113.09(18) | C(6)—O(6)—C(20B) | 123.1(5) |
| O(4)—C(1)—O(1) | 121.60(10) | O(4)—C(1)—C(2) | 130.14(10) |
| O(1)—C(1)—C(2) | 108.26(10) | C(7)—C(2)—C(3) | 123.33(10) |
| C(7)—C(2)—C(1) | 108.53(9) | C(3)—C(2)—C(1) | 128.12(11) |
| N(2)—C(3)—C(2) | 122.73(11) | N(2)—C(3)—C(4) | 121.72(10) |
| C(2)—C(3)—C(4) | 115.48(11) | O(8B)—C(4)—C(5) | 114.4(10) |
| O(8B)—C(4)—C(3) | 123.7(9) | C(5)—C(4)—C(3) | 121.34(10) |
| C(5)—C(4)—O(8A) | 121.6(3) | C(3)—C(4)—O(8A) | 117.0(3) |
| O(7A)—C(5)—C(4) | 117.59(17) | O(7A)—C(5)—C(6) | 120.30(18) |
| C(4)—C(5)—C(6) | 121.85(11) | C(4)—C(5)—O(7B) | 125.1(5) |
| C(6)—C(5)—O(7B) | 112.2(4) | O(6)—C(6)—C(7) | 120.53(9) |
| O(6)—C(6)—C(5) | 122.43(10) | C(7)—C(6)—C(5) | 116.79(11) |
| C(6)—C(7)—C(2) | 121.17(9) | C(6)—C(7)—C(8) | 130.40(10) |
| C(2)—C(7)—C(8) | 108.42(9) | O(1)—C(8)—C(7) | 103.86(8) |

TABLE 10-continued

Bond lengths [Å] and angles [°].

| | | | |
|---|---|---|---|
| O(1)—C(8)—C(9) | 110.19(9) | C(7)—C(8)—C(9) | 116.21(9) |
| N(1)—C(9)—C(10) | 115.37(9) | N(1)—C(9)—C(8) | 110.29(8) |
| C(10)—C(9)—C(8) | 108.67(8) | C(16)—C(10)—C(11) | 121.12(9) |
| C(16)—C(10)—C(9) | 121.03(10) | C(11)—C(10)—C(9) | 117.83(9) |
| O(5)—C(11)—C(12) | 126.46(10) | O(5)—C(11)—C(10) | 116.61(9) |
| C(12)—C(11)—C(10) | 116.92(10) | C(14)—C(12)—O(3) | 110.05(9) |
| C(14)—C(12)—C(11) | 120.74(11) | O(3)—C(12)—C(11) | 129.17(11) |
| O(3)—C(13A)—O(2) | 107.6(5) | O(2)—C(13B)—O(3) | 109.6(14) |
| C(15)—C(14)—C(12) | 123.63(10) | C(15)—C(14)—O(2) | 127.12(12) |
| C(12)—C(14)—O(2) | 109.24(11) | C(14)—C(15)—C(16) | 116.61(11) |
| C(10)—C(16)—C(15) | 120.97(11) | C(10)—C(16)—C(17) | 117.20(9) |
| C(15)—C(16)—C(17) | 121.72(11) | C(16)—C(17)—C(18) | 108.89(10) |
| N(1)—C(18)—C(17) | 111.09(10) | O(6)—C(20A)—C(21) | 106.4(3) |
| C(21)—C(20B)—O(6) | 113.0(7) | C(5)—O(7A)—C(22A) | 113.4(3) |
| O(7A)—C(22A)—C(23A) | 108.44(19) | C(5)—O(7B)—C(22B) | 115.0(8) |
| C(23B)—C(22B)—O(7B) | 109.2(9) | C(4)—O(8A)—C(24A) | 114.7(6) |
| O(8A)—C(24A)—C(25) | 106.0(6) | C(4)—O(8B)—C(24B) | 112.0(16) |
| O(8B)—C(24B)—C(25) | 110.1(18) | | |

TABLE 11

Anisotropic displacement parameters (Å$^2$ × 10$^3$). The anisotropic displacement factor exponent takes the form:
$-2\pi^2[h^2a^{*2}U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| N(1) | 15(1) | 14(1) | 16(1) | 1(1) | 4(1) | −2(1) |
| N(2) | 19(1) | 20(1) | 29(1) | 1(1) | 10(1) | 3(1) |
| O(1) | 16(1) | 16(1) | 19(1) | −2(1) | 1(1) | 1(1) |
| O(2) | 17(1) | 36(1) | 35(1) | −1(1) | −6(1) | 8(1) |
| O(3) | 12(1) | 27(1) | 36(1) | 3(1) | 2(1) | 2(1) |
| O(4) | 26(1) | 20(1) | 21(1) | −3(1) | 5(1) | 0(1) |
| O(5) | 15(1) | 23(1) | 19(1) | 5(1) | 5(1) | 3(1) |
| O(6) | 22(1) | 22(1) | 17(1) | 1(1) | 5(1) | 2(1) |
| C(1) | 17(1) | 13(1) | 21(1) | 0(1) | 4(1) | −1(1) |
| C(2) | 14(1) | 14(1) | 20(1) | 2(1) | 3(1) | 0(1) |
| C(3) | 15(1) | 15(1) | 23(1) | 4(1) | 7(1) | 1(1) |
| C(4) | 13(1) | 23(1) | 24(1) | 8(1) | 5(1) | 3(1) |
| C(5) | 14(1) | 27(1) | 19(1) | 6(1) | 2(1) | 1(1) |
| C(6) | 15(1) | 20(1) | 18(1) | 2(1) | 3(1) | 1(1) |
| C(7) | 13(1) | 14(1) | 18(1) | 3(1) | 3(1) | 1(1) |
| C(8) | 13(1) | 14(1) | 17(1) | 1(1) | 2(1) | 0(1) |
| C(9) | 13(1) | 14(1) | 15(1) | 1(1) | 2(1) | 0(1) |
| C(10) | 14(1) | 13(1) | 17(1) | −1(1) | 1(1) | 2(1) |
| C(11) | 15(1) | 14(1) | 19(1) | 0(1) | 1(1) | 2(1) |
| C(12) | 14(1) | 16(1) | 27(1) | 0(1) | 2(1) | 2(1) |
| C(13A) | 14(1) | 36(2) | 45(2) | 5(2) | −3(1) | 5(1) |
| C(13B) | 16(3) | 64(10) | 45(8) | 23(7) | −3(4) | −2(7) |
| C(14) | 17(1) | 19(1) | 28(1) | −3(1) | −5(1) | 5(1) |
| C(15) | 24(1) | 23(1) | 19(1) | 1(1) | −3(1) | 6(1) |
| C(16) | 21(1) | 17(1) | 16(1) | −1(1) | 1(1) | 4(1) |
| C(17) | 25(1) | 24(1) | 16(1) | 4(1) | 3(1) | 4(1) |
| C(18) | 24(1) | 17(1) | 19(1) | 3(1) | 7(1) | 0(1) |
| C(19) | 22(1) | 31(1) | 23(1) | 1(1) | 10(1) | 4(1) |
| C(20A) | 42(2) | 18(1) | 24(2) | −5(1) | 18(1) | −4(1) |
| C(20B) | 46(5) | 34(6) | 23(5) | 13(4) | 10(3) | 19(4) |
| C(21) | 34(1) | 25(1) | 28(1) | −3(1) | 14(1) | 0(1) |
| O(7A) | 14(1) | 21(1) | 18(1) | 3(1) | 0(1) | −2(1) |
| C(22A) | 11(1) | 17(1) | 24(1) | 4(1) | −1(1) | 2(1) |
| C(23A) | 35(1) | 28(1) | 67(2) | −2(1) | 3(1) | −2(1) |
| O(7B) | 25(2) | 32(4) | 23(2) | 6(4) | −5(2) | 2(3) |
| C(22B) | 55(5) | 191(16) | 36(5) | −50(8) | 13(4) | −42(8) |
| C(23B) | 30(3) | 25(3) | 54(4) | 5(3) | 9(3) | 4(2) |
| O(8A) | 10(1) | 24(2) | 26(1) | 7(1) | 4(1) | 8(1) |
| C(24A) | 19(1) | 22(2) | 25(2) | 9(1) | 8(1) | 7(2) |
| O(8B) | 26(3) | 28(7) | 36(5) | 24(5) | 22(3) | 18(3) |
| C(24B) | 16(3) | 35(9) | 36(8) | 13(5) | 10(5) | 14(5) |
| C(25) | 20(1) | 36(1) | 29(1) | 11(1) | 3(1) | 9(1) |
| C(26) | 19(1) | 19(1) | 20(1) | −3(1) | 4(1) | −5(1) |

TABLE 12

Hydrogen coordinates (×10$^4$) and isotropic displacement parameters (Å$^2$ × 10$^3$)

| | x | y | z | U(eq) |
|---|---|---|---|---|
| H(8) | 5100 | 3931 | 6517 | 18 |
| H(9) | 4772 | 1086 | 6216 | 17 |
| H(13A) | 8908 | 1134 | 7326 | 39 |
| H(13B) | 8548 | −692 | 7065 | 39 |
| H(13C) | 8822 | 31 | 7219 | 51 |
| H(13D) | 8735 | 1929 | 7510 | 51 |
| H(15) | 6781 | −297 | 8613 | 27 |
| H(17A) | 4958 | 1043 | 8403 | 26 |
| H(17B) | 5315 | −825 | 8579 | 26 |
| H(18A) | 4682 | −1755 | 7405 | 24 |
| H(18B) | 4026 | −1091 | 7888 | 24 |
| H(19A) | 7125 | 2571 | 5650 | 37 |
| H(19B) | 6395 | 2304 | 4997 | 37 |
| H(19C) | 6810 | 698 | 5428 | 37 |
| H(20A) | 4372 | 4694 | 4884 | 32 |
| H(20B) | 3530 | 4311 | 4369 | 32 |
| H(20C) | 3310 | 3304 | 4204 | 41 |
| H(20D) | 3968 | 4642 | 4567 | 41 |
| H(21A) | 4626 | 3178 | 3826 | 42 |
| H(21B) | 4054 | 1669 | 4020 | 42 |
| H(21C) | 4890 | 2039 | 4537 | 42 |
| H(21D) | 4421 | 1412 | 4429 | 42 |
| H(21E) | 4993 | 2921 | 4235 | 42 |
| H(21F) | 4157 | 2551 | 3718 | 42 |
| H(22A) | 1061 | 3682 | 4548 | 21 |
| H(22B) | 1317 | 3174 | 5391 | 21 |
| H(23A) | 1988 | 1642 | 4223 | 66 |
| H(23B) | 1306 | 771 | 4620 | 66 |
| H(23C) | 2189 | 1093 | 5063 | 66 |
| H(22C) | 2065 | 1440 | 5324 | 112 |
| H(22D) | 1234 | 2489 | 5234 | 112 |
| H(23D) | 1148 | 2365 | 4004 | 54 |
| H(23E) | 1229 | 490 | 4339 | 54 |
| H(23F) | 1995 | 1390 | 4079 | 54 |
| H(24A) | 1786 | 7400 | 5168 | 26 |
| H(24B) | 1662 | 8592 | 5849 | 26 |
| H(24C) | 1689 | 6883 | 5022 | 34 |
| H(24D) | 1788 | 8224 | 5681 | 34 |
| H(25A) | 489 | 8679 | 4953 | 43 |
| H(25B) | 273 | 7859 | 5691 | 43 |
| H(25C) | 396 | 6666 | 5017 | 43 |
| H(25D) | 283 | 6790 | 5488 | 43 |
| H(25E) | 499 | 7611 | 4750 | 43 |
| H(25F) | 376 | 8803 | 5424 | 43 |
| H(26A) | 3915 | −1252 | 6274 | 29 |
| H(26B) | 3411 | 469 | 6121 | 29 |
| H(26C) | 3183 | −852 | 6714 | 29 |
| HN1 | 1937(11) | 6530(20) | 7378(10) | 39(3) |
| HN2 | 2775(11) | 6410(20) | 7888(11) | 39(3) |

TRQ or TRQ+Montelukast® Treatment of Food Allergies in Patients

In the following examples (EXAMPLES 4-6) baseline patients with food allergies treated with Tritoqualine alone or Montelukast® alone (Singulair®) did not yield satisfactory management of food allergy symptoms. The patients with food allergies described below demonstrate a synergic and surprising effect with the drug combination of Tritoqualine and Montelukast®. Allergens tested came from either STALLERGENES, or ALLERBIO.

Example 4

TRQ+Montelukast® Treatment of Nut Allergy in a Patient

A pediatric patient had a history of anaphylaxis due to nut allergy (hazelnut/peanut) caused by ingestion of a hazelnut flavored cocoa spread marketed as "Nutella®". The direct test with the Nutella® was strongly positive for allergy. This patient was hospitalized in two occasions for the same dramatic allergic reaction to Nutella® spread. Furthermore, the patient presented allergies to pneumoallergens.

The patient underwent anti-allergic treatment that did not modify his reaction to nut allergens. The second hospitalization occurred while the patient was under H1 antagonist and cromoglycate.

After treatment with a composition of the present invention containing the combination of Montelukast® at the dose of 10 mg daily and Tritoqualine at the dose of 200 mg daily for a period of six weeks, it was possible to re-introduce the causal agent (Nutella® spread) to the patient without any major allergic reaction. Further, continuing the aforementioned treatment for six months, the patient was able to eat more than 5 spoons of Nutella® spread without any noticeable allergic reaction. Digestive symptoms associated with this patient's allergy (stomach pain, diarrhea, constipation) completely disappeared after the treatment with the combination of Tritoqualine and Montelukast®. Continuation of the above treatment for over 8 months afforded reversal of allergic and digestive symptoms due to food allergy.

Example 5

TRQ+Montelukast® Treatment of Shrimp Allergy in a Patient

The patient under study had survived two cases of anaphylactic shock due to ingestion of shrimps. Each case of anaphylaxis resulted in hospitalization. Treatment with the composition of the invention containing a combination of Tritoqualine 200 mg and Montelukast® 10 mg for six weeks afforded gradual reintroduction of the allergenic food without symptoms of allergy. The first shrimp did not generate any local signs. Later the patient was able to ingest five shrimps without any local signs and no global reaction.

Example 6

TRQ+Montelukast® Treatment of Food Allergies in Patients

Baseline patients had signs of food allergies and the food allergy symptoms were not adequately managed with an H1 antagonist and cromoglycate. A group of 15 patients presenting signs of food allergies is tested with allergens such as the following: peanut, milk, tomato, potato, flour of wheat, soybean, fish, and shrimp. Allergens tested came from either STALLERGENES, or ALLERBIO.

All patients had history of hospitalization and reactions such as Quincke's edema and asthma crisis. Most of the causal allergens were peanut (six patients), egg (four patients) and soybean (five patients) of them (with other several positive food allergens at different degrees of reaction). The patients presenting loco-regional reactions to food allergens after ingestion were treated with a composition of the invention containing the combination of Tritoqualine and Montelukast®.

Treatment with Tritoqualine 200 mg with 10 mg of Montelukast® for 6 to 8 weeks afforded gradual reintroduction of the causal allergen without major allergic symptoms. One patient with a history of peanut allergy after 8 weeks of treatment presented a mild local reaction (itching of the lips). At 8 months of treatment the reintroduction of peanut did not cause local or general symptoms.

Example 7

TRQ+Loratadine Treatment of COPD in a Patient

In this study, the baseline patient was a 64 year old male with a COPD history. The COPD history of this patient extended 1 year of treatment prior to the initial visit (T0) and presented an average of eight hospitalization days per month due to complications of COPD.

At the initial visit to the physician (T0), the patient was examined and the spirometry parameter FEV1 was recorded. Tritoqualine 200 mg/day and Loratadine 10 mg/day were added to the patient's existing drug therapy. The patient had undergone physician examinations: 6 weeks, 6 months and 10 months after the start of the Tritoqualine/Loratadine treatment (T0). During each visit the patient's overall health and the FEV1 parameter was assessed by spirometry. Results from each visit are illustrated in Table 13.

TABLE 13

| Spirometry Parameter (L/s) | T0 (initial visit) | T2 (6 weeks) | T3 (6 months) | T4 (10 month) |
|---|---|---|---|---|
| FEV1 | 0.4 | 0.6 | 0.8 | 0.9 |
| FEV1 Normal value* | 3.2 | 3.2 | 3.2 | 3.2 |

*Normal Value is a value expected for healthy individuals based on age, and height During the period of treatment the patient showed improvement as evidenced by the fact that no hospitalization was necessary during the treatment period. Thus hospitalization decreased from an average of eight days per month to no hospitalization days at all. Further, the spirometry parameter FEV1 increased by 125% (from 0.4-0.9) during the 10 month treatment period, indicating improvement.

Therefore, the additional therapy, Tritoqualine 200 mg/day and Loratadine 10 mg/day ameliorated the COPD symptoms of the patient by significantly decreasing the frequency of hospitalization and improving the spirometry parameter FEV1 by 125% (0.5 L/s in 10 months).

Example 8

TRQ+Loratadine Treatment of COPD in a Patient

The baseline patient in this study was a 60 year old male with a COPD history that extended 2 years of treatment prior to the initial visit (T0).

At the initial visit to the physician (T0), the patient was examined and the spirometry parameter FEV1 was recorded. Tritoqualine 200 mg/day and Loratadine 10 mg/day were added to the patient's existing drug therapy. The patient had undergone physician examinations: 6 weeks, 6 months and 8 months after the start of the Tritoqualine/Loratadine treatment (T0). During each visit the patient's overall health and the FEV1 parameter was assessed by spirometry. Results from each visit are illustrated in Table 14.

TABLE 14

| Spirometry Parameter | T0 (initial visit) | T2 (6 weeks) | T3 (6 months) | T4 (8 month) |
|---|---|---|---|---|
| FEV1 (L/s) | 1.4 | 1.7 | 2.1 | 2.4 |
| FEV1 Normal value* (L/s) | 3.8 | 3.8 | 3.8 | 3.8 |

*Normal Value is a value expected for healthy individuals based on age, and height.

During the period of treatment the patient showed improvement as evidenced by an increase in the spirometry parameter FEV1, which increased by 71.4% (from 1.4-2.4) during the 8 month treatment period.

Therefore, the additional therapy, Tritoqualine 200 mg/day and Loratadine 10 mg/day, ameliorated the COPD symptoms of the patient by significantly improving the spirometry parameter FEV1 by 71.4% (1.0 L/s in 8 months).

Example 9

TRQ+Loratadine Treatment of COPD in a Patient

The baseline patient in this study was a 68 year old male with a COPD history that extended 3 years of treatment prior to the initial visit (T0).

At the initial visit to the physician (T0), the patient was examined and the spirometry parameter FEV1 was recorded. Tritoqualine 200 mg/day and Loratadine 10 mg/day were added to the patient's existing drug therapy. The patient had undergone physician examinations: 6 weeks, and 8 months after the start of the Tritoqualine/Loratadine treatment (T0). During each visit the patient's overall health and the FEV1 parameter was assessed by spirometry. Results from each visit are illustrated in Table 15.

TABLE 15

| Spirometry Parameter | T0 (initial visit) | T2 (6 weeks) | T3 (6 months) |
|---|---|---|---|
| FEV1 (L/s) | 1.2 | 1.8 | 1.9 |
| FEV1 Normal value* (L/s) | 3.8 | 3.8 | 3.8 |

*Normal Value is a value expected for healthy individuals based on age, and height.

During the period of treatment the patient showed improvement as evidenced by an increase in the spirometry parameter FEV1 increased by 58.3% (from 1.2-1.9) during the 8 month treatment period.

Therefore, the additional therapy, Tritoqualine 200 mg/day and Loratadine 10 mg/day, ameliorated the COPD symptoms of the patient by significantly improving the spirometry parameter FEV1 by 58.3% (0.7 L/s in 8 months).

Example 10

TRQ+Loratadine Treatment of COPD in a Patient

The baseline patient in this study was a 58 year old male with a COPD history that extended 3 years of treatment prior to the initial visit (T0).

At the initial visit to the physician (T0), the patient was examined and the spirometry parameter FEV1 was recorded. Tritoqualine 200 mg/day and Loratadine 10 mg/day were added to the patient's existing drug therapy. The patient had undergone physician examinations: 6 weeks, 6 months, and 12 months after the start of the Tritoqualine/Loratadine treatment (T0). During each visit the patient's overall health and the FEV1 parameter was assessed by spirometry. Results from each visit are illustrated in Table 16.

TABLE 16

| Spirometry Parameter | T0 (initial visit) | T2 (6 weeks) | T3 (6 months) | T4 (12 months) |
|---|---|---|---|---|
| FEV1 (L/s) | 1.8 | 2.1 | 2.1 | 2.6 |
| FEV1 Normal value* (L/s) | 3.1 | 3.1 | 3.1 | 3.1 |

*Normal Value is a value expected for healthy individuals based on age, and height.

During the period of treatment the patient showed improvement as evidenced by the increase in the spirometry parameter FEV1, which increased by 100.0% (from 1.8-2.6) during the 12 month treatment period.

Therefore, the additional therapy Tritoqualine 200 mg/day and Loratadine 10 mg/day ameliorated the COPD symptoms of the patient by significantly improving the spirometry parameter FEV1 by 44.4% (0.8 L/s in 12 months).

Example 11

TRQ+Loratadine Treatment of COPD in a Patient

The baseline patient in this study was a 67 year old male with a COPD history that extended 2 years of treatment prior to the initial visit (T0).

At the initial visit to the physician (T0), the patient was examined and the spirometry parameter FEV1 was recorded. Tritoqualine 200 mg/day and Loratadine 10 mg/day were added to the patient's existing drug therapy. The patient had undergone physician examinations: 8 weeks, 4 months, and 8 months after the start of the Tritoqualine/Loratadine treatment (T0). During each visit the patient's overall health and the FEV1 parameter was assessed by spirometry. Results from each visit are illustrated in Table 17.

TABLE 17

| Spirometry Parameter | T0 (initial visit) | T2 (6 weeks) | T3 (6 months) | T4 (12 months) |
|---|---|---|---|---|
| FEV1 (L/s) | 1.5 | 1.7 | 1.9 | 2.0 |
| FEV1 Normal value* (L/s) | 3.2 | 3.2 | 3.2 | 3.2 |

*Normal Value is a value expected for healthy individuals based on age, and height.

During the period of treatment the patient showed improvement as evidenced by the increase in the spirometry parameter FEV1, which increased by 100.0% (from 1.5-2.0) during the 8 month treatment period.

Therefore, the additional therapy, Tritoqualine 200 mg/day and Loratadine 10 mg/day, ameliorated the COPD symptoms of the patient by significantly improving the spirometry parameter FEV1 by 33.3% (0.5 L/s in 8 months).

The treatment with a combination of a histidine decarboxylase inhibitor such as Tritoqualine 200 mg/day and an anti-H1 drug such as Loratadine 10 mg/day dramatically ameliorated symptoms of COPD as shown by the respiratory parameter FEV1 and the decrease of the need of hospitalization.

Example 12

TRQ+Existing Treatment of COPD in Patients 13 patients (38-84 years of age; nine male and four female) were examined by a physician and their condition of COPD was assessed. The doctor did not remove other medications previously taken from the patient, even though the patient was not responding well with those medications.

At the initial visit to the physician (T0), the patients were examined and the spirometry parameter FEV1 was recorded. Tritoqualine 200 mg/day were added to the patient's existing drug therapy. The patients had undergone physician examination on a second visit (T1) 6-8 weeks after the start of the Tritoqualine treatment. During each visit the patient's overall health and the FEV1 parameter was assessed by spirometry. Results from each visit are illustrated in Table 18.

TABLE 18

| Patient # | Expected Normal FEV-1 value* | T0 (initial visit) FEV1 | % Deviation from the expected normal value. | T2 (6-8 weeks follow-up visit) FEV1 normalized | % Deviation from the expected normal value |
|---|---|---|---|---|---|
| patient 1 | 1.8 | 1.30 | 72.22% | 1.60 | 88.89% |
| patient 2 | 2.15 | 1.86 | 86.51% | 2.26 | 105.12% |
| patient 3 | 1.97 | 1.00 | 50.76% | 1.00 | 50.76% |
| patient 4 | 2.66 | 2.39 | 89.85% | 2.60 | 97.74% |
| patient 5 | 3.93 | 1.86 | 47.33% | 3.36 | 85.50% |
| patient 6 | 2.09 | 1.60 | 76.56% | 1.50 | 71.77% |
| patient 7 | 2.13 | 1.53 | 71.83% | 1.98 | 92.96% |
| patient 8 | 2.63 | 1.64 | 62.36% | 1.90 | 72.24% |
| patient 9 | 1.35 | 1.00 | 74.07% | 1.18 | 87.41% |
| patient 10 | 2.45 | 1.32 | 53.88% | 1.59 | 64.90% |
| patient 11 | 1.52 | 0.82 | 53.95% | 1.04 | 68.42% |
| patient 12 | 1.7 | 0.58 | 34.12% | 0.74 | 43.53% |
| patient 13 | 2.72 | 2.28 | 83.82% | 2.40 | 88.24% |

*Normal Value is a value expected for healthy individuals based on age, and height according to American thoracic Society.

Figure 7:
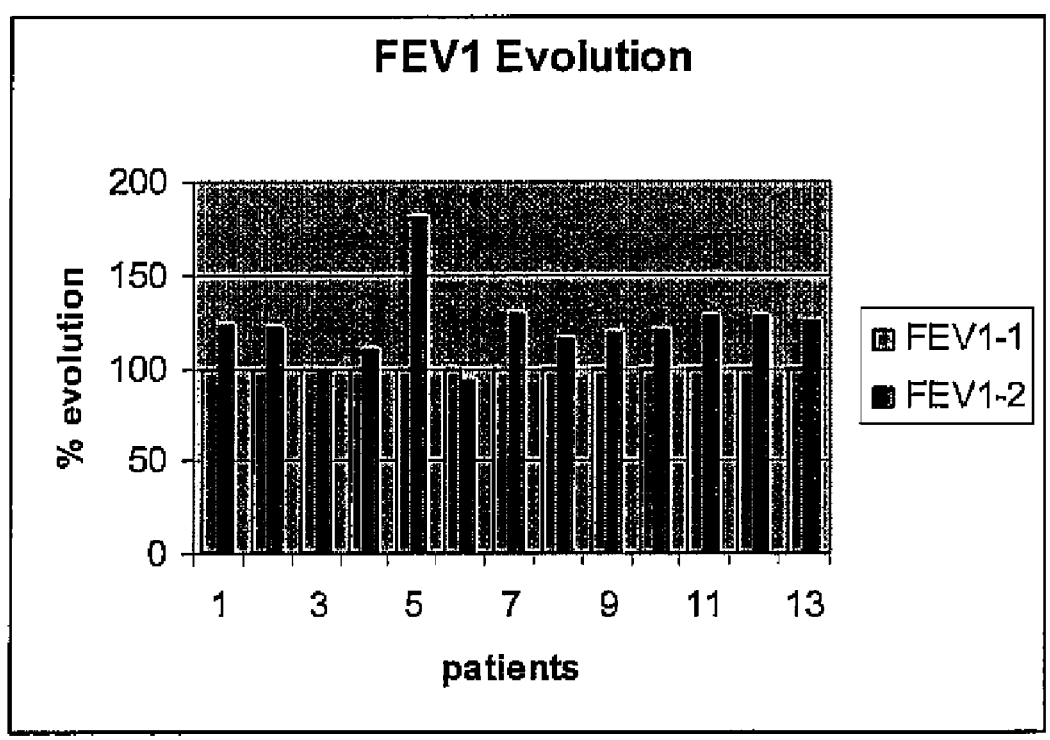
FIG. 7 shows the % improvement for each patient from the visit T0 to visit T1 as described in Example 12. Statistical analysis using a paired t-test on the values generated on visits T0 and T1 showed a statistically significant improvement due to Tritoqualine treatment. P-value for the paired t-test P=0.0012 calculated using GraphPad Prism®, as described in Example 3, below.

Based upon the data illustrated on Table 18, there was a significant improvement in the FEV1 parameter for at least 11 patients, one patient showed no improvement and one showed slight deterioration. FIG. 7 and Table 19 show the % improvement for each patient from the visit T0 to visit T1. Statistical analysis using a paired t-test on the values generated on visits T0 and T1 showed a statistically significant improvement due to Tritoqualine treatment. The P-value for the paired t-test P=0.0012 was calculated using GraphPad Prism.

TABLE 19

|  | Visit T0 | Visit T1 |
|---|---|---|
| Mean | 65.3 | 77.69 |
| Standard Deviation | 16.81 | 18.27 |
| Standard error of the mean | 4.66 | 5.07 |
| N | 13 | 13 |

Example 13

TRQ Effect on H4R+ Human TF1 Cells, Demonstrating that TRQ has Agonist Action on H4R Tritoqualine was tested on a cell proliferation assay using human TF1 cells that express H4R.

TF1 cell proliferation is promoted using granulocyte/macrophage colony-stimulating factor (GM-CSF). In this cell proliferation model H4R agonists inhibit cell proliferation. Clobenpropit (CB), a known H4R agonist at a dose of $10^{-5}$M (10 µM) was used as a known cell proliferation inhibition control. Tritoqualine (racemic mixture: TRQ) was used at doses between $10^{-5}$ M (10 µM) and $10^{-7}$ M (0.1 µM) and the potency of inhibition of cell proliferation was compared to CB $10^{-5}$M (10 µM). Each experiment used 100,000 TF1 cells/mL incubated for three days with GM-CSF (10 ng/mL). After addition of TRQ in the range of $10^{-5}$M (10 µM) to $10^{-7}$ M (0.1 µM), and incubation for 3 days, cell proliferation was assessed and compared to that of 10 µM CB.

Figure 8:
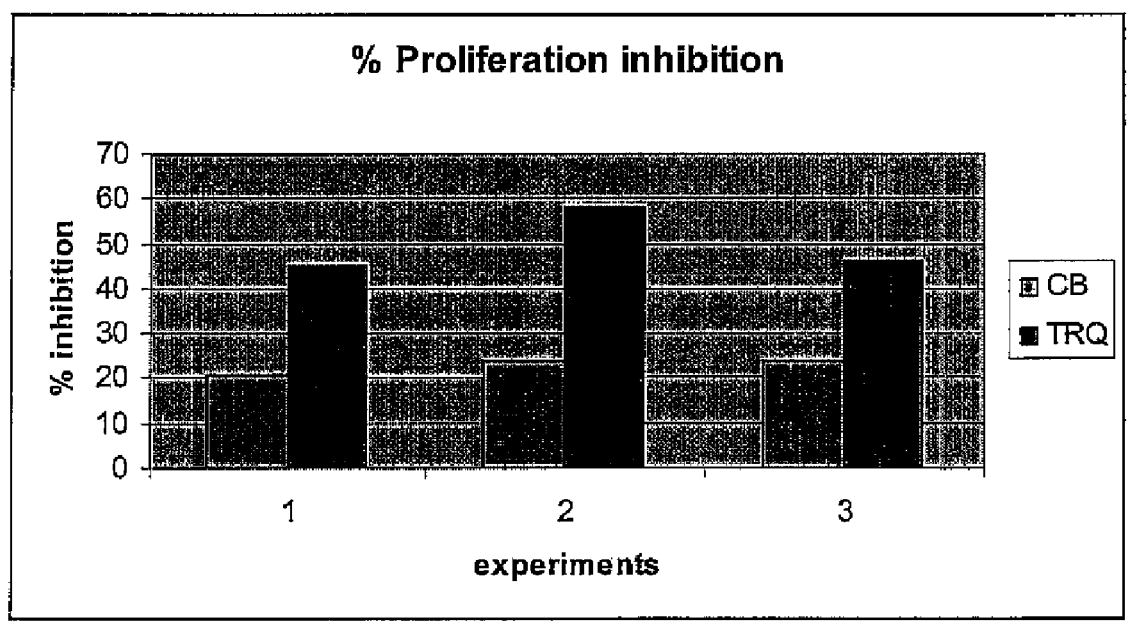
FIG. 8 shows the results of a cell proliferation assay using human TF1 cells that express H4R. When 10 μM TRQ and 10 μM CB were compared in three separate assays (n=3), TRQ was found to be superior, more potent inhibitor of cell proliferation than CB (approximately double the potency of CB). Average inhibition of cell proliferation by CB and TRQ was found to be 23% and 49%, respectively, as described in Example 13.

Results and Discussion: When 10 µM TRQ and 10 µM CB were compared in three separate assays (n=3), TRQ was found to be a superior, more potent inhibitor of cell proliferation than CB (approximately double the potency of CB). Average inhibition of cell proliferation by CB and TRQ was found to be 23% and 49%, respectively. Results are illustrated in FIG. 8. In addition to the above experiment, TRQ, at concentration $10^{-6}$ M (1 µM) inhibited cell proliferation by 18%. TRQ at $10^{-7}$ (0.1 µM) demonstrated no inhibition of cell proliferation.

Example 14

TRQ or TRQ+CB Effect on H4R+ Human TF1 Cells Demonstrating that TRQ has Agonist Action on H4R Comparison between TRQ alone and, in association with Clobenpropit (TRQ+CB) on the inhibition of human TF1 cell proliferation assay; both TRQ and CB were used each, at 10 µM concentration.

Figure 9:
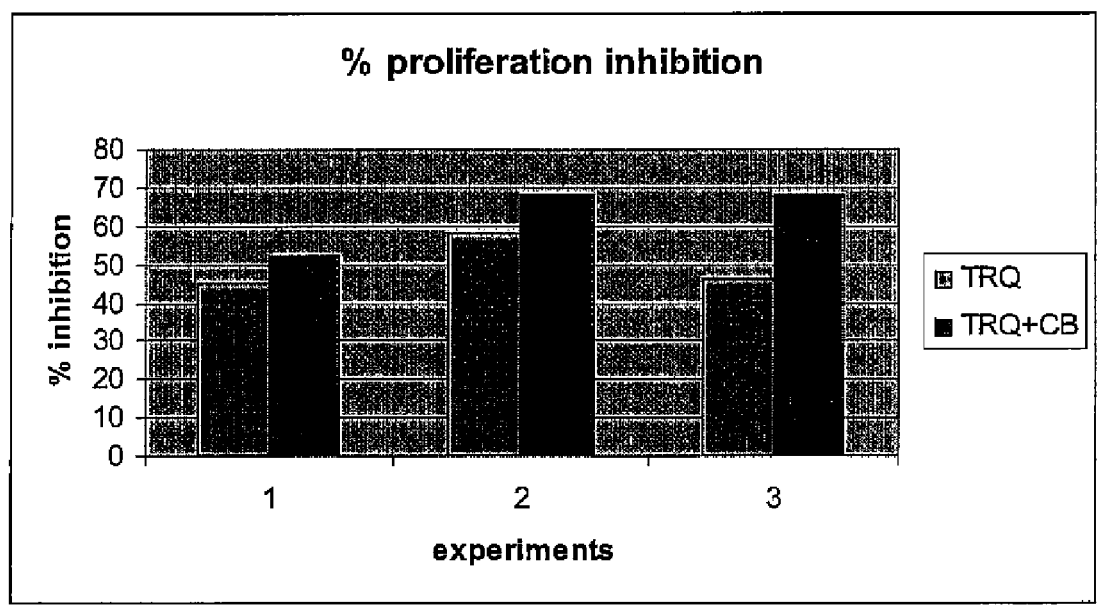
FIG. 9 shows a comparison between TRQ alone and, in association with Clobenpropit (TRQ+CB) on the inhibition of human TF1 cell proliferation assay; both TRQ and CB were used each, at 10 μM concentration. TRQ and Clobenpropit in 50:50-mixture produced a more potent inhibition of cell proliferation compared to Tritoqualine alone. This suggests that TRQ and CB demonstrate an additive effect on the inhibition of cell proliferation on TF1 cells, as described in Example 14.

TRQ and Clobenpropit in 50:50-mixture produced a more potent inhibition of cell proliferation compared to Tritoqualine alone. This suggests that TRQ and CB demonstrate an additive effect on the inhibition of cell proliferation on TF1 cells as shown in FIG. 9.

Example 15

Analysis of the Cell Cycle of Haematopoietic Progenitor Cells to Test Tritoqualine Enantiomers Demonstrating that TRQ Enantiomers have Agonist Action on H4R The enantiomers of TRQ E1 and E2 ($10^{-5}$ M (10 µM)) were tested for inhibition of cell cycle according to the following procedure on Colony Forming Cells (CFC, mouse medullary cells C57B1/6) expressing H4R.

Haematopoietic progenitor cells were incubated for 1-3 day(s) with a cocktail of growth factors (IL-3, 10 ng/ml, IL-6 10 ng/ml), Fetal Calf Serum (FCS) (50 ng/ml) in the culture medium StemSpan® (without serum) in the presence and absence of TRQ and H4R antagonist (JNJ7777120, Sigma Aldrich).

Cells were later stained with propidium iodide (PI) for the analysis of the cell cycle according to the following protocol: $2 \times 10^6$ cells/ml were labelled with CD1 17-FITC for 20 min in PBS, then washed in PBS and stained with PBS 1% formaldehyde, without methanol, at 4° C. for 5 min and again washed in PBS.

The cells were then lysed with 1 ml of PVTritonX100 and RNAse without DNAse (0.2 mcg/ml), PI (20 mcg/ml), and incubated in PBS for 30 min at ambient temperature.

The lysed cells were analyzed with FACS scan (FL2-area IFL2-width) for cell cycle analysis and FL1 for labelling of cell Surface.
Staining with the CFSE $10^6$ cells enriched in haematopoietic stem cells were incubated in 2 ml of CFSE 5 mmol in PBS 10 min, 37° C. The reaction was stopped by the addition of cold PBS in excess (5×) and centrifuged for 5 min at 1700 rpm.

Cells were resuspended in the culture medium StemSpan® (without serum) and stimulated with the growth Factor cocktail, and analyze in FACs scan (FL1) after 72 hours incubation.

The E2 enantiomer of TRQ inhibits the proliferation of the Colony Forming Cells (CFC, mouse medullary cells C57B1/6) expressing H4R by the blocking the cellular cycle in phase G0/G1 due to the activation of the H4 receptor.

Figure 11:
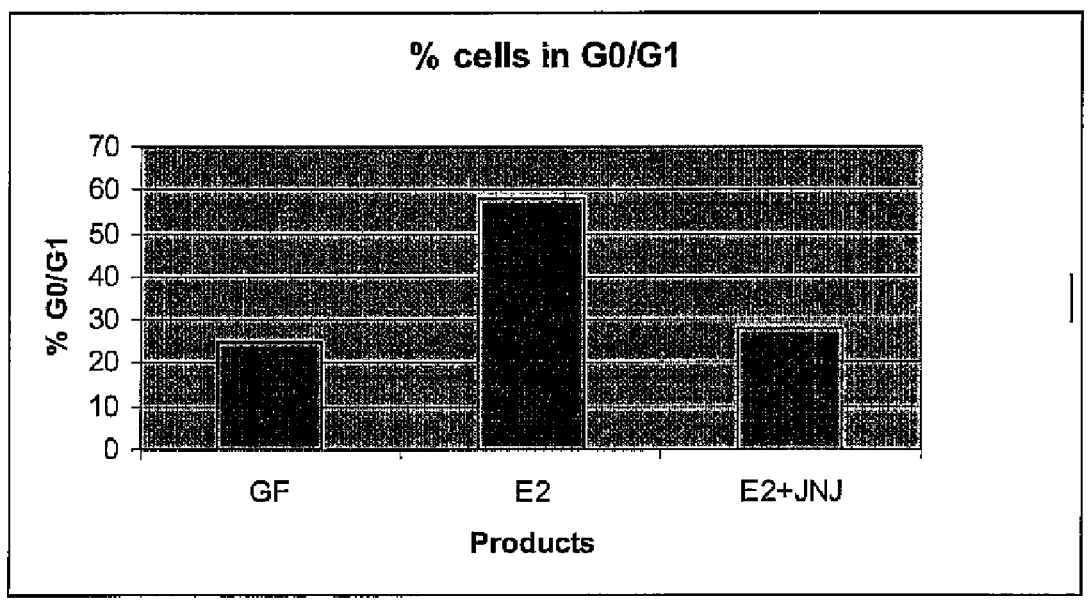
FIG. 11 shows the effects of E2 enantiomer on a cell assay using mouse medullary cells C57B1/6 expressing H4R. Approximately 60% of haematopoietic progenitor cells are blocked by E2 enantiomer of Tritoqualine. This G0/G1 blocking of the cell cycle is reversed if a known H4R antagonist such as JNJ7777120 is used, suggesting that the inhibition of cell proliferation is due to activation of the H4R, as described in Example 15.

Approximately 60% of haematopoietic progenitor cells were blocked by the E2 enantiomer of Tritoqualine (FIG. 11). This G0/G1 blocking of the cell cycle is reversed if a known H4R antagonist such as JNJ7777120 is used; suggesting that the inhibition of cell proliferation is due to activation of the H4R.

The E1 enantiomer of TRQ inhibits the proliferation of the Colony Forming Cells (CFC, mouse medullary cells C57B1/6) expressing H4R, by blocking the cellular cycle in phase G0/G1 to the activation of the H4 receptor.

Figure 12:
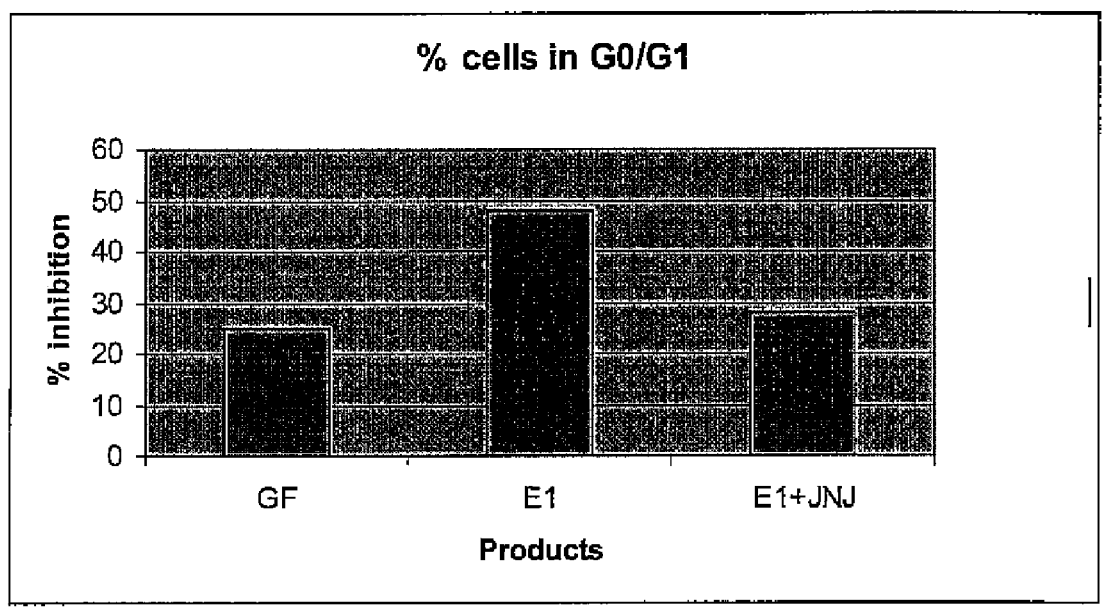
FIG. 12 shows the effects of E1 enantiomer on a cell assay using mouse medullary cells C57B1/6 expressing H4R. Approximately 48% of haematopoietic progenitor cells are blocked by the E1 enantiomer of Tritoqualine. This G0/G1 blocking of the cell cycle is reversed if a known H4R antagonist such as JNJ7777120 is used suggesting that the inhibition of cell proliferation is due to activation of the H4R, as described in Example 15.

Approximately 48% of haematopoietic progenitor cells were blocked by the E1 enantiomer of Tritoqualine (FIG. 12). This G0/G1 blocking of the cell cycle is reversed, if a known H4R antagonist such as JNJ7777120 is used; suggesting that the inhibition of cell proliferation is due to activation of the H4R.

These results demonstrate that the E1 enantiomer may be a better inhibitor of cell cycle than the enantiomer E2.

Example 16

TRQ or CB Inhibition of Proliferation of Colony Forming Cells (CFC) Demonstrating that TRQ has Agonist Action on H4R Using the assay described in Example 15, above, the effect of TRQ or CB on cells expressing H4R was tested. Mouse medullary cells C57B1/6 expressing H4R (50,000 cells/Petri dish) were incubated in a semi-solid media with haematopoietic growth factors (IL-3: 10 ng/ml) for 7 days with TRQ or CB. In this test CB inhibits the proliferation of CFC at the classic dose of $10^{-5}$M (10 μM) and was compared to TRQ at the dose of $10^{-5}$M (10 μM).

Figure 10:
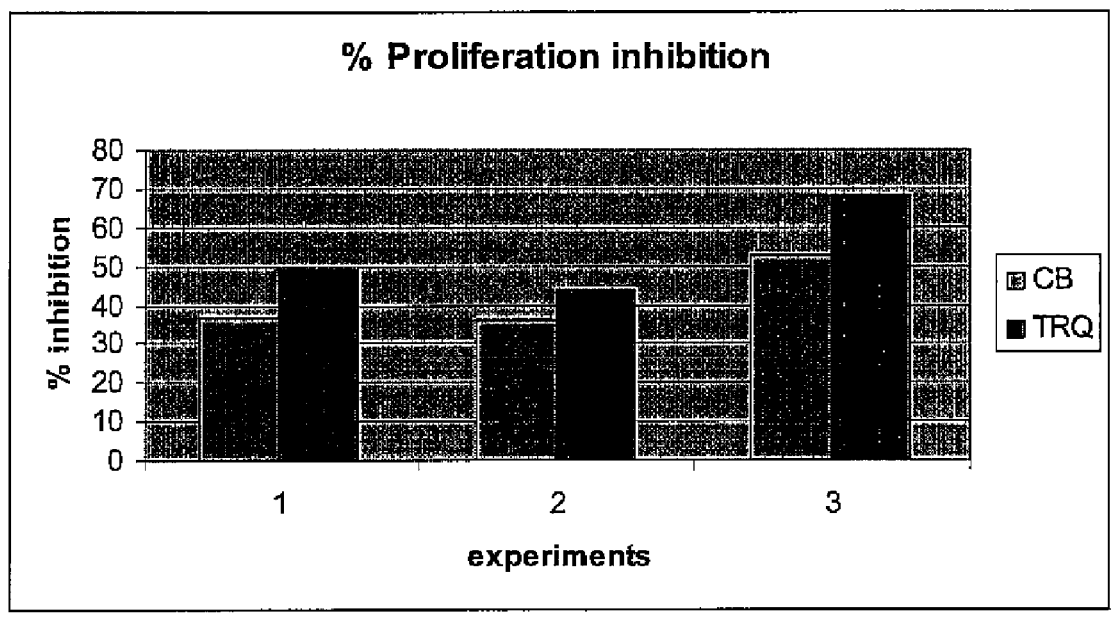
FIG. 10 shows the effects of TRQ or CB on a cell assay using mouse medullary cells C57B1/6 expressing H4R. CB inhibits the proliferation of CFC at a dose of $10^{-5}$M (10 μM) and was compared to TRQ at the dose of $10^{-5}$M (10 μM). TRQ is a more potent inhibitor of cell proliferation than Clobenpropit, as described in Example 16.

TRQ was a more potent inhibitor of cell proliferation than the Clobenpropit. This inhibition is due to the TRQ agonist activity on the H4R as shown in FIG. 10.

Example 17

Effect of TRQ, E1 and E2 on Haematopoietic Progenitor Cells

Mouse C57B1/6 Haematopoietic stem cells were enriched with bone marrow cells by magnetic sorting. Only cells expressing surface tyrosine kinase were sorted. Cells were incubated for 2 hours with growth factors (IL-3 10 ng/ml, IL-6 10 ng/ml, SCF 50 ng/ml) and TRQ and its enantiomers, E1 and E2.

After 2 hours of incubation, cells were washed and incubated with vibrating cell Dye cycle for 30 minutes read by FACS scan.

Figure 13:
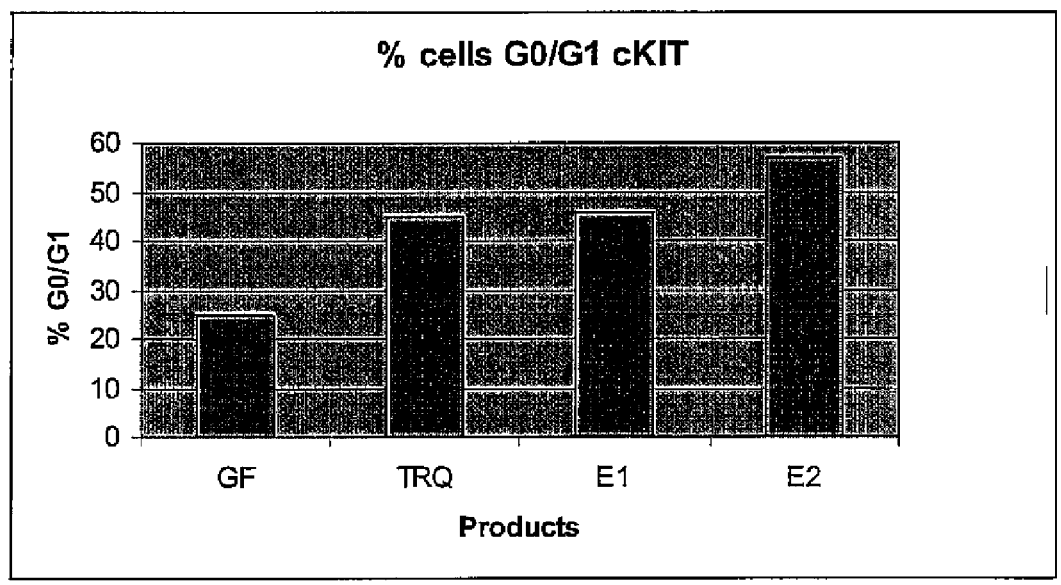
FIG. 13 is a graph showing that enantiomer E2 is a more effective inhibitor of cell growth than TRQ and E1 (approximately 50% inhibition of G0/G1 phase was observed), whereas E2 inhibited G0/G1 by 57%, as described in Example 17.

Enantiomer E2 was found to be a more effective inhibitor of cell growth than TRQ and E1 (approximately 50% inhibition of G0/G1 phase was observed), whereas E2 inhibited G0/G1 by 57% (FIG. 13). This G0/G1 blocking of the cell cycle is reversed if a known H4R antagonist such as JNJ7777120 is used; therefore suggesting that the inhibition of cell proliferation is due to activation of the H4R. Thus, enantiomer E2 was a more potent inhibitor of cell proliferation than E1.

Example 18

Effect of TRQ, Loratadine and Spiriva® to Treat COPD

Tritoqualine when combined with anti-cholinergic drugs with and without loratadine ameliorates conditions of COPD. In this example, the anticholinergic drug Tiotropium bromide (Spiriva®) was combined with TRQ and/or Loratadine to treat the condition of COPD.

The baseline patient was a 58 year old female (height 1.59 m, WEIGHT 70 Kg) with a COPD history.
The COPD History Prior to the Initial Visit (T0)

At the initial visit to the physician (T0), the patient was examined, and the spirometry parameter FEV1 was recorded. Tritoqualine 200 mg/day and Spiriva® (anticholinergic) 2 puffs/day (2.5 micrograms of drug per puff) were added to the patient's existing drug therapy. The patient had undergone physician examinations: 8 weeks, 6 months after the start of the Tritoqualine/Spiriva® treatment (T0). During each visit, the patient's overall health and the FEV1 parameter was assessed by spirometry. Results from each visit are illustrated in Table 20.

TABLE 20

| Spirometry Parameter (L/s) | T0 (initial visit) | T2 (8 weeks) | T3 (6 months) |
|---|---|---|---|
| FEV1 | 1.39 | 1.99 | 2.02 |
| FEV1 Normal value* | 2.28 | 2.28 | 2.28 |

*Normal Value is a value expected for healthy individuals based on age, and height During the period of treatment the patient showed improvement as the spirometry parameter FEV1 increased by 45.3% (from 1.39-2.02) during the 6 month treatment period.

The results show that the additional therapy, Tritoqualine 200 mg/day and Spiriva® (2 puffs per day) ameliorated the COPD symptoms of the patient by significantly improving the spirometry parameter FEV1 by 45.3% (0.63 L/s in 6 months).

Example 19

Effect of TRQ, Loratadine and Spiriva® to Treat COPD

Tritoqualine when combined with anti-cholinergic drugs with and without loratadine ameliorates conditions of COPD. In this example, the anticholinergic drug Tiotropium bromide (Spiriva®) was combined with TRQ and/or Loratadine to treat the condition of COPD.

The baseline patient was a 62 year old male (height 1.70 m, WEIGHT 85 Kg) with a COPD history.

The COPD History Prior to the Initial Visit (T0)

At the initial visit to the physician (T0), the patient was examined and the spirometry parameter FEV1 was recorded. Tritoqualine 200 mg/day, Loratidine 10 mg/day and Spiriva® (anticholinergic) 2 puffs/day (2.5 micrograms of drug per puff) were added to the patient's existing drug therapy. The patient had undergone physician examinations: 6 weeks, 4 months and 10 months after the start of the Tritoqualine/Loratadine/Spiriva® treatment (T0). During each visit the patient's overall health and the FEV1 parameter was assessed by spirometry. Results from each visit are illustrated in Table 21.

TABLE 21

| Spirometry Parameter (L/s) | T0 (initial visit) | T2 (6 weeks) | T3 (4 months) | T3 (10 months) |
|---|---|---|---|---|
| FEV1 | 1.21 | 1.3 | 1.70 | 1.86 |
| FEV1 Normal value* | 2.81 | 2.81 | 2.81 | 2.81 |

*Normal Value is a value expected for healthy individuals based on age, and height During the period of treatment the patient showed improvement as the spirometry parameter FEV1 increased by 53.72.0% (from 1.21-1.86) during the 10 month treatment period, indicating improvement.

Therefore, the additional therapy, Tritoqualine 200 mg/day, loratadine 10 mg/day and Spiriva® (2 puffs per day) ameliorated the COPD symptoms of the patient by significantly improving the spirometry parameter FEV1 by 53.72% (0.65 L/s in 6 months).

Example 20

TRQ racemic mixture (contains a mix of D1 and D2 (also known as E1 and E2, respectively)) and purified isomers as well as CB inhibit proliferation of Colony Forming Cells (CFC) and demonstrates that TRQ exhibits agonist action on H4R similar to CB.

Using the assay described in Example 15, above, the effect of TRQ or CB on cells expressing H4R was tested. Mouse medullary cells C57B1/6 expressing H4R (50,000 cells/Petri dish) were incubated in a semi-solid media with haematopoietic growth factors (IL-3: 10 ng/ml) for 7 days with a TRQ (racemic mixture of RR and SS isomers at 1 µM and 10 µM concentration); TRQ isomer E1 (10 µM concentration); TRQ isomer E2 (10 µM concentration) and CB (10 µM concentration). In this test CB inhibits the proliferation of CFC at the classic dose of $10^{-5}$M (10 µM) and was compared to TRQ at the doses of $10^{-5}$M and $10^{-6}$M (10 µM and 1 µM).

Figure 14:
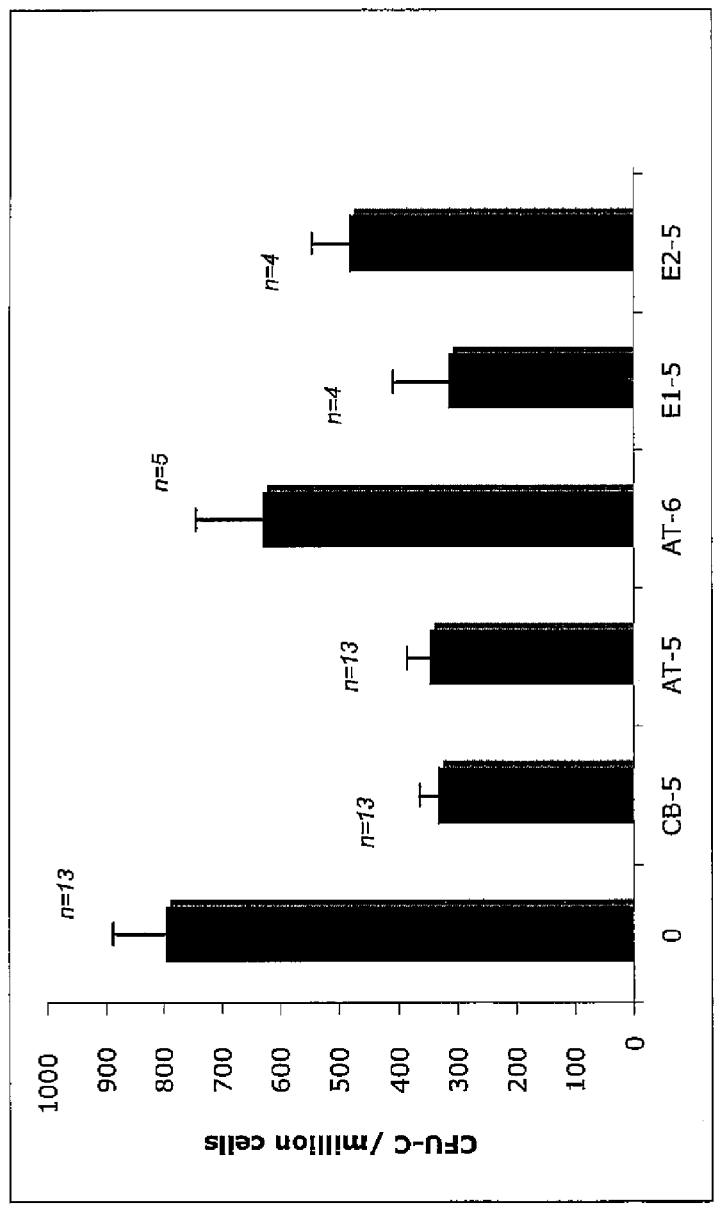
FIG. 14 is a bar graph showing that tritoqualine (TRQ) is an H4 agonist. CB-5 is clobenpropit at $1 \times 10^{-5}$ M (10 uM); AT is a mixture of tritoqualine isomer 1 (also referred to herein as E1 or D1) and 2 (also referred to herein as E2 or D2) at $1 \times 10^{-5}$ M (10 uM); AT-6 is a mixture of tritoqualine isomer 1 and 2 at $1 \times 10^{-6}$ M (1 uM); E1-5 is tritoqualine isomer 1 at $1 \times 10^{-5}$ M (10 uM); E2-5 is tritoqualine isomer 2 at $1 \times 10^{-5}$ M (10 uM).

Racemic TRQ exerted similar inhibitory activity of cell proliferation compared to that of Clobenpropit (CB), both tested at the 10 µM concentration. At the 1 µM level racemic TRQ showed less inhibitory activity in comparison to 10 µM CB. Purified TRQ isomers E1 and E2 also exerted inhibitory activity of cell proliferation at the 10 µM level with isomer E1 to be slightly more potent than isomer E2. This inhibition of cell proliferation is due to the TRQ agonist activity on the H4R. All results for this example are shown in FIG. 14.

Example 21

Analysis of the Cell Cycle of Haematopoietic Progenitor Cells to Test Tritoqualine racemate and purified enantiomers demonstrating agonist action on H4R. This experiment was conducted at two concentrations for all TRQ molecules (10 µM and 1 µM) in the presence and absence of CB (10 µM).

Using the assay described in Example 15, above, the effect of TRQ or CB on cells expressing H4R was tested. Mouse medullary cells C57B1/6 expressing H4R (50,000 cells/Petri dish) were incubated in a semi-solid media with haematopoietic growth factors such as IL-3 (10 ng/ml) for 7 days with a TRQ (racemic mixture of RR and SS isomers at 1 µM and 10 µM concentration); purified TRQ isomer E1 (10 µM and 1 µM concentration); purified TRQ isomer E2 (10 µM and 1 µM concentration) and CB (10 µM concentration). Results from these experiments show that CB increases the percentage of cells at the G0/G1 phase at the classic dose of $10^{-5}$M (10 µM); TRQ (racemic mixture) at the doses of $10^{-5}$M and $10^{-6}$M (10 µM and 1 µM) also increased the percentage of cells at the G0/G1 phase compared to the control (GF only). When an equimolar quantity of CB was concomitantly present with TRQ, the percentage of cells at the G0/G1 phase further increased. Similar results were shown with the purified TRQ isomers. In each experiment cells were incubated in the presence of growth factors (GF, FIG. 15).

CB exerted slightly better inhibitory activity of cell proliferation compared to that of Racemic TRQ, both tested at the 10 µM concentration. At the 1 µM level racemic TRQ presented less inhibitory activity in comparison to 10 µM CB. Purified TRQ isomers E1 and E2 also exerted inhibitory activity of cell proliferation at the 10 µM level with isomer E1 to be slightly more potent than isomer E2. Surprisingly, at the 1 µM level the purified isomers forced a higher percentage of cells at the G0/G1 phase than the racemic TRQ. Upon addition of 10 µM CB the % of cells at the G0/G1 phase further increased suggesting an additive effect between the two molecules (TRQ and CB).

This experiment confirms that forcing cells in the G0/G1 phase, inhibiting the cell cycle, is due to agonist activity on the H4R. Results from this experiment may also predict that H4R agonists such as TRQ or its purified isomers can be used to protect the vulnerable hematopoietic cells from the cytotoxicity of anticancer drugs by forcing cells to stay in the G0/G1 phase (inhibiting the cell cycle) whereby the chemotherapeutic agent is less destructive. In general, anticancer agents affect dividing cells; cells at the G0/G1 phase although metabolically active, are not able to divide.

Figure 15A:
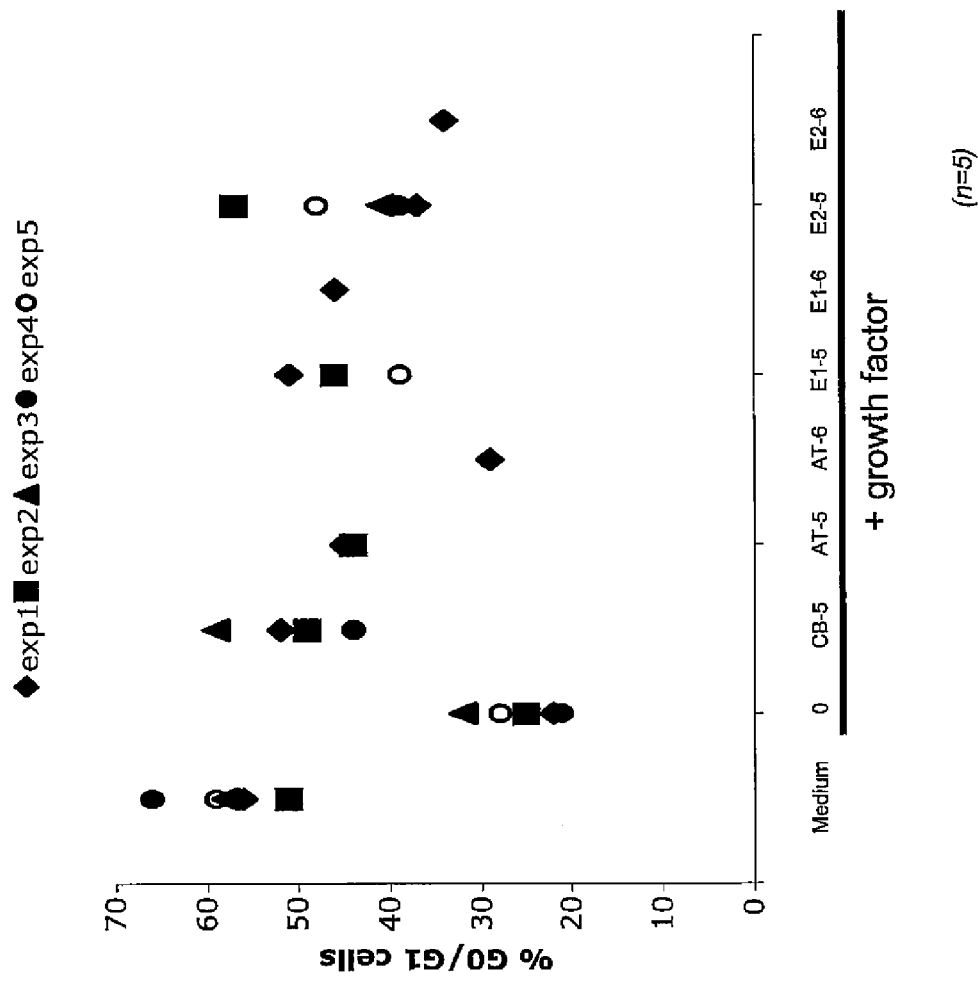
FIG. 15A is a scatter plot and FIG. 15B is a bar graph both showing that TRQ inhibits progenitor cell cycling. CB-5 is clobenpropit-5; AT is a mixture of tritoqualine isomer 1 and 2 at $1 \times 10^{-5}$ M (10 uM); AT-6 is a mixture of tritoqualine isomer 1 and 2 at $1 \times 10^{-6}$ M (1 uM); E1-5 is tritoqualine isomer 1 at $1 \times 10^{-5}$ M (10 uM); E1-6 is tritoqualine isomer 1 at $1 \times 10^{-6}$ M (1 uM); E2-5 is tritoqualine isomer 2 at $1 \times 10^{-5}$ M (10 uM); E2-6 is tritoqualine isomer 2 at $1 \times 10^{-6}$ M (1 uM).
Figure 15B:
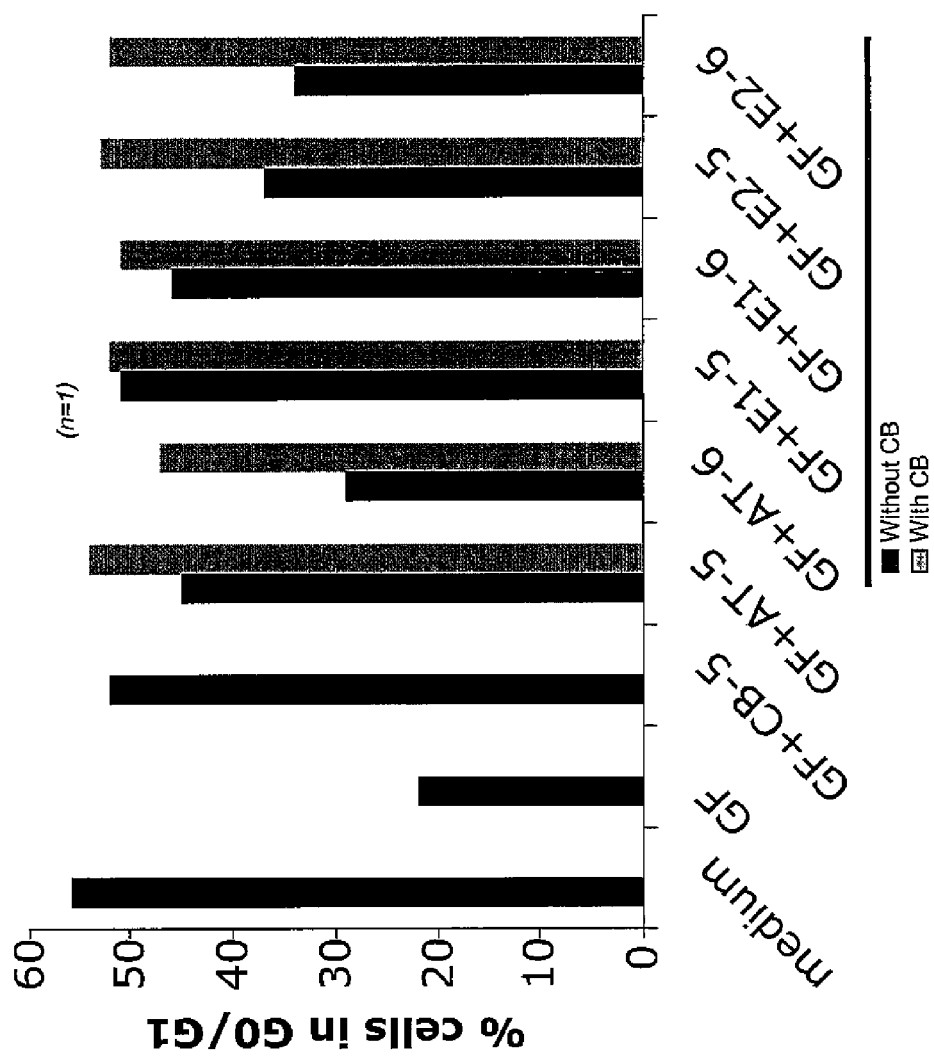

All results for this example are shown in FIG. 15 (two graphs illustrating the same data).

Example 22

The data herein shows that TRQ inhibits ckit positive hematopoietic progenitor cell proliferation.

Figure 16:
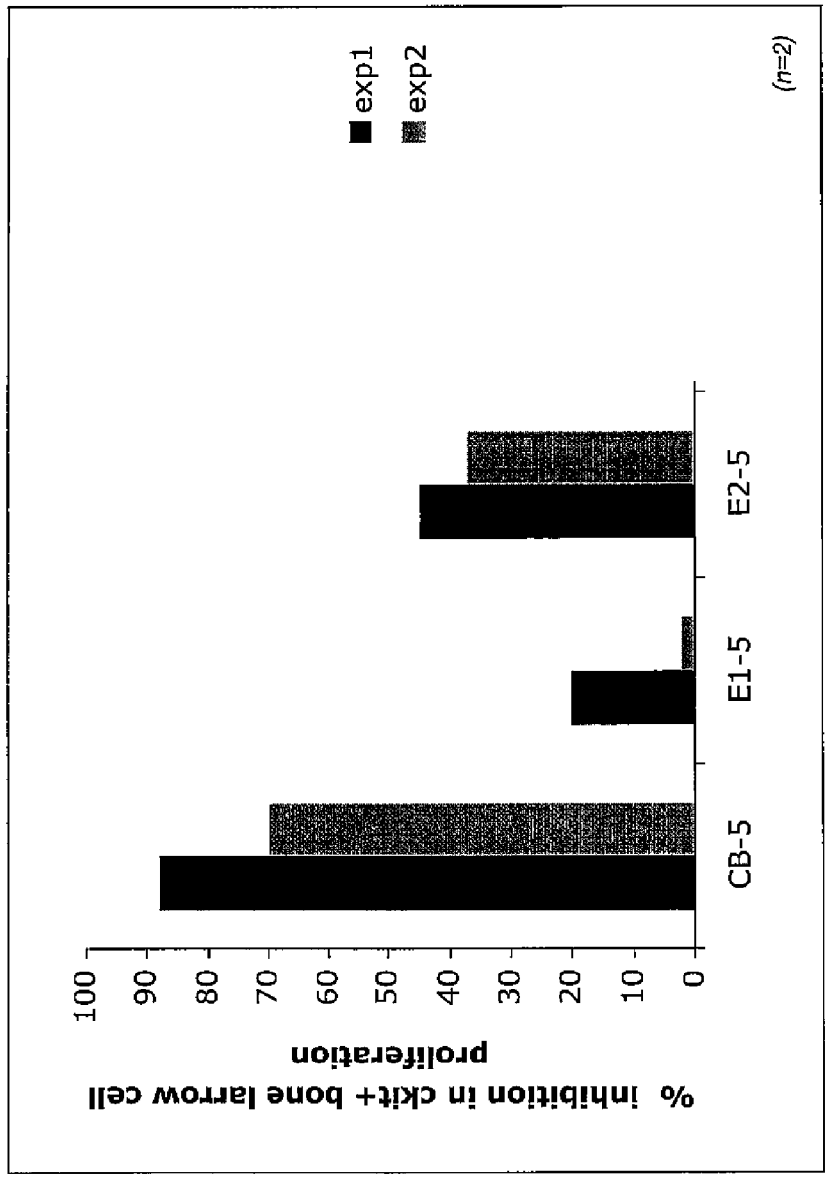
FIG. 16 is a bar graph that shows that TRQ inhibits ckit positive hematopoietic progenitor cell proliferation. The reference to CB-5, E1-5, and E2-5 is the same as FIG. 15.
Figure 17A:
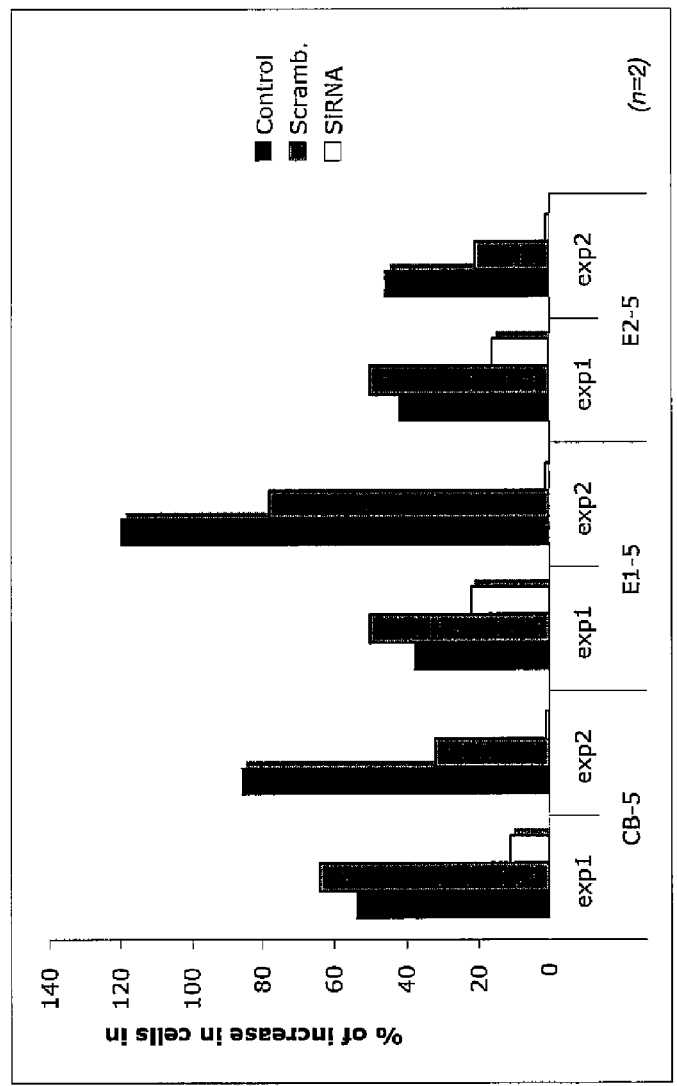
FIG. 17 includes three bar graphs (FIGS. 17A, B and C) showing that TRQ promotes cells to enter and remain in the G0 and/or G1 phase of the cell cycle.
Figure 17B:
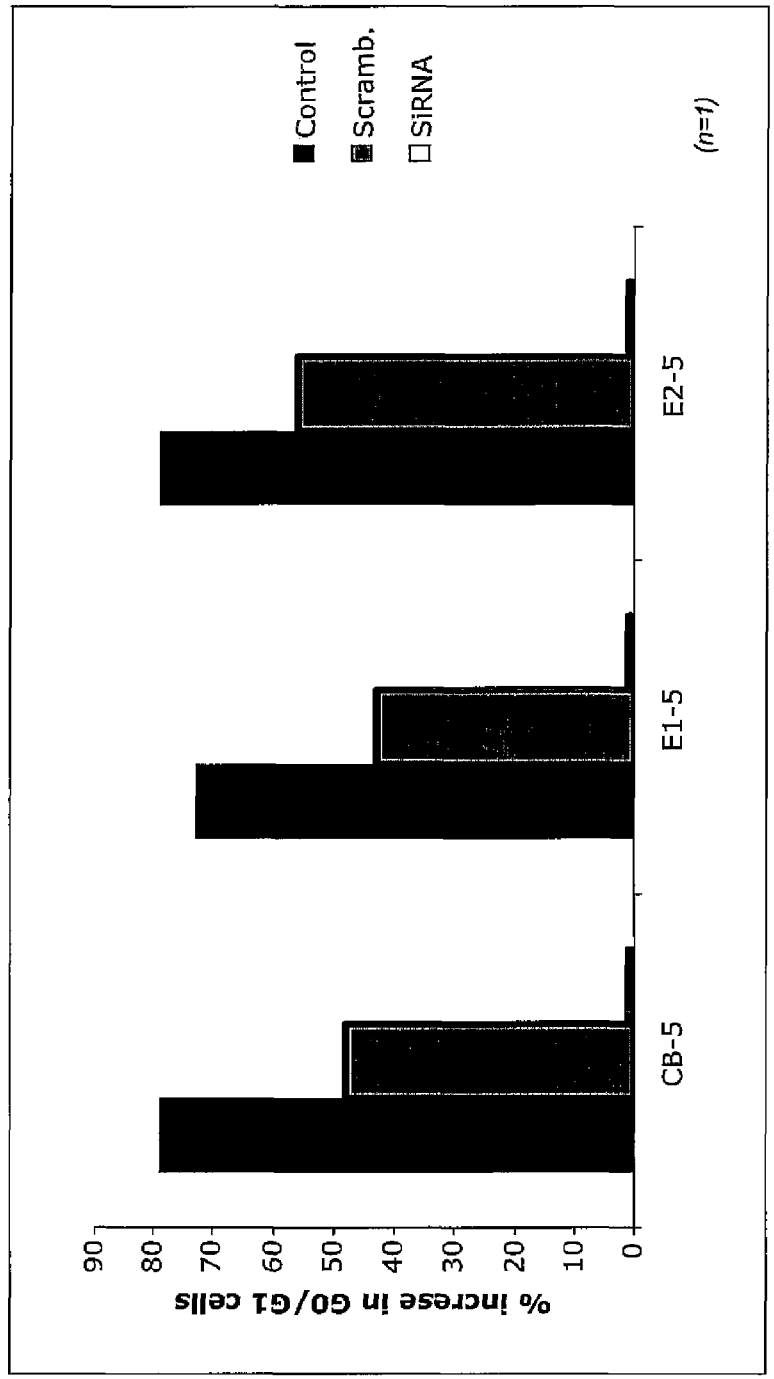
Figure 17C:
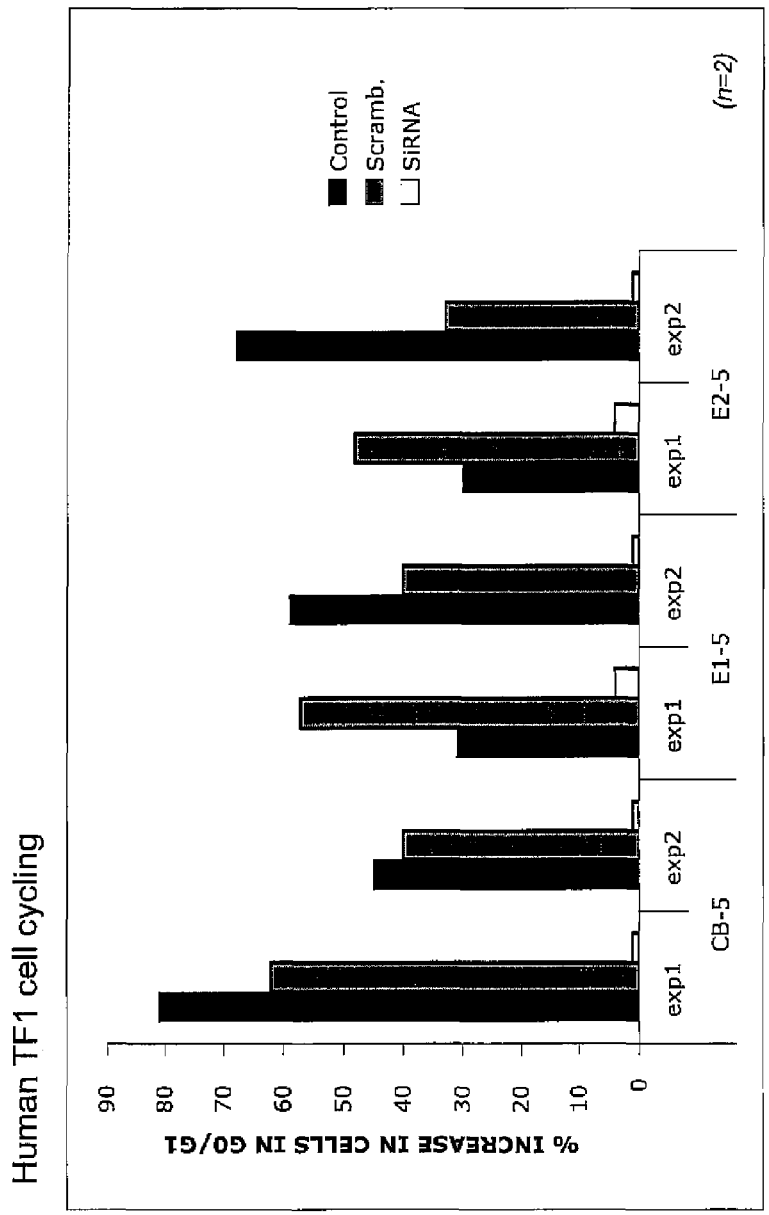
Figure 19:
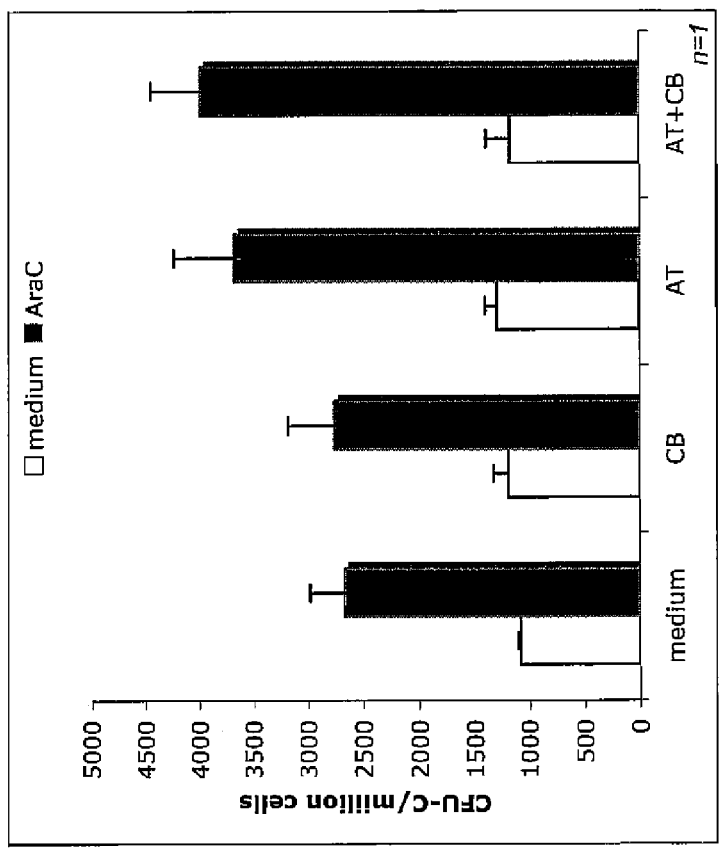
FIG. 19 is a bar graph that shows that TRQ maintains the hematopoietic progenitor cells in the G0 and/or G1 phase of the cell cycle so that even in the presence of Ara-C the cell CFU remains high.
Figure 20A:
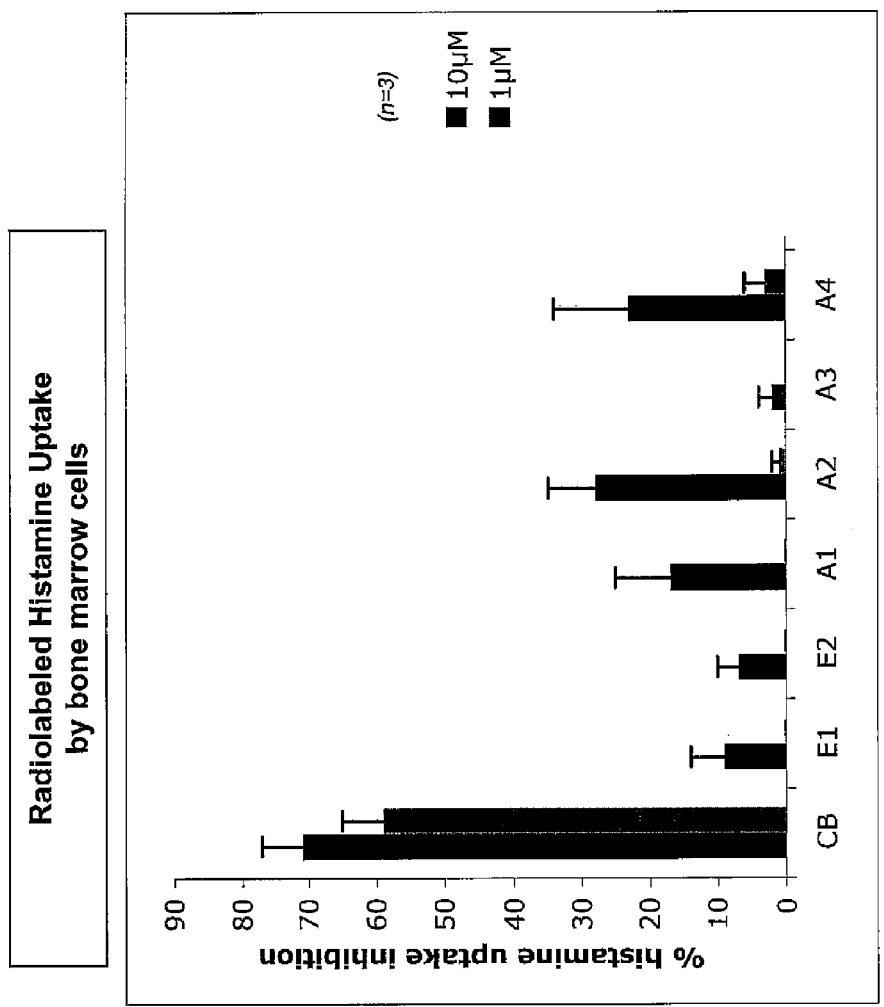
FIG. 20 includes two bar graphs (FIGS. 20A and B) that shows that TRQ is an H4 agonist but does not affect organic cation transporter-3 (OCT-3) or serotonin transporter (SERT).
Figure 20B:
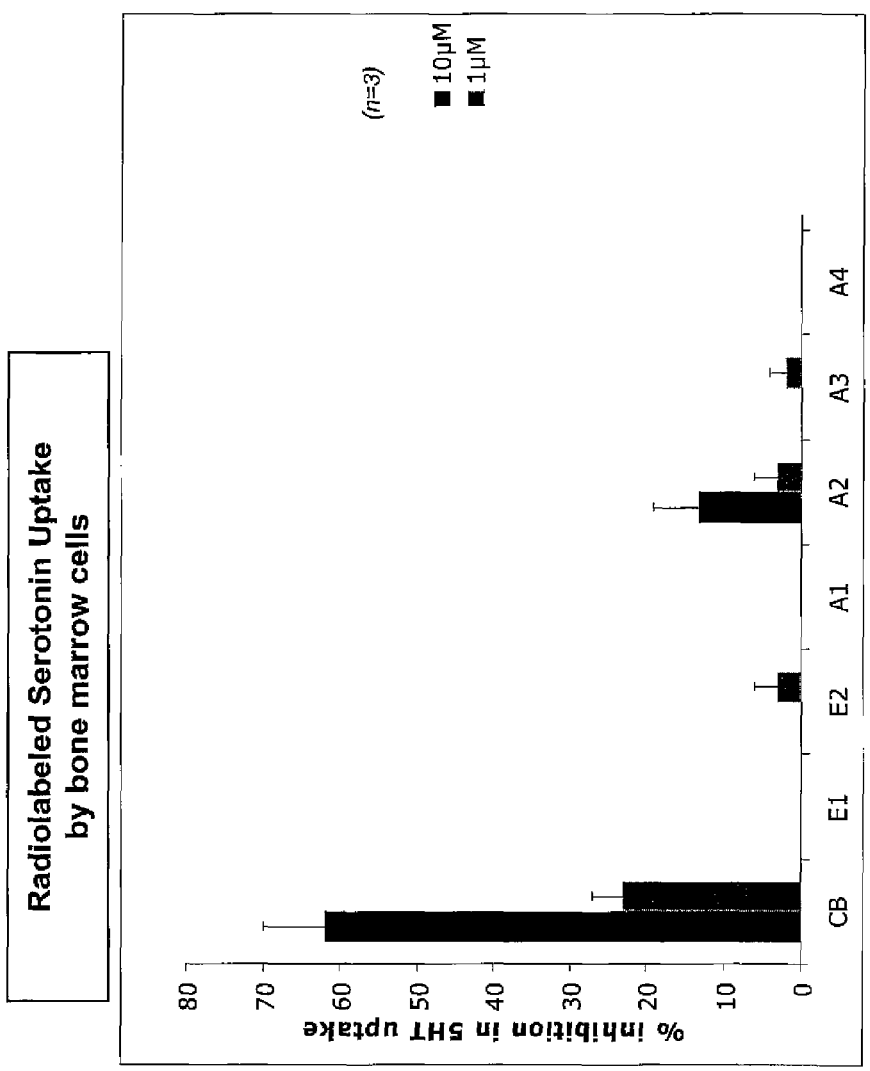

In FIG. 16 the reference to CB-5, E1-5, and E2-5 is the same as above. CKit is a receptor on the surface of hematopoetic cells. Quantifying the ckit receptor is a measure of the differentiation from the progenitor state to the hematopoetic cell state. Here we show that H4 agonists have an inhibitory effect on the expression of the ckit receptor.

CB inhibits of ckit expression on ckit positive hematopoietic progenitor cells. The above graph shows that TRQ, like CB, has a similar effect, e.g., at 10 μM.

Example 23

This experiment shows that the results seen with CB and Tritoqualine isomers E1 and E2 are due to action on the H4R. H4R siRNA specifically inhibits the expression for the H4R. Therefore, the activity of H4R agonists such as CB and Tritoqualine isomers E1 (10 μM) and E2 (10 μM) inhibiting the cell cycle at the G0/G1 phase is reversed.

Materials and Methods

H4R silencing was performed with freshly sorted c-kit$^+$ cells. For transfection, 3 μl of HiPerFect reagent (Qiagen; Courtaboeuf, France) and 4 μl (40 μmol) of human and 8 μl (80 pmol) of murine H4R siRNA, scrambled FITC-labeled or unconjugated control siRNAs (all from Santa Cruz Biotechnology) were incubated in 50 μl x-vivo medium (Cambrex; East Rutherford, N.J.) for 20 min at room temperature. The mixture was then added to 50 μl of cell suspension at a final concentration of $10^6$ cells/ml and incubated for 20 h, when transfection efficiency was verified with scrambled FITC-conjugated siRNA. Cells were then centrifuged and resuspended at a concentration of $10^5$ cells/ml in StemSpan medium with growth factor cocktail. The extinction of H4R protein expression was ascertained by FACS analysis after 24 h. After 3 days of culture with or without tritoqualine (10 μM) or Clobenpropit (10 μM) cells were counted and their viability was assessed by trypan blue exclusion. The cell cycle status was assessed after an overnight incubation.

Results and Discussion

As shown in figures below, the populations of cells treated with SiRNA and H4R antagonists CB and Tritoqualine isomers were significantly reduced compared to the control or non-specific, scrambled, RNA (this scrambled RNA has no effect on the expression of the H4R). Thus, H4R interacting with an H4R agonist will increase the population of cells in the G0/G1 phase.

Example 24

This experiment shows that the increase of the percentage of cells in the G0/G1 phase is reversed when effect of *Bordetella pertussis* toxin (PTX), an inhibitor of $G_{i/o}$ coupling to the H4R is used. This experiment confirms that tritoqualine isomers E1 and E2 have an H4R agonist activity similar to the one of CB.

Cell cultures. Bone marrow (BM) cells were prepared as reported (Schneider, et al. *J. Immunol.* 139:3710-717) and adjusted to a final concentration of 2.5×10$^6$ per ml in culture medium (MEM) supplemented with 10% horse serum. Various doses ($10^{-5}$-$10^{-7}$ M) of Clobenpropit or Tritoqualine were added shortly before the addition of IL-3 (1 ng/ml), followed by a 24-h incubation at 37° C., 5% $CO_2$.

Progenitor-enriched murine c-kit$^+$ BM or cord blood-derived CD34$^+$ cells were prepared by positive magnetic selection, suspended at a final concentration of 10$^5$ per ml in serum-free StemSpan medium (StemCell Technologies) and cultured up to 3 days in the presence of 10 ng of IL-3, 10 ng of IL-6 and 50 ng of SCF (Stem Cell Factor) per ml, with or without Clobenpropit ($10^{-5}$ M), Tritoqualine or both.

Murine CFU-GM (Colony-forming Unit-Granulocyte/Macrophage) were quantified in MethoCult M3230 (StemCell Technologies) supplemented with IL-3 (1 ng/ml). They were plated in a final volume of 1 ml at a concentration of 5×10$^4$ total BM cells/culture dish (Falcon 1008) with or without Clobenpropit, Tritoqualine or both. Colonies were scored on day 7.

Evaluation of Cell Cycle Status

Magnetically sorted c-kit$^+$ BM cells were incubated for 2 h in StemSpan medium with growth factor cocktail alone or in the presence of $10^{-5}$ M Clobenpropit, Tritoqualine or enantiomers. The cell cycle status was then assessed using Vybrant DyeCycle Violet (VDV) Stain (Invitrogen), according to the manufacturer's instructions.

The effect of *Bordetella pertussis* toxin (PTX; 100 ng/ml), an inhibitor of $G_{i/o}$ coupling to the H4R, on the cell cycle arrest promoted by receptor activation was evaluated in the same conditions. After incubation, cells were analyzed using FlowJo software.

Results and Discussion

Tritoqualine Isomers (10 μM) have a similar effect to CB through the H4 receptor agonist activity manifested with the percentage of cells at the G0/G1 phase.

Example 25

This data shows that TRQ inhibits the cell cycle and maintains the hematopoietic progenitor cells in the G0 and/or G1 phase of the cell cycle so that even in the presence of Ara-C the cell CFU remains high.

Ara-C is a chemotherapeutic agent that kills cancel cells (or actively dividing cells). Since both CB and TRQ inhibit the cell cycle and keeps the cells in the G0 and G1 cell phase, Ara-C kills fewer cells (nondividing cells) and CB and TRQ provides protection to the cells in the presence of chemotherapeutic agents such as AraC.

Example 26

Organic Cation Transporter-3 (OCT-3) and Serotonin Transporter (SERT) are important mechanisms of monoamine transport. Many drugs and drug candidates may have significant activity on a therapeutic target, are not therapeutically useful because they significantly inhibit these transporters. It is therefore preferred that tritoqualine isomers have significantly reduced activity on the OCT-3 and SERT transporters.

This Example illustrates that TRQ and isomers do not significantly alter biogenic monoamine update either by the Organic Cation Transporter-3 (OCT-3) or by Serotonin Transporter (SERT).

Materials and Methods

Cell cultures. Bone marrow (BM) cells were prepared as reported (Schneider, et al. *J. Immunol.* 139:3710-717) and adjusted to a final concentration of 2.5×10$^6$ per ml in culture medium (MEM) supplemented with 10% horse serum. Various doses ($10^{-5}$-$10^{-7}$ M) of Clobenpropit or Tritoqualine were added shortly before the addition of IL-3 (1 ng/ml), followed by a 24-h incubation at 37° C., 5% $CO_2$.

Progenitor-enriched murine c-kit$^+$ BM or cord blood-derived CD34$^+$ cells were prepared by positive magnetic selection, suspended at a final concentration of 10$^5$ per ml in serum-free StemSpan medium (StemCell Technologies) and cultured up to 3 days in the presence of 10 ng of IL-3, 10 ng of IL-6 and 50 ng of SCF (Stem Cell Factor) per ml, with or without Clobenpropit ($10^{-5}$ M), Tritoqualine or both.

Murine CFU-GM (Colony-forming Unit-Granulocyte/Macrophage) were quantified in MethoCult M3230 (StemCell Technologies) supplemented with IL-3 (1 ng/ml). They were plated in a final volume of 1 ml at a concentration of $5 \times 10^4$ total BM cells/culture dish (Falcon 1008) with or without Clobenpropit, Tritoqualine or both. Colonies were scored on day 7.

In some experiments, enantiomers were used instead of the racemic mixture of Tritoqualine.

Cytokine assays, measurement of histamine production, and uptake. IL-6 and IL-4 production was measured in cell supernatants recovered after a 24-h incubation. Histamine was quantified by an automated continuous flow spectrofluorometric technique (Schneider, et al. *J. Immunol.* 139:3710-717). For binding experiments, $10^6$ total BM cells were plated in round-bottomed 96-well polypropylene plates (Costar). Unless stated otherwise, the cells were incubated (37° C., 5% $CO_2$) for 3 h with 3 µCi/ml of [$^3$H]histamine dihydrochloride ($2.5 \times 10^{-7}$ M; 12 Ci/mmol) in a final volume of 100 µl. Competition assays were performed as previously described (Corbel, S., et al. 1995. *Blood.* 86:531-539; Corbel, S., et al. 1995, *FEBS Lett.* 404:289-293). Each experiment was performed in triplicate, and histamine binding was calculated from total cpm after subtraction of nonspecific binding to filters.

Results and Discussion

It is evident that inhibition of histamine uptake and serotonin uptake is greatly reduced in the presence of tritoqualine isomers E1 and E2 at the 10 µM level and negligible at the 1 µM level. Thus, the fact that these transporters are not affected by tritoqualine is a significant reason for tritoqualine's low toxicity and great therapeutic utility as a drug.

What is claimed is:

1. A method for the treatment of COPD in a subject comprising administering to the subject an effective amount of a composition consisting essentially of Tritoqualine or isomers thereof as the only active agent and pharmaceutically acceptable carriers, binders, diluents, adjuvants, excipients, and/or vehicles thereby treating COPD in the subject.

2. The method of claim 1, wherein the Tritoqualine isomer is E1 or E2.

* * * * *